United States Patent
Harper et al.

(10) Patent No.: US 10,123,752 B2
(45) Date of Patent: Nov. 13, 2018

(54) DISPLAYS FOR A MEDICAL DEVICE

(71) Applicant: Abbott Diabetes Care Inc., Alameda, CA (US)

(72) Inventors: Wesley Scott Harper, Alameda, CA (US); Annie C. Tan, Redwood City, CA (US); Timothy Christian Dunn, San Francisco, CA (US); Mark Kent Sloan, Redwood City, CA (US); Kenneth J. Doniger, Menlo Park, CA (US); Michael Love, Pleasanton, CA (US); Phillip Yee, San Francisco, CA (US); Gary Alan Hayter, Oakland, CA (US); R. Curtis Jennewine, Portland, OR (US); Glenn Howard Berman, Alameda, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 15/808,918

(22) Filed: Nov. 10, 2017

(65) Prior Publication Data
US 2018/0064380 A1 Mar. 8, 2018

Related U.S. Application Data

(63) Continuation of application No. 15/377,989, filed on Dec. 13, 2016, now Pat. No. 9,814,416, which is a
(Continued)

(51) Int. Cl.
*A61B 5/00* (2006.01)
*G16H 40/63* (2018.01)
(Continued)

(52) U.S. Cl.
CPC .......... *A61B 5/743* (2013.01); *A61B 5/14532* (2013.01); *A61B 5/7275* (2013.01);
(Continued)

(58) Field of Classification Search
CPC ..... A61B 5/727; A61B 5/7275; A61B 5/7278; A61B 5/7282; A61B 5/742; A61B 5/7425;
(Continued)

(56) References Cited

U.S. PATENT DOCUMENTS 3,581,062 A 5/1971 Aston
3,926,760 A 12/1975 Allen et al.
(Continued)

FOREIGN PATENT DOCUMENTS

CA 2468577 6/2003
CA 2678336 5/2008
(Continued)

OTHER PUBLICATIONS

European Patent Application No. 10812728.3, Examination Report dated Feb. 28, 2018.
(Continued)

*Primary Examiner* — Van Trieu
(74) *Attorney, Agent, or Firm* — Jackson & Co., LLP

(57) ABSTRACT

Embodiments described herein relate to an analyte monitoring device having a user interface with a display and a plurality of actuators. The display is configured to render a plurality of display screens, including a home screen and an alert screen. The home screen is divided into a plurality of simultaneously displayed panels, with a first panel displays a rate of change of continuously monitored analyte levels in interstitial fluid, a second panel simultaneously displays a current analyte level and an analyte trend indicator, and a third panel displays status information of a plurality of
(Continued)

components of the device. When an alarm condition is detected, the display renders the alert screen in place of the home screen, the alert screen displaying information corresponding to the detected alarm condition. Furthermore, the actuators are configured to affect further output of the analyte monitoring device corresponding to the detected condition.

25 Claims, 30 Drawing Sheets

Related U.S. Application Data continuation of application No. 14/938,840, filed on Nov. 11, 2015, now Pat. No. 9,549,694, which is a continuation of application No. 14/457,066, filed on Aug. 11, 2014, now Pat. No. 9,186,113, which is a continuation of application No. 13/970,556, filed on Aug. 19, 2013, now Pat. No. 8,816,862, which is a continuation of application No. 12/871,901, filed on Aug. 30, 2010, now Pat. No. 8,514,086.

(60) Provisional application No. 61/297,625, filed on Jan. 22, 2010, provisional application No. 61/247,541, filed on Sep. 30, 2009, provisional application No. 61/238,672, filed on Aug. 31, 2009, provisional application No. 61/238,657, filed on Aug. 31, 2009.

(51) Int. Cl.
  *A61B 5/145* (2006.01)
  *G06F 19/00* (2018.01)

(52) U.S. Cl.
  CPC ............ *A61B 5/7282* (2013.01); *A61B 5/746* (2013.01); *A61B 5/748* (2013.01); *A61B 5/7425* (2013.01); *A61B 5/7435* (2013.01); *A61B 5/7445* (2013.01); *G06F 19/00* (2013.01); *G06F 19/3468* (2013.01); *G16H 40/63* (2018.01); *A61B 2560/045* (2013.01); *A61B 2562/0295* (2013.01)

(58) Field of Classification Search
  CPC ..... A61B 5/743; A61B 5/7435; A61B 5/7445; A61B 5/746; A61B 5/748; G06F 19/34; G06F 19/3406
  See application file for complete search history.

(56) References Cited

U.S. PATENT DOCUMENTS

| | | |
|---|---|---|
| 3,949,388 A | 4/1976 | Fuller |
| 3,960,497 A | 6/1976 | Acord et al. |
| 4,033,330 A | 7/1977 | Willis et al. |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,204,264 A | 4/1993 | Kaminer et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,328,460 A | 7/1994 | Lord et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,552,997 A | 9/1996 | Massart |
| 5,555,190 A | 9/1996 | Derby et al. |
| 5,564,434 A | 10/1996 | Halperin et al. |
| 5,568,400 A | 10/1996 | Stark et al. |
| 5,568,806 A | 10/1996 | Cheney, II et al. |
| 5,569,186 A | 10/1996 | Lord et al. |

(56) References Cited

U.S. PATENT DOCUMENTS

| | | |
|---|---|---|
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,726,646 A | 3/1998 | Bane et al. |
| 5,733,259 A | 3/1998 | Valcke et al. |
| 5,735,285 A | 4/1998 | Albert et al. |
| 5,748,103 A | 5/1998 | Flach et al. |
| 5,772,586 A | 6/1998 | Heinonen et al. |
| 5,791,344 A | 8/1998 | Schulman et al. |
| 5,899,855 A | 5/1999 | Brown |
| 5,914,026 A | 6/1999 | Blubaugh, Jr. et al. |
| 5,919,141 A | 7/1999 | Money et al. |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,032,119 A | 2/2000 | Brown et al. |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,157,850 A | 12/2000 | Diab et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,498,043 B1 | 12/2002 | Schulman et al. |
| 6,514,718 B2 | 2/2003 | Heller et al. |
| 6,544,212 B2 | 4/2003 | Galley et al. |
| 6,546,268 B1 | 4/2003 | Ishikawa et al. |
| 6,551,494 B1 | 4/2003 | Heller et al. |
| 6,554,798 B1 | 4/2003 | Mann et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,631,281 B1 | 10/2003 | Kastle |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,730,025 B1 | 5/2004 | Platt |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,931,327 B2 | 8/2005 | Goode, Jr. et al. |

(56) References Cited

U.S. PATENT DOCUMENTS

| | | |
|---|---|---|
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,015,817 B2 | 3/2006 | Copley et al. |
| 7,016,713 B2 | 3/2006 | Gardner et al. |
| 7,022,072 B2 | 4/2006 | Fox et al. |
| 7,022,219 B2 | 4/2006 | Mansouri et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,046,153 B2 | 5/2006 | Oja et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,179,226 B2 | 2/2007 | Crothall et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,241,266 B2 | 7/2007 | Zhou et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,286,894 B1 | 10/2007 | Grant et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,401,111 B1 | 7/2008 | Batman et al. |
| 7,402,153 B2 | 7/2008 | Steil et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,654,956 B2 | 2/2010 | Brister et al. |
| 7,657,297 B2 | 2/2010 | Simpson et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,736,310 B2 | 6/2010 | Taub et al. |
| 7,766,829 B2 | 8/2010 | Sloan et al. |
| 7,768,387 B2 | 8/2010 | Fennell et al. |
| 7,774,145 B2 | 8/2010 | Bruaker et al. |
| 7,778,680 B2 | 8/2010 | Goode, Jr. et al. |
| 7,785,256 B1 | 8/2010 | Koh |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode et al. |
| 7,885,698 B2 | 2/2011 | Feldman et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,912,655 B2 | 3/2011 | Power et al. |
| 7,912,674 B2 | 3/2011 | Clark et al. |
| 7,914,450 B2 | 3/2011 | Goode, Jr. et al. |
| 7,920,907 B2 | 4/2011 | McGarraugh et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,976,467 B2 | 7/2011 | Young et al. |
| 7,978,063 B2 | 7/2011 | Baldus et al. |
| 7,996,158 B2 | 8/2011 | Hayter et al. |
| 8,005,524 B2 | 8/2011 | Brauker et al. |
| 8,010,174 B2 | 8/2011 | Goode et al. |
| 8,010,256 B2 | 8/2011 | Oowada |
| 8,066,639 B2 | 11/2011 | Nelson et al. |
| 8,160,900 B2 | 4/2012 | Taub et al. |
| 8,192,394 B2 | 6/2012 | Estes et al. |
| 8,207,859 B2 | 6/2012 | Enegren et al. |
| 8,216,138 B1 | 7/2012 | McGarraugh et al. |
| 8,255,026 B1 | 8/2012 | Al-Ali |
| 8,282,549 B2 | 10/2012 | Brauker et al. |
| 8,374,668 B1 | 2/2013 | Hayter et al. |
| 8,461,985 B2 | 6/2013 | Fennell et al. |
| 8,478,557 B2 | 7/2013 | Hayter et al. |
| 8,497,777 B2 | 7/2013 | Harper |
| 8,583,205 B2 | 11/2013 | Budiman et al. |
| 8,597,570 B2 | 12/2013 | Terashima et al. |
| 8,600,681 B2 | 12/2013 | Hayter et al. |
| 8,710,993 B2 | 4/2014 | Hayter et al. |
| 8,730,058 B2 | 5/2014 | Harper |
| 8,734,422 B2 | 5/2014 | Hayter |
| 8,816,862 B2 | 8/2014 | Harper et al. |
| 8,834,366 B2 | 9/2014 | Hayter et al. |
| 8,845,536 B2 | 9/2014 | Brauker et al. |

(56) References Cited

U.S. PATENT DOCUMENTS

| | | |
|---|---|---|
| 9,178,752 B2 | 11/2015 | Harper |
| 9,289,179 B2 | 3/2016 | Hayter et al. |
| 9,498,165 B2 | 11/2016 | Johnson et al. |
| 9,504,430 B2 | 11/2016 | Johnson et al. |
| 2001/0037366 A1 | 11/2001 | Webb et al. |
| 2002/0019022 A1 | 2/2002 | Dunn et al. |
| 2002/0042090 A1 | 4/2002 | Heller et al. |
| 2002/0054320 A1 | 5/2002 | Ogino |
| 2002/0068860 A1 | 6/2002 | Clark |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0117639 A1 | 8/2002 | Paolini et al. |
| 2002/0120186 A1 | 8/2002 | Keimel |
| 2002/0128594 A1 | 9/2002 | Das et al. |
| 2002/0147135 A1 | 10/2002 | Schnell |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0099529 A1 | 5/2004 | Mao et al. |
| 2004/0106858 A1 | 6/2004 | Say et al. |
| 2004/0111017 A1 | 6/2004 | Say et al. |
| 2004/0117204 A1 | 6/2004 | Mazar et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138588 A1 | 7/2004 | Saikley et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0134731 A1 | 6/2005 | Lee et al. |
| 2005/0137530 A1 | 6/2005 | Campbell et al. |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0184153 A1 | 8/2005 | Auchinleck |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |

(56) References Cited

U.S. PATENT DOCUMENTS

| | | |
|---|---|---|
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0290496 A1 | 12/2006 | Peeters et al. |
| 2006/0293607 A1 | 12/2006 | Alt et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027507 A1 | 2/2007 | Burdett et al. |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0038053 A1 | 2/2007 | Berner et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078314 A1 | 4/2007 | Grounsell et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0191702 A1 | 8/2007 | Yodfat et al. |
| 2007/0197889 A1 | 8/2007 | Brauker et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0249922 A1 | 10/2007 | Peyser et al. |
| 2007/0255321 A1 | 11/2007 | Gerber et al. |
| 2007/0255348 A1 | 11/2007 | Holtzclaw |
| 2007/0270672 A1 | 11/2007 | Hayter et al. |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0114228 A1 | 5/2008 | McCluskey et al. |
| 2008/0119703 A1 | 5/2008 | Brister et al. |
| 2008/0119708 A1 | 5/2008 | Budiman |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |

(56) References Cited

U.S. PATENT DOCUMENTS

| | | |
|---|---|---|
| 2008/0208025 A1 | 8/2008 | Shults et al. |
| 2008/0208113 A1 | 8/2008 | Damiano et al. |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234943 A1 | 9/2008 | Ray et al. |
| 2008/0234992 A1 | 9/2008 | Ray et al. |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saudara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0278331 A1 | 11/2008 | Hayter et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev |
| 2008/0319085 A1 | 12/2008 | Wright et al. |
| 2008/0319279 A1 | 12/2008 | Ramsay et al. |
| 2009/0005665 A1 | 1/2009 | Hayter et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054750 A1 | 2/2009 | Jennewine |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085873 A1 | 4/2009 | Betts et al. |
| 2009/0093687 A1 | 4/2009 | Telfort et al. |
| 2009/0099436 A1 | 4/2009 | Brister et al. |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112154 A1 | 4/2009 | Montgomery et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0157430 A1 | 6/2009 | Rule et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0210249 A1 | 8/2009 | Rasch-Menges et al. |
| 2009/0216100 A1 | 8/2009 | Ebner et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0287073 A1 | 11/2009 | Boock et al. |
| 2009/0287074 A1 | 11/2009 | Shults et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022988 A1 | 1/2010 | Wochner et al. |
| 2010/0023291 A1 | 1/2010 | Hayter et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |

(56) References Cited

U.S. PATENT DOCUMENTS

| | | |
|---|---|---|
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0093786 A1 | 4/2010 | Watanabe et al. |
| 2010/0094251 A1 | 4/2010 | Estes et al. |
| 2010/0095229 A1 | 4/2010 | Dixon et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121167 A1 | 5/2010 | McGarraugh et al. |
| 2010/0121169 A1 | 5/2010 | Petisce et al. |
| 2010/0141656 A1 | 6/2010 | Krieftewirth |
| 2010/0152548 A1 | 6/2010 | Koski |
| 2010/0152554 A1 | 6/2010 | Steine et al. |
| 2010/0160757 A1 | 6/2010 | Weinert et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0174266 A1 | 7/2010 | Estes |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185075 A1 | 7/2010 | Brister et al. |
| 2010/0185175 A1 | 7/2010 | Kamen et al. |
| 2010/0191082 A1 | 7/2010 | Brister et al. |
| 2010/0191085 A1 | 7/2010 | Budiman |
| 2010/0191087 A1 | 7/2010 | Talbot et al. |
| 2010/0191472 A1 | 7/2010 | Doniger et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0204557 A1 | 8/2010 | Kiaie et al. |
| 2010/0212583 A1 | 8/2010 | Brister et al. |
| 2010/0213080 A1 | 8/2010 | Celentano et al. |
| 2010/0214104 A1 | 8/2010 | Goode et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0230285 A1 | 9/2010 | Hoss et al. |
| 2010/0234710 A1 | 9/2010 | Budiman et al. |
| 2010/0240975 A1 | 9/2010 | Goode et al. |
| 2010/0240976 A1 | 9/2010 | Goode et al. |
| 2010/0249530 A1 | 9/2010 | Rankers et al. |
| 2010/0259543 A1 | 10/2010 | Tarassenko et al. |
| 2010/0261987 A1 | 10/2010 | Kamath et al. |
| 2010/0265073 A1 | 10/2010 | Harper et al. |
| 2010/0274107 A1 | 10/2010 | Boock et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0277342 A1 | 11/2010 | Sicurello et al. |
| 2010/0280341 A1 | 11/2010 | Boock et al. |
| 2010/0280782 A1 | 11/2010 | Harper et al. |
| 2010/0286496 A1 | 11/2010 | Simpson et al. |
| 2010/0298684 A1 | 11/2010 | Leach et al. |
| 2010/0305965 A1 | 12/2010 | Benjamin et al. |
| 2010/0313105 A1 | 12/2010 | Nekoomaram et al. |
| 2010/0324403 A1 | 12/2010 | Brister et al. |
| 2010/0331644 A1 | 12/2010 | Neale et al. |
| 2010/0331648 A1 | 12/2010 | Kamath et al. |
| 2010/0331651 A1 | 12/2010 | Groll |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009724 A1 | 1/2011 | Hill et al. |
| 2011/0009727 A1 | 1/2011 | Mensinger et al. |
| 2011/0009813 A1 | 1/2011 | Rankers et al. |
| 2011/0010257 A1 | 1/2011 | Hill et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0046467 A1 | 2/2011 | Simpson et al. |
| 2011/0053121 A1 | 3/2011 | Heaton |
| 2011/0077469 A1 | 3/2011 | Blocker et al. |
| 2011/0077490 A1 | 3/2011 | Simpson et al. |
| 2011/0077494 A1 | 3/2011 | Doniger et al. |
| 2011/0105873 A1 | 5/2011 | Feldman et al. |
| 2011/0112696 A1 | 5/2011 | Yodfat et al. |
| 2011/0118579 A1 | 5/2011 | Goode et al. |
| 2011/0118580 A1 | 5/2011 | Goode et al. |
| 2011/0123971 A1 | 5/2011 | Berkowitz et al. |
| 2011/0124992 A1 | 5/2011 | Brauker et al. |
| 2011/0124997 A1 | 5/2011 | Goode et al. |
| 2011/0125410 A1 | 5/2011 | Goode et al. |
| 2011/0126188 A1 | 5/2011 | Bernstein et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137571 A1 | 6/2011 | Power et al. |
| 2011/0144465 A1 | 6/2011 | Shults et al. |
| 2011/0148905 A1 | 6/2011 | Simmons et al. |
| 2011/0163880 A1 | 7/2011 | Halff et al. |
| 2011/0163881 A1 | 7/2011 | Halff et al. |
| 2011/0178378 A1 | 7/2011 | Brister et al. |
| 2011/0184268 A1 | 7/2011 | Taub |
| 2011/0184752 A1 | 7/2011 | Ray et al. |
| 2011/0190614 A1 | 8/2011 | Brister et al. |
| 2011/0193704 A1 | 8/2011 | Harper et al. |
| 2011/0196217 A1* | 8/2011 | Myoujou ............ A61B 5/14532 600/365 |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0218414 A1 | 9/2011 | Kamath et al. |
| 2011/0224523 A1 | 9/2011 | Budiman |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0253533 A1 | 10/2011 | Shults et al. |
| 2011/0257895 A1 | 10/2011 | Brauker et al. |

(56) References Cited

U.S. PATENT DOCUMENTS

| | | |
|---|---|---|
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |
| 2011/0282327 A1 | 11/2011 | Kellogg et al. |
| 2011/0287528 A1 | 11/2011 | Fern et al. |
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0319739 A1 | 12/2011 | Kamath et al. |
| 2011/0320130 A1 | 12/2011 | Valdes et al. |
| 2011/0320167 A1 | 12/2011 | Budiman |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0108931 A1 | 5/2012 | Taub |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0245447 A1 | 9/2012 | Karan et al. |
| 2013/0035575 A1 | 2/2013 | Mayou et al. |
| 2013/0235166 A1 | 9/2013 | Jones et al. |
| 2017/0086756 A1 | 3/2017 | Harper et al. |

FOREIGN PATENT DOCUMENTS

| | | |
|---|---|---|
| CA | 2626349 | 9/2008 |
| CA | 2728831 | 7/2011 |
| CA | 2617965 | 10/2011 |
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 2031534 | 3/2009 |
| EP | 1725163 | 12/2010 |
| WO | WO-1996/025089 | 8/1996 |
| WO | WO-1996/035370 | 11/1996 |
| WO | WO-1998/035053 | 8/1998 |
| WO | WO-1999/027849 | 6/1999 |
| WO | WO-1999/028736 | 6/1999 |
| WO | WO-1999/056613 | 11/1999 |
| WO | WO-2000/049940 | 8/2000 |
| WO | WO-2000/059370 | 10/2000 |
| WO | WO-2000/074753 | 12/2000 |
| WO | WO-2001/052935 | 7/2001 |
| WO | WO-2001/054753 | 8/2001 |
| WO | WO-2002/016905 | 2/2002 |
| WO | WO-2003/057027 | 7/2003 |
| WO | WO-2003/076893 | 9/2003 |
| WO | WO-2003/082091 | 10/2003 |
| WO | WO-2004/060455 | 7/2004 |
| WO | WO-2005/057175 | 6/2005 |
| WO | WO-2005/065538 | 7/2005 |
| WO | WO-2005/065542 | 7/2005 |
| WO | WO-2006/020212 | 2/2006 |
| WO | WO-2006/024671 | 3/2006 |
| WO | WO-2006/072035 | 7/2006 |
| WO | WO-2007/019289 | 2/2007 |
| WO | WO-2008/048452 | 4/2008 |
| WO | WO-2008/052374 | 5/2008 |
| WO | WO-2008/062099 | 5/2008 |
| WO | WO-2008/086541 | 7/2008 |
| WO | WO-2008/144445 | 11/2008 |
| WO | WO-2009/097594 | 8/2009 |
| WO | WO-2010/062898 | 6/2010 |
| WO | WO-2011/000528 | 1/2011 |
| WO | WO-2011/104616 | 9/2011 |

OTHER PUBLICATIONS

U.S. Appl. No. 15/199,765, Office Action dated Apr. 5, 2018.

Armour, J. C., et al., "Application of Chronic Intravascular Blood Glucose Sensor in Dogs", *Diabetes*, vol. 39, 1990, pp. 1519-1526.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

(56) References Cited

OTHER PUBLICATIONS

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

European Patent Application No. 10812728.3, Extended European Search Report dated Aug. 21, 2014.

Israeli Patent Application No. 216631, Original Language and English Translation of Official Action dated Sep. 18, 2014.

PCT Application No. PCT/US2010/047194, International Preliminary Report on Patentability and Written Opinion of the International Searching Authority dated Mar. 15, 2012.

PCT Application No. PCT/US2010/047194, International Search Report and Written Opinion of the International Searching Authority dated Dec. 29, 2010.

U.S. Appl. No. 12/871,901, Notice of Allowance dated Apr. 17, 2013.

U.S. Appl. No. 12/871,901, Office Action dated Oct. 25, 2012.

U.S. Appl. No. 13/970,556, Notice of Allowance dated Mar. 20, 2014.

U.S. Appl. No. 13/970,556, Office Action dated Nov. 5, 2013.

U.S. Appl. No. 14/457,066, Notice of Allowance dated Sep. 9, 2015.

U.S. Appl. No. 14/457,066, Office Action dated Jul. 7, 2015.

U.S. Appl. No. 14/592,704, Notice of Allowance dated Oct. 28, 2015.

U.S. Appl. No. 14/592,704, Office Action dated Sep. 17, 2015.

U.S. Appl. No. 14/938,840, Notice of Allowance dated Oct. 27, 2016.

U.S. Appl. No. 14/938,840, Office Action dated May 12, 2016.

U.S. Appl. No. 15/260,288, Office Action dated Jun. 27, 2017.

U.S. Appl. No. 15/377,989, Notice of Allowance dated Jul. 18, 2017.

\* cited by examiner

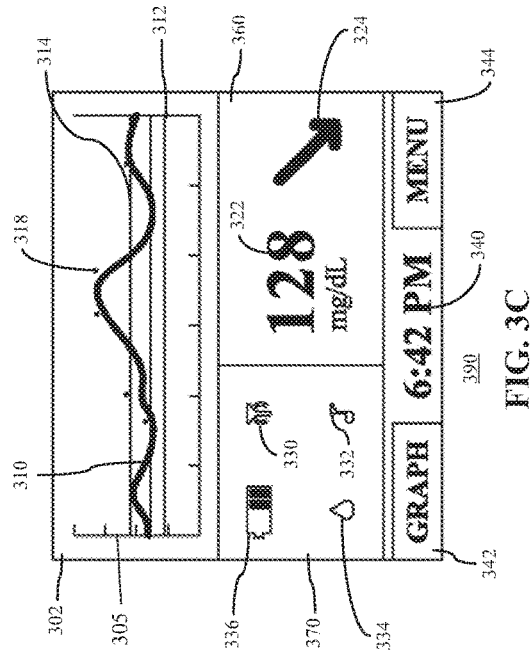
FIG. 3A
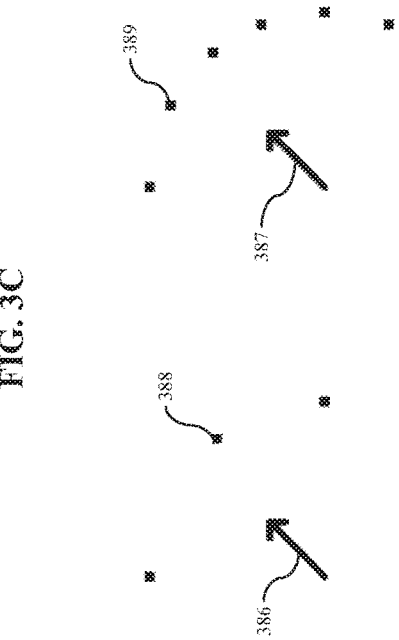
FIG. 3B
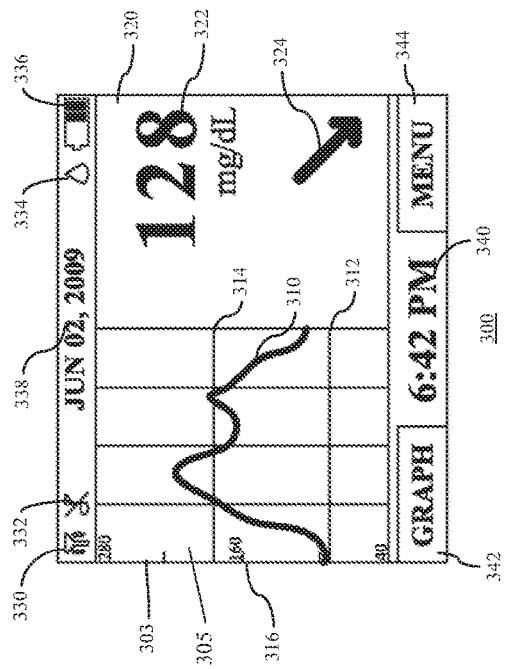
FIG. 3C
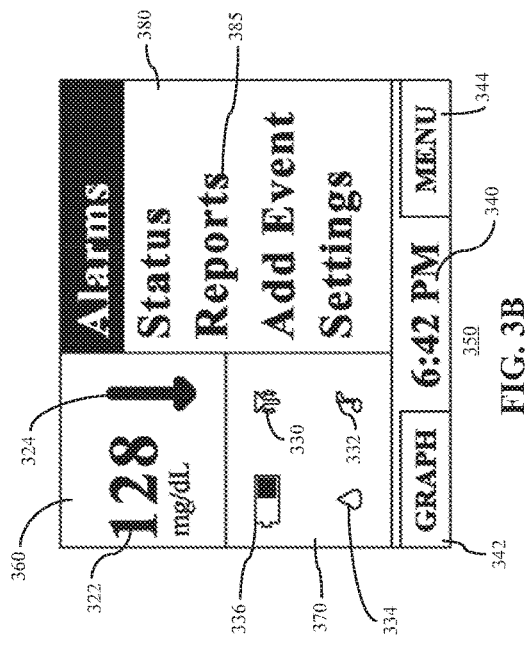
FIG. 3D
FIG. 3E

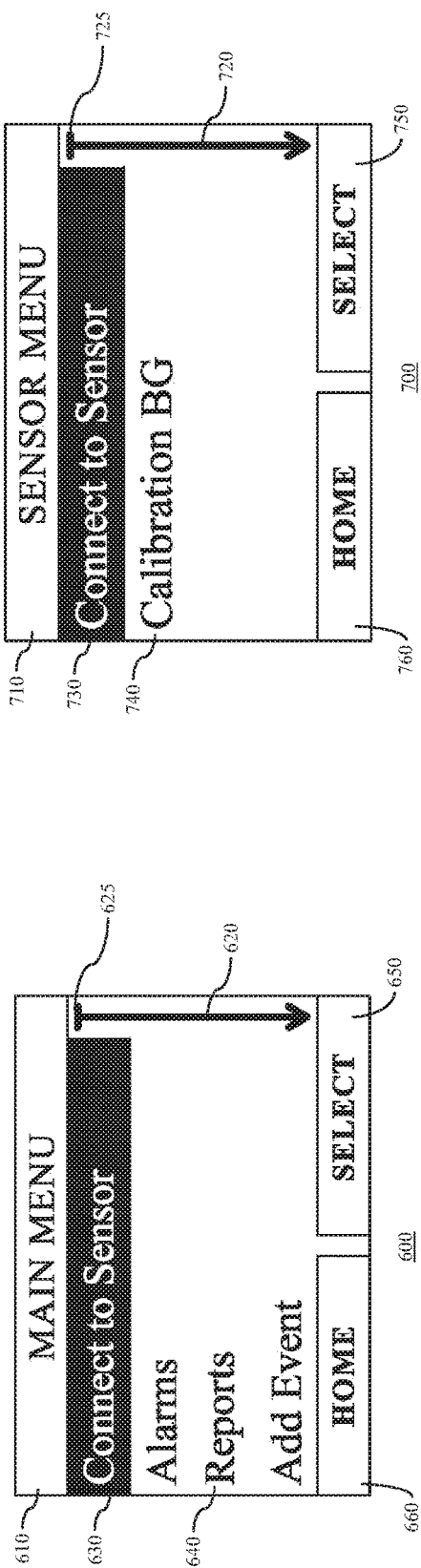
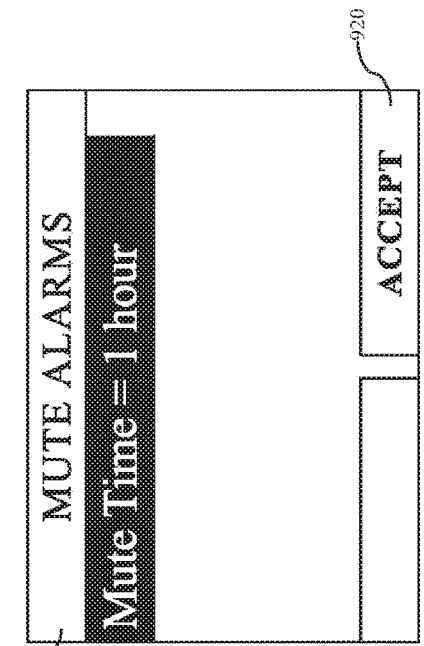
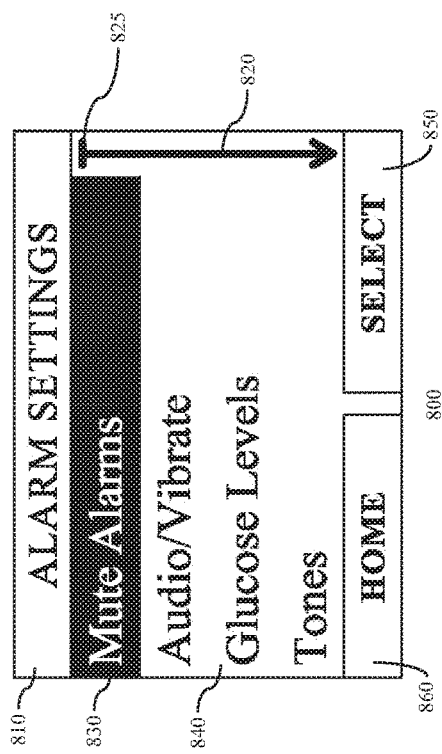
FIG. 6
FIG. 7
FIG. 8
FIG. 9

GLUCOSE ALARM

High
193 mg/dL
> 180 mg/dL

BOLUS | ACCEPT

FIG. 24B

BOLUS CALC

IOB = 0.0U
Correction = 2.1U
Total Bolus = 2.1U

NEXT

FIG. 24C

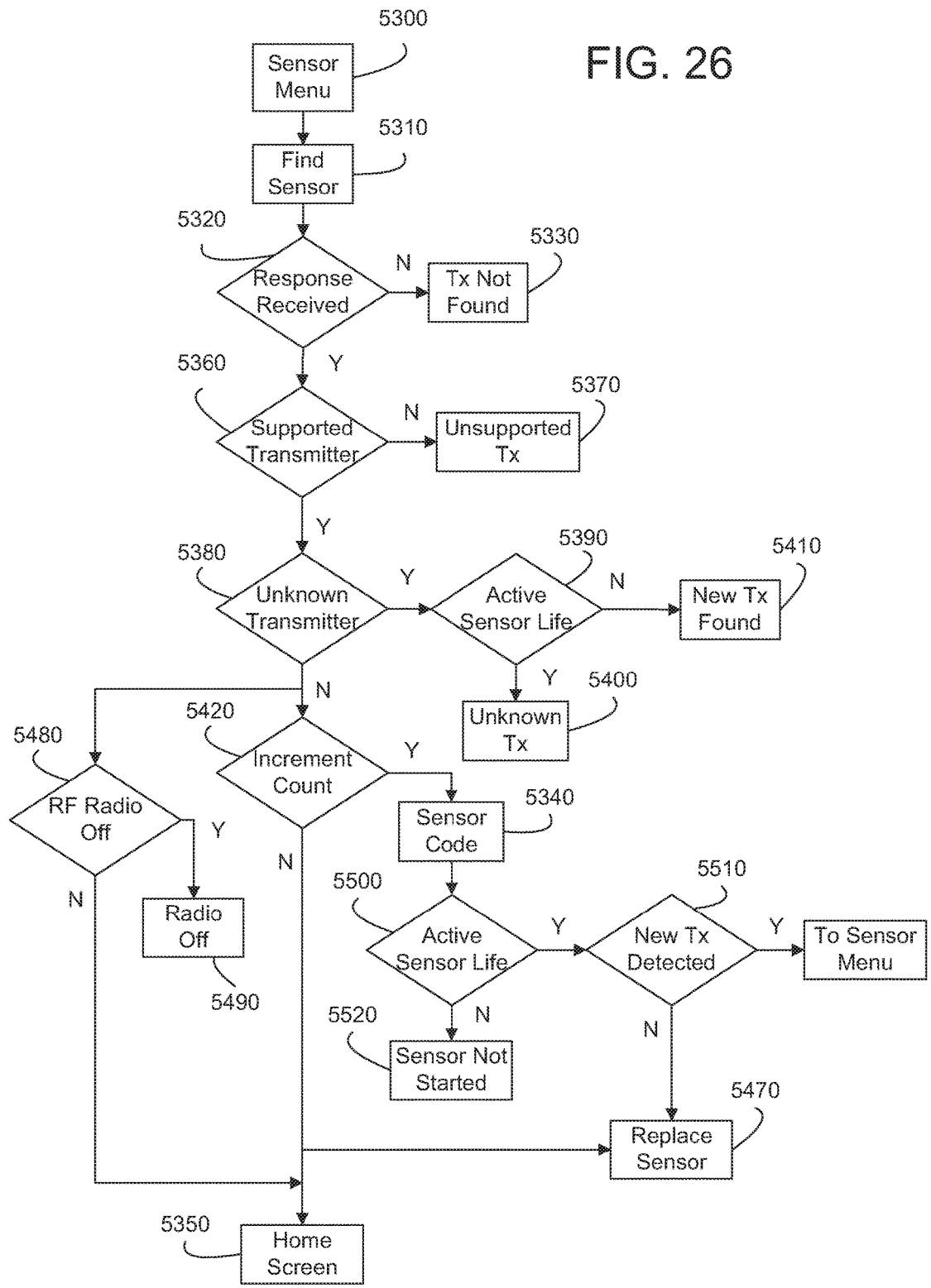

DISPLAYS FOR A MEDICAL DEVICE

RELATED APPLICATIONS

The present application is a continuation of U.S. patent application Ser. No. 15/377,989 filed Dec. 13, 2016, now U.S. Pat. No. 9,814,416, which is a continuation of U.S. patent application Ser. No. 14/938,840 filed Nov. 11, 2015, now U.S. Pat. No. 9,549,694, which is a continuation of U.S. patent application Ser. No. 14/457,066 filed Aug. 11, 2014, now U.S. Pat. No. 9,186,113, which is a continuation of U.S. patent application Ser. No. 13/970,556 filed Aug. 19, 2013, now U.S. Pat. No. 8,816,862, which is a continuation of U.S. patent application Ser. No. 12/871,901 filed Aug. 30, 2010, now U.S. Pat. No. 8,514,086, which claims to the benefit of U.S. Provisional Patent Application No. 61/238,672, entitled "Analyte Monitoring System Having a User Interface", filed on Aug. 31, 2009, U.S. Provisional Patent Application No. 61/238,657, entitled "Medical Device Having Illumination Assembly", filed on Aug. 31, 2009, U.S. Provisional Patent Application No. 61/247,541 entitled "Alarms For A Medical Device", filed on Sep. 30, 2009 and U.S. Provisional Patent Application No. 61/297,625, entitled "Displays for a Medical Device", filed on Jan. 22, 2010, the disclosures of each of which are incorporated herein by reference in their entirety for all purposes.

BACKGROUND

Diabetes mellitus is an incurable chronic disease in which the body does not produce or properly utilize insulin. Insulin is a hormone produced by the pancreas that regulates blood glucose. In particular, when blood glucose levels rise, e.g., after a meal, insulin lowers the blood glucose levels by facilitating blood glucose to move from the blood into the body cells. Thus, when the pancreas does not produce sufficient insulin, (a condition known as Type 1 Diabetes) or does not properly utilize insulin (a condition known as Type 2 Diabetes), the blood glucose remains in the blood resulting in hyperglycemia or abnormally high blood sugar levels.

People suffering from diabetes often experience long-term complications. Some of these complications include blindness, kidney failure, and nerve damage. Additionally, diabetes is a factor in accelerating cardiovascular diseases such as atherosclerosis (hardening of the arteries), which often leads to stroke, coronary heart disease, and other diseases which can be life threatening.

The severity of the complications caused by both persistent high glucose levels and blood glucose level fluctuations has provided the impetus to develop diabetes management systems and treatment plans. In this regard, diabetes management generally includes multiple daily testing of blood glucose levels by applying blood samples to test strips and analyzing the blood sample using a blood glucose meter. More recently, diabetes management has included continuous glucose monitoring systems. Glucose monitoring systems have the capability to continuously monitor a user's blood glucose fluctuations over a period of time and display the results to a user.

In such systems, it would be desirable to have a display and/or a user interface capable of robust, comprehensive information presentation, analysis, processing, user manipulation and/or usability features including, for example, programmable alarms and alerts, comprehensive visual, audible and/or vibratory output for assisting in diabetes management and improving glycemic control.

SUMMARY

Embodiments described herein relate to an analyte monitoring device having a user interface with a display and a plurality of actuators. The display is configured to output a plurality of display screens, including at least a home screen and an alert screen. The home screen is divided into a plurality of simultaneously displayed panels, with a first panel of the plurality of panels configured to display a rate of change of continuously monitored analyte levels in interstitial fluid, a second panel configured to simultaneously display a current analyte level and an analyte trend indicator, and a third panel configured to display status information of a plurality of components of the analyte monitoring device. When an alert condition is detected, an alert screen is output on the display in place of the home screen. The alert screen displays information corresponding to the detected alert condition. Furthermore, the plurality of actuators is configured to affect further output of the analyte monitoring device corresponding to the detected alert condition.

These and other objects, features and advantages of the present disclosure will become more fully apparent from the following detailed description of the embodiments, the appended claims and the accompanying drawings.

BRIEF DESCRIPTION OF THE DRAWINGS

FIGS. 3A-3C illustrate various home screen displays of a user interface of the analyte monitoring device according to embodiments of the present disclosure;

FIGS. 3D-3J illustrate exemplary trend indicator displays that may be used in conjunction with the home screen displays of FIGS. 3A-3C according to embodiments of the present disclosure;

FIG. 6 illustrates an exemplary menu screen according to embodiments of the present disclosure;

FIG. 7 illustrates an exemplary sensor menu screen according to embodiments of the present disclosure;

FIG. 8 illustrates an exemplary alarm settings menu screen according to embodiments of the present disclosure;

FIG. 9 illustrates an exemplary mute alarms menu screen according to embodiments of the present disclosure;

FIGS. 24B-24C illustrate additional exemplary alert screens according to embodiments of the present disclosure;

FIG. 26 illustrates an exemplary flow of a plurality of user interface screens according to embodiments of the present disclosure.

DETAILED DESCRIPTION

Figure 1:
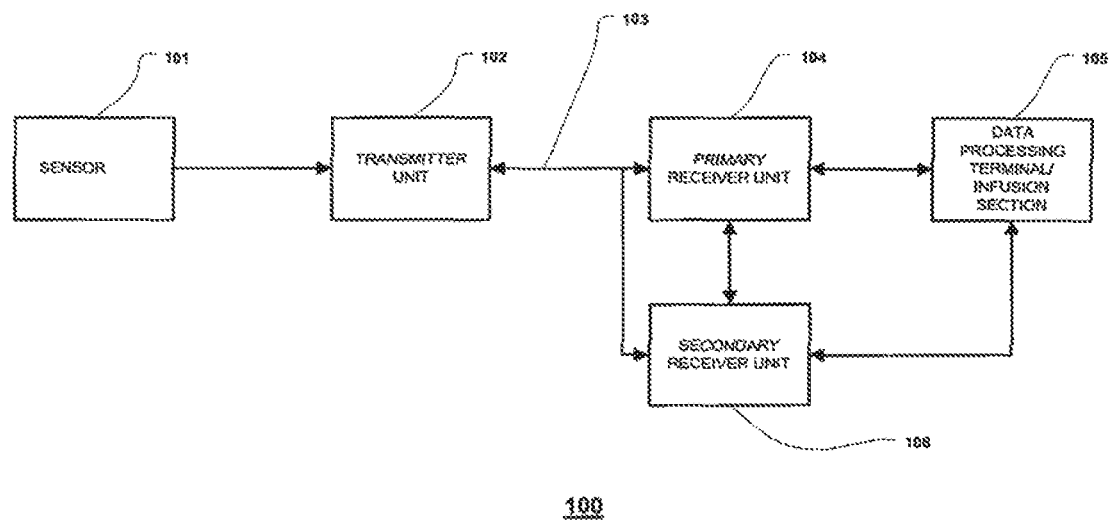
FIG. 1 illustrates a block diagram of a data monitoring and management system for practicing one or more embodiments of the present disclosure.

Before the present disclosure is described in detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Various exemplary embodiments of the analyte monitoring system and methods of the disclosure are described in further detail below. Although the disclosure is described primarily with respect to a glucose monitoring system, each aspect of the disclosure is not intended to be limited to the particular embodiment so described. Accordingly, it is to be understood that such description should not be construed to limit the scope of the disclosure, and it is to be understood that the analyte monitoring system can be configured to monitor a variety of analytes, as described below.

Embodiments described below relate to an analyte monitoring device having a user interface with a display and a plurality of actuators. The display is configured to output a plurality of display screens, including at least a home screen and an alert screen. In certain embodiments, the home screen is divided into a plurality of simultaneously displayed panels, with a first panel of the plurality of panels configured to display a rate of change of continuously monitored analyte levels in interstitial fluid, a second panel configured to simultaneously display a current analyte level and an analyte trend indicator, and a third panel configured to display status information of a plurality of components of the analyte monitoring device. In certain embodiments, when an alert condition is detected, an alert screen is output on the display in place of the home screen. The alert screen displays information corresponding to the detected alert condition. In certain embodiments, the plurality of actuators is configured to affect further output of the analyte monitoring device corresponding to the detected alert condition.

FIG. 1 illustrates a data monitoring and management system such as, for example, an analyte (e.g., glucose) monitoring system 100 in accordance with embodiments of the present disclosure. The analyte monitoring system 100 includes a sensor 101, a transmitter unit 102 coupleable to the sensor 101, and a primary receiver unit 104 which is configured to communicate with the transmitter unit 102 via a bi-directional communication link 103. The primary receiver unit 104 may be further configured to transmit data to a data processing terminal 105 for evaluating the data received by the primary receiver unit 104. Moreover, the data processing terminal 105 in one embodiment may be configured to receive data directly from the transmitter unit 102 via a communication link which may optionally be configured for bi-directional communication. Accordingly, transmitter unit 102 and/or receiver unit 104 may include a transceiver.

Also shown in FIG. 1 is an optional secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. The secondary receiver unit 106 may be configured for bidirectional wireless communication with each or one of the primary receiver unit 104 and the data processing terminal 105. In one embodiment of the present disclosure, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, pager, mobile phone, PDA, for example. Alternatively, the secondary receiver unit 106 may be configured with the same or substantially similar functionality as the primary receiver unit 104. The primary receiver unit 104 and/or secondary receiver unit 106 may be configured to be used in conjunction with a docking cradle unit for one or more of, for example, the following or other functions: placement by bedside, re-charging, data management, night time monitoring, and/or bidirectional communication.

In one aspect analyte monitoring system 100 may include two or more sensors, each configured to communicate with transmitter unit 102. Furthermore, while only one transmitter unit 102 and data processing terminal 105 are shown in the embodiment of the analyte monitoring system 100 illustrated in FIG. 1, it will be appreciated by one of ordinary skill in the art that the analyte monitoring system 100 may include one or more sensors, multiple transmitter units 102, communication links 103, and data processing terminals 105. Moreover, within the scope of the present disclosure, the analyte monitoring system 100 may be a continuous monitoring system, or semi-continuous, or a discrete monitoring system. In a multi-component environment, in certain embodiments, each device may be configured to be uniquely identified by each of the other devices in the system so that communication conflict is readily resolved between the various components within the analyte monitoring system 100.

In certain embodiments of the present disclosure, the sensor 101 is physically positioned in or on the body of a user whose analyte level is being monitored. The sensor 101 may be configured to continuously sample an analyte level of the user and convert the sampled analyte level into a corresponding data signal for transmission by the transmitter unit 102. In certain embodiments, the transmitter unit 102 may be physically coupled to the sensor 101 so that both devices are integrated in a single housing and positioned on the user's body. In certain embodiments, the transmitter unit 102 may perform data processing such as filtering and encoding data signals and/or other functions. Data signals received from sensor 101 correspond to a sampled analyte level of the user, and transmitter unit 102 may transmit the analyte information to, among others, the primary receiver unit 104 via the communication link 103. Additional detailed description of continuous analyte monitoring systems and various components including the functional descriptions of the transmitter are provided in, but not limited to, U.S. Pat. Nos. 6,134,461, 6,175,752, 6,121,611, 6,560,471, 6,746,582, and U.S. Patent Publication No. 2008/0278332 filed May 8, 2008 and elsewhere, the disclosures of each of which are incorporated by reference for all purposes.

Figure 2B:
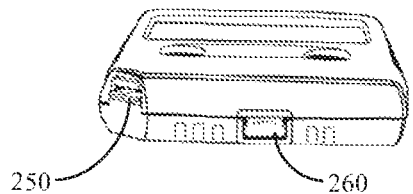
FIGS. 2A-2C illustrate an exemplary analyte monitoring device according to embodiments of the present disclosure.
Figure 2A:
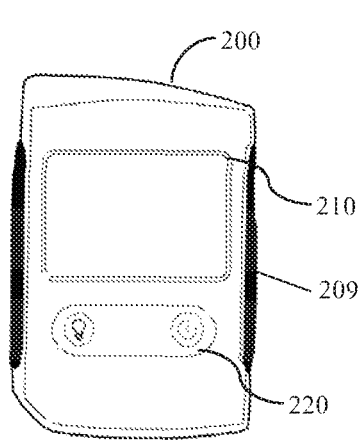
Figure 2C:
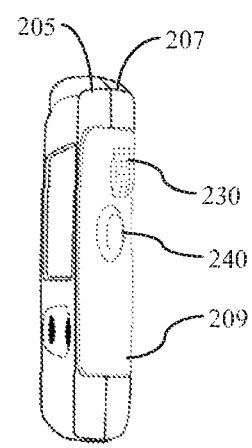

FIGS. 2A-2C illustrate an exemplary analyte monitoring device 200, such as the primary receiver 104 of analyte monitoring system 100 (FIG. 1) that may be used with certain embodiments of the present disclosure. In certain embodiments, the analyte monitoring device 200 is generally rectangular in shape and sized to fit in a single hand of a user. However, it is contemplated that the analyte monitoring device 200 may have various other shapes and sizes depending on, for example, a particular user or environment. For example, the analyte monitoring device 200 may have a first size and shape for an adult user, and a second size and shape for a child user.

The analyte monitoring device 200 comprises a front housing 205 and a back housing 207. In one aspect, each of the front housing 205 and the back housing 207 may be replaceable with housing covers having various colors and/or designs. In certain embodiments, the analyte monitoring device 200 may also include grip portions 209 disposed on lateral sides of the housing portions 205 and 207. The grip portions 209 may include a plurality of depressions or finger holds to provide a better grip to a user. Grip portions 209 may be made of rubber, plastic or other similar material that may increase a user's grip.

In certain embodiments, a user interface is disposed on the analyte monitoring device 200. As used herein, user interface refers to components that assist a user in interacting with the analyte monitoring device 200. Referring still to the Figures, the user interface may include a display 210 and a plurality of input buttons 220 on the front surface of the analyte monitoring device 200. Although two input buttons 220 are shown, it is contemplated that a keypad or keyboard may be disposed on the front surface of the analyte monitoring device 200 or only a single button or no buttons may be included. In certain embodiments, the user interface also includes a jog wheel 230 and a secondary button 240 disposed on one of the lateral sides of the analyte monitoring device 200. In certain embodiments, the user interface may also include a test strip port 250 for receiving an in vitro test strip and a data port 260, such as a USB or serial port. In certain embodiments, a sound system (not shown) may also be included with the user interface for outputting audible signals. The sound system may include a sound synthesizer (e.g., an OKI ML2871 sound generator) and at least one speaker (e.g., an eight ohm speaker). In certain embodiments, a vibratory system may be included and configured for outputting, among others, a vibratory or other tactile alert. Although specific components are mentioned, it is contemplated that the user interface may include fewer or additional components than those specifically discussed.

In certain embodiments, the display 210 is an organic light emitting diode (OLED) display. The OLED display may be configured with a display resolution and refresh or frame rate conducive to a clear output to the user. In one embodiment, the display may be a 160×128 pixel display with a frame rate of about 10.5 frames per second. In certain embodiments, the display may be higher resolution and/or refresh rate, including high definition (HD) output. Such a display 210, in aspects of the present disclosure, is configured to provide color output display. In other embodiments, the display 210 is a liquid crystal display (LCD). In other embodiments, the display is a plasma display. In certain embodiments, the display 210 is a touch sensitive display. The display 210 is used to display a plurality of graphical user interface screens or screen types (e.g. display screens) to a user as the user interacts with the analyte monitoring device 200. In certain embodiments, the display is configured to output still and video images.

In certain embodiments, a zoom-in and zoom-out feature is available for various display screens that are output on the display 210. The zoom-in and zoom-out feature may be used by actuating the jog wheel 230 either alone, or in combination with, a second button, such as secondary button 240 or one of the plurality of input buttons 220. The zoom-in and zoom-out feature enables a user to fully or partially display menu screens having a plurality of menu items, all of which may or may not be simultaneously displayed on the display 210. Further, the zoom-in and zoom-out feature can be used to focus in on a particular portion of a graph or other type of information that is displayed on display 210. In certain embodiments, the zoom-in and zoom-out feature may be used to zoom-in on a selected panel of a home screen such as will be described in greater detail below.

In certain embodiments, display 210 outputs display screens in an orientation that corresponds to the analyte monitoring device 200 being held in a vertical upright position. In one aspect, the analyte monitoring device 200 includes an accelerometer configured to detect an orientation at which the analyte monitoring device 200 is being held. Based on the detected direction, a control unit or processor of the analyte monitoring device 200 outputs display screens on the display 210 in an orientation that corresponds to the detected orientation of the analyte monitoring device 200. Thus, when the orientation of the analyte monitoring device 200 is changed, the orientation of the display screens on the display 210 is adjusted to conform to the new orientation. For example, if the analyte monitoring device 200 is in a vertical upright or portrait position, the display screens output on the display 210 are displayed in a vertical upright or portrait orientation. However, if the analyte monitoring device 200 is rotated 90 degrees, the display screens output on the display 210 will also rotate by 90 degrees in the same direction, at which point the display screens output on the display 210 will be shown in a landscape or horizontal orientation instead of a vertical upright or portrait orientation.

In certain embodiments, if the analyte monitoring device 200 is repeatedly rotated into a particular orientation for specific functionality, such as, for example, when performing a blood glucose test, or when a particular graph is displayed, the display screens corresponding to the specific functionality are output in an orientation that corresponds to the expected orientation of the analyte monitoring device 200. For example, if a user repeatedly holds the analyte monitoring device 200 in a particular orientation (e.g. horizontally on its side) when performing a blood glucose test, a processor of the analyte monitoring device 200 causes a blood glucose test display screen to be output on the display 210 in an orientation corresponding to the expected orientation of the analyte monitoring device 200 when input corresponding to a blood glucose test is received or detected. In certain embodiments, the detected input may correspond to user selected input on the user interface, such as, for example, selecting a blood glucose test menu item on a menu display screen or by inserting a test strip into the test strip port 250. In other embodiments, the orientation of the display screens may be altered based on various alarms and/or alert notifications.

The user interface of the analyte monitoring device 200 also includes a plurality of input buttons 220. In certain embodiments, at least one of the input buttons 220 is a power button and at least one input button 220 is used to activate and deactivate a light in the test strip port 250. As will be described in greater detail below, each input button 220 may also be used as a softkey button such that actuation of the input buttons 220 invoke functions described by text of a softkey button label shown on the display 210. Although two input buttons 220 are specifically shown, it is contemplated that fewer or additional input buttons 220 may be included on the user interface of the analyte monitoring device 200.

Each of the input buttons 220 may also be programmed by a user to invoke a number of different functions based on user preference. For example, actuation of one of the input buttons 220 may cause the analyte monitoring device 200 to enter a sleep mode. Other examples include controlling the volume of the analyte monitoring device 200 or turning wireless capabilities of the analyte monitoring device 200 on or off. The input buttons 220 may also be programmed by a user to act as a shortcut to a particular display screen (e.g., a timeline graph, CGM statistics screen etc.).

In certain embodiments, analyte monitoring device 200 also includes a jog wheel 230 and a secondary button 240 disposed on a lateral side. As used herein, a jog wheel refers to a physical scroll action control that has inputs of "up", "down" (e.g., scroll up and scroll down) and "select" (e.g., inward push of the jog wheel). In certain embodiments, jog wheel 230 may also include left and right scrolling action. Such functions could also be carried out by respective up and down buttons and a select button. Although a jog wheel is specifically mentioned, it is contemplated that other actuators, such as a ball or roller, may be used.

In certain embodiments, secondary button 240 is used as a "back" button to assist a user in navigating to various screen types and display screens of the user interface. In addition to enabling a user to navigate backwards through the display screens, the secondary button 240 may be used to cancel a change made to a user selectable value in the various display screens. In certain embodiments, when the user has navigated away from a home screen, actuation of the secondary button 240 for a predetermined amount of time (e.g. 5 seconds) returns a user to the home screen. In certain embodiments, the secondary button 240 is an additional softkey button that can be programmed for specific functionality, such as accessing a particular graph or display screen, based on user preference.

In certain embodiments, the analyte monitoring device 200 also includes a test strip port 250 and a data port 260. In certain embodiments, the test strip port 250 is used to receive a test strip to check a blood glucose level of a user and/or to calibrate a sensor, such as, for example, sensor 101 (FIG. 1). In certain embodiments, an illumination assembly disposed within the housing of the analyte monitoring device 200 is configured to illuminate the test strip port 250 of the analyte monitoring device 200.

Figure 2D:
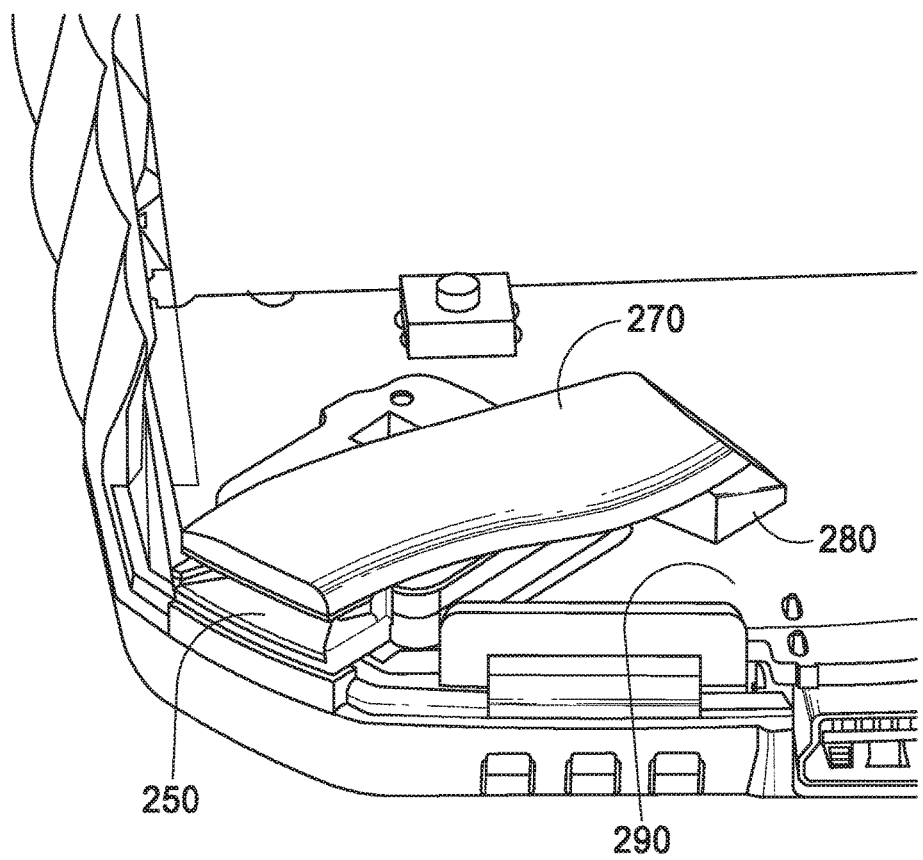
FIG. 2D illustrates an illumination assembly for the exemplary analyte monitoring device according to embodiments of the present disclosure.

Referring to FIG. 2D, the illumination assembly includes a light source 280, such as, for example, a light emitting diode (LED), OLED, incandescent light bulb, cold cathode fluorescent lamp (CCFL) or solid state laser, and a light pipe 270 configured to distribute light from the light source 280 to an opening in the test strip port 250 or various other areas of the analyte monitoring device 200. In one aspect, the illumination assembly may be configured to produce a plurality of colors. For example, the light source 280 may produce a white light and as the white light passes through the light pipe 270, various filters in the light pipe 270 may cause the white light to refract into various colors. Thus, a single light source 280 and light pipe 270 may be used to illuminate a plurality of areas of the analyte monitoring device 200 in various colors. For example, the light pipe 270 may be configured to illuminate a test strip port 250 of the analyte monitoring device 200 in a first color and illuminate one or more buttons, such as input buttons 220, disposed on the housing of the analyte monitoring device 200 in a second color. In another aspect, a plurality of light sources may be used with a single light pipe 270 in which each light source 280 emits a different color of light. In still yet another embodiment, a plurality of light pipes 270 may be used with a single or a plurality of light sources 280.

In certain embodiments, the light pipe 270 is a tubular or planar structure, formed from clear or colored plastic or glass. As shown in FIG. 2D, at least a portion of the light pipe 270 is placed over the light source 280 and is configured to distribute light from the light source 280 to a test site or entry port of the test strip port 250. Although a test site and an entry port are specifically mentioned, it is also contemplated that the light pipe 270 may be used to illuminate an indicator icon, a keypad, and/or one or more buttons (e.g., input buttons 220, jog wheel 230, secondary button 240, etc.) disposed on the analyte monitoring device 200. In yet another embodiment, portions of the housing of the analyte monitoring device 200 may be transparent or be formed from one or more light pipes thereby enabling portions of the housing of the analyte monitoring device to be illuminated by the light source 280.

In certain embodiments, the light pipe 270 includes a first end that is secured on or over the light source 280. In another embodiment, the first end of the light pipe 270 is secured to an area proximate the light source 280. The light pipe 270 has a length that extends from the first end to a second end. In certain embodiments, the second end of the light pipe is an entry port of the test strip port 250. Thus, when the light source 280 is activated, light is emitted through the light pipe 270 to the test site.

In one aspect, the second end of the light pipe 270 has an opening through which a test strip may be inserted. As such, the second end may be shaped so as to assist a user in inserting a test strip. For example, the opening of the second end of the light pipe 270 may be tapered so as to allow the test strip to be initially inserted into the opening of the light pipe 270 with relative ease.

It is contemplated that the light pipe 270 may have various shapes, sizes, and transparencies with each shape, size and transparency affecting the shape and strength of light emitted from the light pipe 270. For example, depending on the shape of the light pipe 270, a "flashlight" effect may be produced whereby a test site or test strip is illuminated with a bright beam of light. In certain embodiments, the light pipe 270 may include sharp prismatic type folds from which light from the light source 280 is reflected. Further, a reflecting surface may be included in the light pipe 270 to increase the efficiency of light transmission down the length of the light pipe 270. Examples include a metalized surface or a coating on one or more prism faces or intermediate faces of the light pipe 270 to increase the internal reflection. In one aspect, the light pipe 270, or portions thereof (e.g., the first end or the second end) may be configured in a convex or concave shape. In yet another aspect the light pipe 270 may have a roughened (e.g., pitted) surface to create a light dispersion effect.

In certain embodiments, the light pipe 270 may be used to provide various aesthetics to the analyte monitoring device 200, such as, for example, providing shape, color, and lighting to the overall design of the analyte monitoring device 200. For example, the light pipe 270 can provide an illuminated icon or a distinctive design element such as, for example, a trademark, or a model or brand of the analyte monitoring device 200. Further, and as described above, one or more light pipes 270 may be used as part of the overall design of the analyte monitoring device 200.

In certain embodiments, the light source 280 is at least partially disposed on a top or bottom portion of the housing of the analyte monitoring device 200. In another embodiment, the light source 280 is at least partially disposed on a printed circuit board 290 contained within the housing of the analyte monitoring device 200. In certain embodiments, the analyte monitoring device 200 contains only a single printed circuit board that supports and connects all of the electronic components of the analyte monitoring device 200 including the light source 280. In certain embodiments, because the light pipe 270 distributes light from the light source 280, additional printed circuit boards are not required to illuminate various portions or areas of the housing of the analyte monitoring device 200. Thus, as multiple printed circuit boards are not required, the overall reliability of the analyte monitoring device 200 is increased as inter-board connections between multiple printed circuit boards are also not required. Further, in certain embodiments, the light pipe 270 may be used as part of the housing and substantially, if not entirely, close portions of the housing of the analyte monitoring device 200 that would otherwise be open if light pipes 270 were not used to permit the light from the light source 280 to be emitted from the housing. As such, the light pipe 270 also functions to protect the inner circuitry of the analyte monitoring device 200 from moisture, dust and other contaminants.

In certain embodiments, the light source 280 is controlled by user activation of one or more of the input buttons 220 or secondary button 240. In one aspect, the option to turn the light source 280 on or off is only available when a test strip has been inserted into the test strip port 250. In another embodiment, the light source 280 may be turned on or off only when the display 210 has an active display screen and one of the input buttons 220 is depressed for a predetermined amount of time (e.g., 2 seconds). In still yet another embodiment, the light source 280 is automatically activated when a test strip is correctly inserted into the test strip port 250. It is also contemplated that an audible alert or tactile notification may be output when the test strip has been correctly inserted into the test strip port 250. Additionally, a warning light and/or an audible notification may be output by the analyte monitoring device 200 if the test strip is incorrectly inserted into the test strip port 250. For example, in certain embodiments, when the test strip is correctly inserted into the test strip port 250, a control unit or processor of the analyte monitoring device 200 causes a first light source to emit a first color and a first audible alarm and/or tactile notification may simultaneously be output. When the test strip is incorrectly inserted into the test strip port 250, a control unit or processor of the analyte monitoring device 200 causes a second light source to emit a second color (e.g., a red warning light) and a second audible alarm and/or second tactile notification may be output.

In certain embodiments, when the light source 280 has been actuated, such as, for example, when a test strip has been inserted into the test strip port 250 or in response to user actuation of an input button 220, the light remains on for a predetermined amount of time (e.g., 2 minutes or 1 minute or 30 seconds). When the time period expires, a processor of the analyte monitoring device causes the light source 280 to turn off. In another embodiment, the light source 280 is turned off only in response to a user removing the test strip from the test strip port 250 or when a user actuates one of the input buttons 220.

In certain embodiments, in addition to a light source 280 being actuated, the display screen on the display 210 may change from a home screen to a user instruction screen when the test strip is inserted into the test strip port 250. In certain embodiments, the user instruction screen is output on the display 210 if a blood sample or control solution cannot be detected on the test strip when the test strip is inserted into the test strip port 250. In certain embodiments, the user instruction screen instructs the user on how to proceed with a blood glucose test or a control solution test. In certain embodiments, for example, an icon, graphic, series of graphics, animation, video and/or text instructing a user to apply a blood sample or a control solution to the test strip after the test strip has been inserted may be output on the display 210. In another embodiment, audible voice instructions may be provided along with the instruction screen to instruct the user on how to proceed with the blood glucose test or control solution test.

In certain embodiments, while the test is being performed, an icon, such as a circle comprised of four arrows (or another icon), may be output on the display 210 and/or progress tones may be output to notify the user that the blood glucose test is ongoing. In certain embodiments, the user may input additional information into the analyte monitoring device 200 using, for example, an input button 220, corresponding to whether a control solution was used or whether a blood sample was used on the test strip. When the blood glucose test is complete, the test results are output on the display 210. For example, if the user performs a blood glucose test and the user's blood glucose level is either lower than 20 mg/dL (or other predetermined threshold) or higher than 500 mg/dL (or other predetermined threshold), a "Low" or a "High" indication is displayed. These results could indicate that the user is either in a hypoglycemic state or a hyperglycemic state or a hypoglycemic or hyperglycemic state is impending. In such cases, in certain embodiments, an alert screen may be output on the display 210 in which it is recommended that the user contact a healthcare professional or take corrective action, such as carbohydrate ingestion or taking medication, such as insulin.

In certain embodiments, data port 260 is a standard mini-USB port that may be used to charge a battery or other power source of the analyte monitoring device 200. Data port 260 may also be used to upload data stored in a memory or other storage medium of the analyte monitoring device 200 to a personal computer or secondary receiver. The stored data may correspond to settings of the analyte monitoring device 200, or historical data such as blood glucose levels, continuously monitored glucose levels etc. Data port 260 may also be used to download data from a server or other computing device, such as software upgrades, additional glucose alarm and notification tones including music, firmware upgrades and the like to the storage medium of the analyte monitoring device 200. When such updates are needed or finished, an alert screen may be output on the display 210 of the analyte monitoring device 200 informing a user of a needed action (e.g., software upgrades available) or a completed action (e.g., download of additional tones is complete).

In certain embodiments, when a cable is inserted into the data port 260, such as a USB cable for a USB data port, for charging the analyte monitoring device and/or uploading data to/from the analyte monitoring device 200, a cover is provided over the test strip port 250 to prevent a user from performing a blood glucose test when the analyte monitoring device 200 is connected to a power source. In one aspect, the cover may be part of the USB cable. In another aspect, the cover may be part of the housing of the analyte monitoring device 200. As such, when the cable is inserted into the data port 260, the cover slides in front of and closes the test strip port 250. When the cable has been removed from the data port 260, the cover is retracted into the housing of the analyte monitoring device 200 and the test strip port 250 is accessible.

In certain embodiments, the analyte monitoring device is configured to output an audible alarm, a tactile alarm, a visual alert or a combination thereof when a test strip is inserted into the test strip port 250 while the analyte monitoring device 200 is connected to an external device or power supply (e.g., to charge a rechargeable battery of the analyte monitoring device 200 and/or to transfer data between the analyte monitoring device 200 and a remote computer). In such embodiments, a processor of the analyte monitoring device 200 is configured to detect when the analyte monitoring device 200 is physically connected (e.g., through a data cable, such as a USB or mini USB cable connected to the data port 260) to an external device or power supply. In certain embodiments, the processor is also configured to detect when a test strip has been inserted into the test strip port 250. As such, when a test strip has been inserted into the test strip port 250, the processor is configured to issue a command to determine whether the analyte monitoring device 200 is, at the time of the insertion of the test strip, physically connected to an external device or power supply. If the analyte monitoring device 200 is connected to an external device or power supply, the processor issues a command to output the alert.

In one aspect the visual alert corresponds to an alarm screen such as will be described in detail below, in which the user is visually notified that the analyte monitoring device 200 will not measure blood glucose values when the analyte monitoring device 200 is physically connected to an electronic device or a power source. In another aspect the visual alert may be a warning light emitted from the illumination assembly of the analyte monitoring device. In certain embodiments, upon detection of a test strip insertion into the test strip port 250, analyte monitoring device 200 may be configured to electrically isolate data port 250.

In certain embodiments, various screen types are output on the display 210 of the analyte monitoring device 200. Each screen type provides different functionality, prompts and information to a user. Examples include menu screen types and informational screen types. In certain embodiments, informational screen types include a plurality of display screens organized into a hierarchy of display screens. The display screens of the informational screen types typically, but not necessarily, show graphs, connection status, alerts, warnings, and the like. In certain embodiments, when informational screen type alerts, warnings or prompts are displayed, a processor of the analyte monitoring device 200 causes an alarm to be output if the alert is not acknowledged within a predetermined amount of time (e.g. 1 hour). In certain embodiments, menu screen types include menus having selectable menu items. Because the display screens are hierarchically arranged, upon selection of a menu item, the display screens linearly progress to various functions represented by the menu item (e.g., by actuation of a softkey button corresponding to a "Next" softkey label), additional display screens or further submenus. Although specific screen types have been mentioned and will be described in further detail below, it is contemplated that various other screen types may be included in the user interface of analyte monitoring device 200.

FIG. 3A illustrates an information mode home screen 300 according to embodiments of the present disclosure. Referring to FIG. 3A, the information mode home screen 300 includes a plurality of panels or sections. In certain embodiments, the panels are distinct from one another and the information. Thus, what is displayed in one panel may not necessarily affect what is displayed in a second panel. Furthermore, each panel or section may display different types of data to a user and the data in each panel is dynamically updated. For example, one panel may display user state information while a second panel simultaneously displays system state information. Further, as information is received, such as, for example, continuous glucose data from the sensor 101 (FIG. 1), the information displayed in the panels is updated to display the newly received data. In certain embodiments, each panel is selectable. When a panel is selected, such as, for example, using the jog wheel 230 (FIG. 2C) to highlight a particular panel or by user actuation of an input button 220 or touch screen portion of the display 210, a user may zoom in on the information displayed in the panel or select that the particular panel be displayed on the entire area of the display 210. Furthermore, each of the panels may be sizable with respect to other panels. Thus, a user may select that one panel have a first size while a second panel have a second size relative to the first panel. In another embodiment, the panels can be arranged in different positions relative to one another based on user preference.

In certain embodiments, user state information includes information corresponding to analyte levels such as, for example, glucose levels, rate of change of an analyte level, bolus insulin doses, meals, exercise periods and other user related activities. This information may be represented as text, numbers, graphics, icons, animations, video, or combinations thereof.

In certain embodiments, system state information includes information corresponding to the status of various components of the analyte monitoring system 100 (FIG. 1) or the analyte monitoring device 200. Such information may include sensor status, calibration status, transmitter power status, alarm status, and battery status, among others. System state information may be represented as text, numbers, graphics, icons, animations, video, or combinations thereof.

In certain embodiments, various color schemes are used to convey a severity of a condition that the system state information and the user state information represent. As will be described in greater detail below, if for example, a numerical display of a current glucose value is output on the user state information panel, the number may be shown in purple to indicate that the user's current glucose level is above a predetermined glucose threshold. If however, the number representing the current glucose value displayed is green, the user's current glucose level is within the predetermined glucose threshold. While specific displays and colors are described, it is contemplated that any combination of displays and colors may be utilized.

Referring back to FIG. 3A, information mode home screen 300 includes a number of panels with each panel displaying a different type of data. A first panel 303 shows a user's historical analyte data, such as, for example, continuous glucose levels. This data may be represented as a graph 305. As new data is received, such as, for example, glucose data from the sensor 101 (FIG. 1), the graph 305 is dynamically updated such that the newly received glucose data is displayed on the graph 305. Although graph 305 is depicted as a line graph, it is contemplated various other types of graphs may be used including bar graphs, pie charts etc. Graph 305 includes a graph line 310 that represents continuous glucose readings taken over a time t. Graph 310 also includes lower glucose target indicator 312 and an upper glucose target indicator 314. In certain embodiments, the graph 305 includes a range of numbers corresponding to glucose levels. FIG. 3A illustrates a range of from 40 mg/dL to 280 mg/dL on the y-axis with tick marks 316 at 40 mg/dL, 100 mg/dL, 160 mg/dL, 200 mg/dL, and 280 mg/dL respectively, however, any suitable range may be used. The graph 305 may also be configured to display a range of numbers in various units of measure. For example, graph 305 may display a range on the y-axis from 2 mMol/L to 16 mMol/L with tick marks at 2 mMol/L, 6 mMol/L, 8 mMol/L, 12 mMol/L, and 16 mMol/L respectively.

In certain embodiments, the graph line 310 indicates historical analyte data, such as, continuous glucose readings. The graph line 310 of the graph 305 may show up to 288 or more of the most recently logged continuous glucose readings. In certain embodiments, more or less recently logged readings may be displayed. In certain embodiments, the number of recently logged readings to display may be user selectable. In certain embodiments, the graph line 310 is displayed in a particular color so as to enable the user to easily distinguish the graph line 310 from other icons or lines on the graph 305. In another embodiment, various portions of graph line 310 may be displayed in multiple colors. For example, when the graph line 310 is within the bounds set by lower glucose target indicator 312 and upper glucose target indicator 314, the graph line 310 is white. However, when the graph line 310 exceeds the threshold levels set by the glucose target indicators 312 and 314, the portion of the graph line 310 that falls outside the target indicators 312 and 314 is displayed as a second color. In one aspect, if the graph line 310 falls outside the target indicators 312 and 314 the entire graph line 310 is displayed in a different color (e.g., purple). As will be explained in greater detail below, when the graph line 310 exceeds a threshold level, an alarm icon may be displayed on the graph 305 to indicate that an alarm was output when the user's analyte level exceeded the threshold level.

In certain embodiments, a threshold value is exceeded if a data point, such as a glucose reading, has a value that falls outside of the threshold values. Data points that exceed the threshold could indicate an impending condition, such as impending hyperglycemia or impending hypoglycemia, or a particular present condition, such as hypoglycemia or hyperglycemia. For the purpose of illustration, when a data point on the graph line 310 corresponds to a glucose level of 200 mg/dL and the selected upper threshold value 314 is 180 mg/dL, this could indicate that the monitored user has entered a hyperglycemic state. However, when a data point on the graph line 310 corresponds to a glucose level of 65 mg/dL and the selected lower threshold value 312 is 70 mg/dL, this could indicate that the monitored user has entered a hypoglycemic state.

Referring still to FIG. 3A, lower glucose target indicator 312 and upper glucose target indicator 314 may be represented as horizontal lines and displayed in a different color than the color of the graph line 310. Although solid lines are shown, it is contemplated that dashed lines or other indicators may be used to designate the lower glucose target indicator 312 and the upper glucose target indicator 314. As will be explained in greater detail below, the values corresponding to the lower glucose target indicator 312 and the upper glucose target indicator 314 may be changed by a user. In another embodiment, the values of the lower glucose target indicator 312 and the upper glucose target indicator 314 may only be changed by a healthcare professional. In such cases, a menu screen allowing a user to change the lower glucose target indicator 312 and the upper glucose target indicator 314 may be locked and/or password protected to prevent a user from changing the threshold range values without permission or authorization from a healthcare professional, parent or guardian.

In certain embodiments, graph 305 includes event data icons 318 (FIG. 3C). The event data icons 318 are displayed on the graph line 310 at the time the event takes place. In certain embodiments, up to twenty of the most recent events can be displayed on the graph 305 at a single time. Thus, a user may readily identify a glucose level at the time the event took place and how the event affected the user's glucose level. Such events may include discrete blood glucose measurements, insulin dosing, exercise periods, meal times, state of health, and the like. Graph 305 may also display alarm icons that indicate when particular alarms, such as a high glucose threshold alarm, a low glucose threshold alarm, a projected high glucose alarm, and a projected low glucose alarm, were output by the analyte monitoring device 200. In certain embodiments, a user may create custom events and select icons, text or other indicator for each custom event. An exemplary graph having custom event indicators 401 is shown in FIG. 4E. It is contemplated that a user may select distinguishing icons for each event, or class of events.

In certain embodiments, when an event icon 318 is displayed on the graph 305, a user may select a particular event represented by the event data icon 318. Upon selection of the event, a display screen is output displaying details corresponding to the selected event. In one aspect, the selection of the event may be made using a touch screen or actuation of a softkey button, such as one of input buttons 220 (FIG. 2A), or by actuating the jog wheel 230 (FIG. 2C).

In certain embodiments, a second panel 320 of the information mode home screen 300 is configured to simultaneously display glucose information 322 and a trend information icon 324. The glucose information 322 may be numerically displayed and represent continuous glucose data received from the sensor 101 via the transmitter unit 102. In one aspect, as glucose data is received from the sensor 101, the glucose information 322 is dynamically updated to show the most recent glucose readings. In certain embodiments, the glucose information 322 is color coded to indicate whether the current glucose levels are within predetermined threshold levels. For example, the glucose information 322 may be displayed in green to indicate that the current glucose level of the user is within a predetermined glucose threshold level. If however, the glucose information 322 is displayed in purple or yellow, the current glucose level is above or below the predetermined threshold level. Although specific color combinations have been discussed, it is contemplated that other color combinations may be used and/or selected by a user.

In certain embodiments, fluctuations caused by noise, outlying data points, insignificant analyte changes and lag spikes are not displayed on either the first panel 303 or the second panel 320 of the information mode home screen 300. In certain embodiments, "sticky" analyte values may be used to ensure that the fluctuations are not displayed in either the glucose information icon 322 and/or the trend information icon 324. For example, when a first new analyte level value is received from a sensor, such as for example from sensor 101 (FIG. 1) via a transmitter unit 102, and the new value is higher than a sticky analyte value, the sticky analyte value is displayed. When a second new analyte value is received, the second new analyte value is compared to the sticky analyte value. If the second new analyte value is also higher than the sticky analyte value, the second new analyte value becomes the new sticky analyte value and the second new analyte value is output on the display 210 and/or used to calculate the rate of change. If the second new analyte value is lower than the sticky analyte value, the current sticky value is maintained and displayed.

For example, if the most recently received analyte value is 99 mg/dL and the first new analyte value is 102 mg/dL, the previously received analyte value (e.g., 99 mg/dL) is designated as the sticky value and is output on the display 210. If the next analyte value received is also greater than 99 mg/dL (e.g., 101 mg/dL) the second new analyte value is displayed in place of the sticky analyte value (e.g. 99 mg/dL). However, if the second new value is less than 99 mg/dL, the sticky value is not replaced.

In certain embodiments, if the received analyte values continue to move in the same direction (e.g. the analyte values increase or decrease) over a predetermined amount of time (e.g. 3 minutes), each new analyte value that is received is displayed as it is received. In certain embodiments, each new analyte value that is received is displayed and replaced by a subsequent analyte value until the readings stabilize (e.g., the rate of change of the analyte levels is within a predetermined threshold) for a predetermined amount of time (e.g. 5 minutes). Once the analyte readings stabilize, the use of sticky values may be implemented once again. Although the example above specifically illustrates situations in which the received analyte level is higher than the sticky value, it is contemplated that sticky values may be set for analyte readings that are lower than the sticky analyte value in the same way.

In certain embodiments, a dead zone, or threshold, may be created around the sticky analyte value. In such cases, the displayed analyte value does not change until the newly received value is outside of the dead zone. In certain embodiments, the dead zone boundary is defined by a percentage of change of the sticky analyte value or a range of the change of the received analyte level value. For example, if the sticky analyte value is 99 mg/dL, the dead zone may be defined as +/−4 mg/dL. Thus, the range of the dead zone is between 95 mg/dL and 103 mg/dL. If the received analyte value is 102 mg/dL, the received analyte value is not displayed because the received analyte value is within the dead zone. However, if a subsequent analyte value is received which is outside the dead zone, for example, 104 mg/dL, the subsequent analyte value is displayed and the dead zone resets. Thus, the new dead zone is between 100 mg/dL and 108 mg/dL. In certain embodiments, the dead zone remains constant. Thus, regardless of the sticky analyte value, the range of change remains constant (e.g., +/−4 mg/dL). In another embodiment, the dead zone may be computed based on detected noise from a sensor or fluctuations of the glucose value.

In certain embodiments, changes in analyte values that fall outside a predetermined range (e.g. +/−3 mg/dL) are the only analyte values output on the display 210. For example, if analyte values of 90 mg/dL, 98 mg/dL, 102 mg/dL, 100 mg/dL, 99 mg/dL, and 101 mg/dL, are received at the analyte monitoring device 200 and the predetermined range is +/−3 mg/dL, analyte values of 90 mg/dL, 98 mg/dL, 102 mg/dL, 102 mg/dL, 102 mg/dL, and 102 mg/dL are output on the display 210 because not all of the received analyte values exceed the predetermined range.

In certain embodiments, a limit on the rate of change of the analyte data may be imposed. For example, the rate of change in the analyte value may be limited to some maximum value, such as, for example, +/−4 mg/dL per minute. If the rate of change of received analyte values exceeds the maximum value, the received analyte value is an outlying data point and will not be output on the display. While specific dead zone and other ranges are described, it is contemplated that other applicable range values may be used.

Returning to FIG. 3A, in certain embodiments, visual, tactile and/or auditory alarms may be used in conjunction with the data that is output on the second panel 320. For example, when the current glucose level is above or below a target level, an alert may be output and the panel containing the glucose information 322 is enlarged so as to be displayed on all, or substantially all, of the display 210 (FIG. 2A). The text of the glucose information 322 may be color coded based on a severity of the condition or color coded depending on a detected event that triggered the alarm. For example, if the current glucose level is above a predetermine threshold, when the panel expands, the text indicating the current glucose level of the user displayed in the panel is purple. In another embodiment, a processor or control unit of the analyte monitoring device 200 may cause a tactile and/or audible alarm to be output to notify the user that their current glucose level has exceeded a threshold. If the user disregards the alarm, or uses a "snooze" feature, the alarm is output a second time after a predetermined or user selected amount of time has elapsed. In certain embodiments, if an alarm is unheeded by the user for a substantial period of time, the alarm may increase in volume or pitch or change tone, or an alarm on a secondary analyte monitoring device or an alarm on a computing device capable of wirelessly communicating with the analyte monitoring device 200 may be output.

Referring back to FIG. 3A, in certain embodiments, the second panel 320 also includes a trend information icon 324. The trend information icon 324 indicates a rate of change of a user's glucose level and the direction of the change. For example, a substantially horizontal trend arrow indicates glucose is changing gradually (e.g., less than 1 mg/dL per minute), a diagonally downward arrow indicates glucose is decreasing moderately (e.g., between 1 and 2 mg/dL per minute), a straight downward arrow indicates glucose is decreasing rapidly (e.g., more than 2 mg/dL per minute), a diagonally upward arrow indicates glucose is increasing moderately (e.g., between 1 and 2 mg/dL per minute) and a straight upward arrow indicates glucose is increasing rapidly (e.g., more than 2 mg/dL per minute). In certain embodiments, the trend information icon 324 is dynamically updated based on data received from the sensor 101. Additionally, in certain embodiments, the trend information icon 324 is color coded based on a rate of change. For example, the straight upward arrow may be displayed in red to indicate a rapid increase in the user's glucose levels while the horizontal arrow may be displayed in green to indicate that the user's glucose levels are stable or are only gradually changing.

Figure 3F:
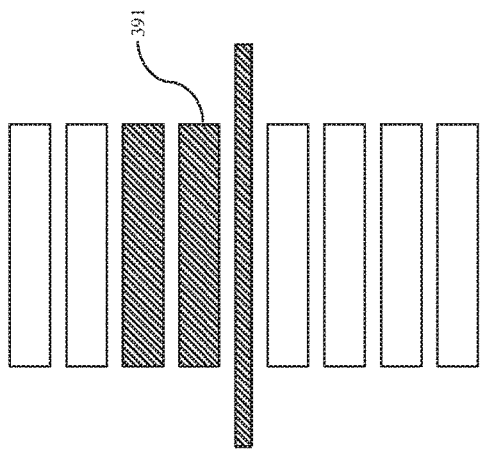
Figure 3G:
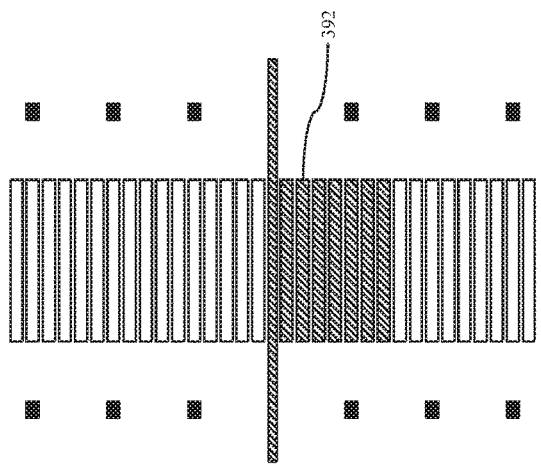
Figure 3H:
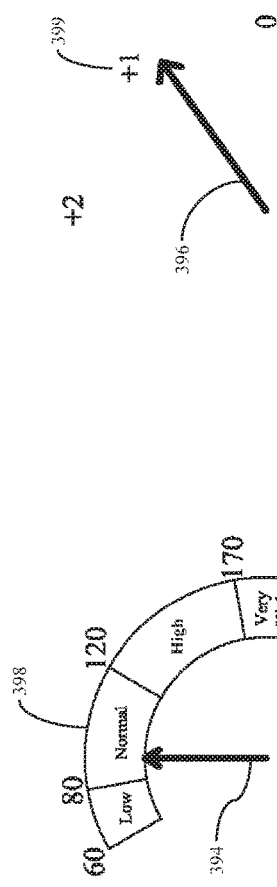
Figure 3I:
Figure 4C:
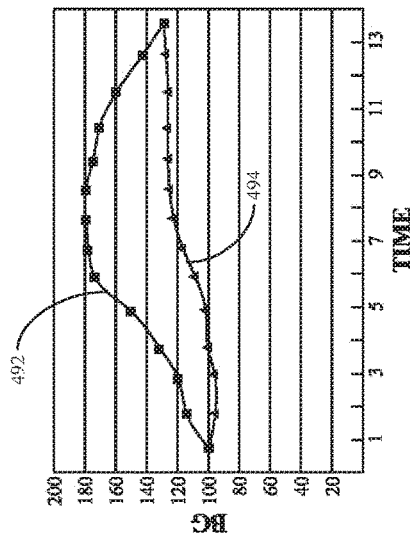
FIGS. 4A-4F illustrate display screens showing timeline graphs according to embodiments of the present disclosure.
Figure 4D:
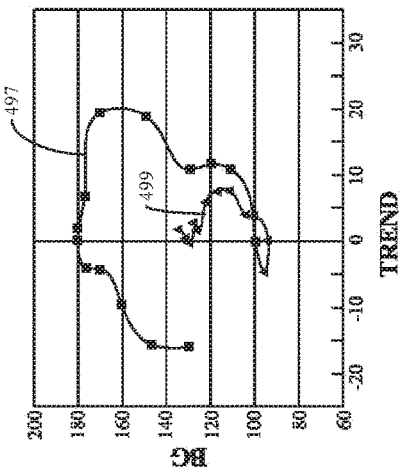

Although an arrow is specifically described and shown in FIG. 3A, it is contemplated that other icons, text, or graphics may be used to indicate glucose trends. Such examples include, but are not limited to trend indicator displays such as shown in FIGS. 3D-3E, in which arrows 386 and 387 point to a plurality of indicator positions 388 and 389 that correspond to rates of change of a glucose level, thermometer type graphs such as shown in FIGS. 3F-3G, in which indicator bars 391 and 392 of the graph change color based on the rate of change of the glucose level (e.g., the more bars that are filled indicate a greater rate of change), and speedometer type graphs such as shown in FIGS. 3H-3I, in which indicators 394 and 396 move continuously between regions 398 or tick marks 399 of the graph with each region 398 or tick mark 399 representing a rate of change. In one aspect, a user may select any of the above indicators to be output on the display based on user preference. It is also contemplated that each indicator described above may be color coded based on severity of the rate of change and/or on user preference.

Figure 3J:
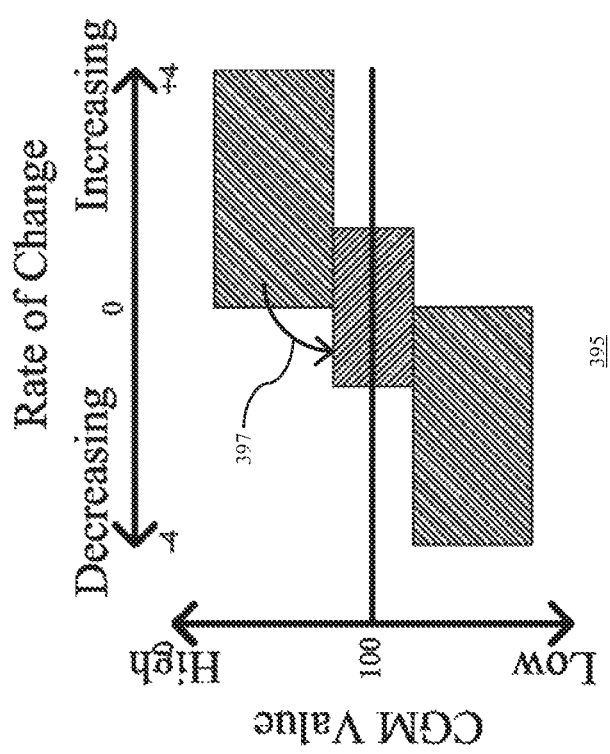

FIG. 3J illustrates a graphical display screen 395 showing measured analyte levels plotted against a rate of change of analyte levels according to embodiments of the present disclosure. In certain embodiments, the graphical display screen 395 is included as a panel of a home screen such as information mode home screen 300. In another embodiment, the graphical display screen 395 is a display screen that is output based on user settings, user navigation to the graphical display screen 395 or user actuation of an input button 220.

As shown in FIG. 3J, the graphical display screen 395 includes a line 397 that indicates historic recorded analyte levels over a period of time with the most recent analyte level represented by an arrowhead. Although an arrowhead is shown on the line 397, the arrowhead is optional and other icons or markers may be used to indicate a most recent analyte level reading. In certain embodiments, the length of time represented by the line 397 is configurable by the user. As the monitored length of time is adjusted by the user, the length of the line is also adjusted accordingly. For example, to highlight the recent changes in the analyte level to assist a user in making medication dosing decisions, the user may specify a short time range and thus, a short line 397 is displayed on the graphical display screen 395. Using the graphical display screen 395, a user can visually distinguish between a high analyte level that is increasing (e.g. the line 397 is trending toward the upper right quadrant) versus a high analyte level that is decreasing (e.g., the line is trending downward from the upper left quadrant).

In certain embodiments, the user may specify a long time range. Thus, if a user's analyte levels remain constant or substantially constant, the line 397 forms small circles around the target analyte level. A user may then visually distinguish large excursions that occur because the line 397 falls outside of the smaller circles.

In one aspect, different color indicators or different grayscale levels may be used to indicate to a user how much time has elapsed since the received analyte levels were within a quadrant corresponding to a particular rate of change or analyte level. Further, the graphical display screen 395 may display an indicator corresponding to how long a user's analyte levels have been in a certain zone or quadrant or the time elapsed from a particular event such as a meal or an exercise period.

Referring back to FIG. 3A, in certain embodiments, either one of the first panel 303 or the second panel 320 of the information mode home screen 300 may not have data to display. In such cases, hash marks or other indicators may be output in one of the first panel 303 or the second panel 320 to indicate data is not available for that particular panel. Such cases may be present when a sensor is currently active but no data has been received, data was lost or is unavailable, or the data has been masked for a specified amount of time.

In certain embodiments, when the information mode home screen 300 is displayed and a user actuates the jog wheel 230 or an input button 220, at least one of panels 303 or 320 may be replaced with a sensor life indicator screen (not shown). The sensor life indicator screen may display the current sensor life, such as for example, the sensor life remaining for sensor 101 (FIG. 1) and provide information (e.g., a grace period) as to if/when the current sensor needs to be replaced. This data may be shown as text, an icon, a graphic, an animation, a video, or a combination thereof. It is also contemplated that auditory and/or vibratory or other tactile alarms may be output in conjunction with the sensor life indicator screen to notify a user that the sensor needs to be replaced or will need to be replaced within a given period of time. In certain embodiments, a graph showing the signal strength, the charge remaining in the battery of the analyte monitoring device 200 and/or the charge remaining on the battery of the transmitter may be output and displayed in one or more panels or on sensor life indicator screen.

In certain embodiments, information mode home screen 300 may also include system information icons on a portion or panel of the information mode home screen 300. In certain embodiments, the system information icons indicate the status of various system components. Such icons may include a wireless connection icon 330, an audio/vibratory settings icon 332, a calibration status icon 334, and battery icon 336. Although not shown, other icons may be displayed including a sensor life icon that shows the remaining life of a sensor, such as, for example, sensor 101 or an alarm notification icon indicating that an alarm or alert condition is detected. In certain embodiments, home screen 300 may also show the current date 338 and the current time 340. As with other information displayed on display 210, the date and time may be displayed as color coded numbers, text, an analog clock or a combination thereof.

The wireless connection icon 330 shows the status of the wireless connection between the transmitter, such as transmitter unit 102 (FIG. 1), and the analyte monitoring device 200. When a connection between the transmitter and the analyte monitoring device 200 is established, the wireless connection icon 330 is output on the display indicating the connection has been made. However, when a connection has not been established between the transmitter and the analyte monitoring device 200, a second form of the wireless connection icon 330 is output on the display to indicate a connection has not been established. For example, when the connection is established between the transmitter and the analyte monitoring device 200, the wireless connection icon 330 is output on the display 210 with connection strength indicators as shown in FIG. 3A. When a connection has not been established between the analyte monitoring device 200 and the transmitter, the wireless connection icon 330 is output showing a small "x" disposed by or on the wireless connection icon 330. In one aspect, the wireless connection icon 330 is output according to the signal strength of the connection between the analyte monitoring device 200 and the transmitter. For example, additional connection strength indicators may be displayed next to the wireless connection icon 330 or the wireless connection icon 330 may be displayed in a bright color to indicate a strong connection is established between the analyte monitoring device 200 and the transmitter. If a weak connection is established between the analyte monitoring device 200 and the transmitter, the wireless connection icon 330 is output in a different color or has fewer connection strength indicators. Although specific indicators are mentioned, it is contemplated that various other indicators may be used to show, for example, connection strength. Although a wireless connection is specifically mentioned, it is contemplated that various connection protocols may be used including, a Bluetooth® connection, a ZigBee® connection, a radio frequency (RF) connection, a radio frequency identification (RFID) connection, an infrared connection, and a wired connection.

In certain embodiments, audio/vibratory settings icon 332 shows the audio and/or vibratory settings for the analyte monitoring device 200. In other embodiments, audio and vibratory settings may be displayed as separate icons or indicators. In certain embodiments, the audio/vibratory settings are applied to glucose readings, data loss, and various system alarms. Various icons may be used to represent the various settings available, such as, for example, an audio and vibrate setting in which the audio/vibratory setting icon 332 is output showing a note being surrounded by vibration signals, an audio only setting in which the audio/vibratory setting icon 332 is output showing only a note, a vibrate only setting in which the audio/vibratory setting icon 332 is output showing a plurality of vibration signals or a mute setting in which the audio/vibratory setting icon 332 is output showing a note having a line or an "x" therethrough. It is also contemplated that the overall volume of the analyte monitoring device 200 may be displayed by the audio/vibratory icon 332. For example, if the overall volume of the system is high, the audio/vibratory icon 332 may be output in a first color, while if the overall volume of the system is low, the audio/vibratory icon 332 may be output in a second color.

In certain embodiments, calibration status icon 334 is output on the display to notify a user that a sensor, such as, for example, sensor 101 (FIG. 1) should be calibrated. In certain embodiments, a control unit or processor of the analyte monitoring device 200 outputs an alarm and/or alert screen to notify a user that the sensor should be calibrated. For example, when a predetermined time period has elapsed since the last calibration, an alarm is output a predetermined number of times and a blood drop icon is output on the display. In certain embodiments, different icons may be output on the display 210 based on various sensor calibration statuses. For example, output of a blood drop icon on the display 210 may indicate that it is time to calibrate the system, while an hourglass icon output on the display 210 may indicate that the sensor should be calibrated but the system is not ready for the calibration. In one aspect, output of an hourglass icon may indicate that glucose results are temporarily unavailable. In certain embodiments, a blood drop icon or hourglass icon may be output on the display 210 with a plurality of fill indicators to indicate a time period remaining until the sensor should be calibrated. For example, if the sensor should be calibrated in 10 hours, the two out of four fill indicators of the blood drop icon may be output on the display 210. If the sensor should be calibrated in 4 hours, one out of four fill indicators of the blood drop icon are output on the display 210. In another embodiment, the calibration status icon 334 may be output in various colors based on an expected calibration time. For example, if 10 hours remain until an expected sensor calibration time, the calibration status icon 334 is output in a first color (e.g., green). When 4 hours remain until an expected sensor calibration time the calibration status icon 334 is output in a second color (e.g., red).

In certain embodiments, battery icon 336 represents the percentage of charge remaining in a battery of the analyte monitoring device 200. Although not shown, a similar battery icon may be output on the display to indicate the percentage of charge remaining in the battery of the transmitter, such as, for example, transmitter unit 102 (FIG. 1). In certain embodiments, the battery icon 336 is output having at least four indicators with each of the indicators representing 25% of the battery life. As battery life of the analyte monitoring device 200 drains, each of the indicators of the battery icon 336 is output in a different color. For example, as battery life is depleted from a 100% charge to a 75% charge, a processor or output unit of the analyte monitoring device 200 causes the first indicator of the battery icon 336 to change from green, to yellow to red to indicate that the user is reaching 75% charge while the remaining three indicators of the battery icon are output in green. As battery life of the analyte monitoring device 200 is continually depleted, the remaining three indicators are output in different colors to indicate the percentage of battery life left in the analyte monitoring device 200. In certain embodiments, the battery icon 336 may also indicate whether the analyte monitoring device 200 is currently being charged. When the analyte monitoring device 200 is being charged, each of the four indicators of the battery icon 336 may be output in different colors in a similar manner as discussed above although in the opposite color order. For example, when the battery of the analyte monitoring device 200 is being charged from 75% to 100% the color of the first indicator of the battery icon 336 is output from red to yellow to green to indicate the status of the charge. In another embodiment, the battery icon 336 may be output in various colors depending on the amount of charge remaining in the battery of the analyte monitoring device 200. In certain embodiments, flashing and/or fading of the battery icon may be used in lieu of or in conjunction with the colors to indicate battery status. In certain embodiments, more or less than four indicators may be used to indicate battery status or a single dynamic indicator may be utilized.

Although specific icons have been discussed with respect to each of the wireless connection icon 330, the audio/vibratory settings icon 332, the calibration status icon 334, and the battery icon 336, it is contemplated that various icons, text, graphics, animations, and/or video in varying colors, shades and levels of brightness may be output to indicate a status of the various components of the analyte monitoring device 200 or the analyte monitoring system 100 (FIG. 1).

In certain embodiments, information mode home screen 300 also includes softkey labels 342 and 344. In certain embodiments, each softkey label 342 and 344 is outlined to help distinguish the label from the other icons and text on the information mode home screen 300. Further, each softkey label 342 and 344 specifies actions that occur when a corresponding input button 220 (FIG. 2A) is actuated or when a touch sensitive area of the display 210 corresponding to the softkey labels 342 and 344 are touched. For example, if the input button 220 corresponding to softkey label 342 is actuated, a full screen graph, such as, for example, timeline graph 400 (FIG. 4a) will be output on the display 210 of the analyte monitoring device 200. If however, the input button 220 corresponding to softkey label 344 is actuated, a menu, such as, for example, menu screen 600 (FIG. 6) will be output on the display 210 of the analyte monitoring device 200. Although specific softkey labels have been discussed, it is contemplated that various other softkey labels may be used. It is also contemplated that the softkey labels may be user selectable to enable a user to customize which features and data may be accessed directly from the information mode home screen 300. In certain embodiments, the analyte monitoring device 200 may "learn" which functions and display screens are used by the user most frequently and automatically update the softkey labels accordingly. For example, if a processor or control unit of the analyte monitoring device 200 detects that a user is consistently accessing a particular menu screen, a softkey label corresponding to that particular menu screen will be output on the information mode home screen 300. Although two softkey labels are shown in FIG. 3A, it is contemplated that any number of softkey labels may be output on the display 210.

FIG. 3B illustrates an activity mode home screen 350. According to certain embodiments, the activity mode home screen 350 includes a plurality of panels or screens that may be used to display information to a user. As with the information mode home screen 300 (FIG. 3A) some of the panels of the activity mode home screen 350 may display user state information while other panels of the activity mode home screen 350 show system state information. For example, panel 360 may be configured to display glucose information 322 and trend information icon 324 as described above with reference to FIG. 3A. Additionally, panel 370 may be configured to display system information icons such as a wireless connection icon 330, an audio/vibratory settings icon 332, a calibration status icon 334, and battery icon 336 as previously described. Activity mode home screen 350 may also include a time indicator 340, a date indicator (not shown) and a plurality of softkey labels 342 and 344 as were described above with reference to FIG. 3A.

In certain embodiments, activity mode home screen 350 includes a third panel 380 that includes a menu 385 with user selectable menu items. As shown in FIG. 3B, the menu items may include an alarms menu item, a status menu item, a reports menu item, an add event menu item, and a settings menu item. Each menu item has specific functionality, display screens or submenus associated therewith, each of which will be described in greater detail below. In certain embodiments, each menu item may be selected by a user actuating a jog wheel, such as, for example, jog wheel 230 (FIG. 2C). When a particular menu item is highlighted, such as, for example, the alarms menu item as shown in FIG. 3B, a user may select the highlighted item by either pressing an input button 220 or by pressing the jog wheel 230 inwardly to select the highlighted item. In certain embodiments, when the display 210 is a touch sensitive display, the user may simply touch the menu item output on the display to make a selection.

FIG. 3C illustrates an alternative arrangement of an information mode home screen 390 according to embodiments of the present disclosure. As with information mode home screen 300, information mode home screen 390 includes a first panel 302 that displays a user's historical analyte data represented as a graph 305. The graph 305 includes a graph line 310 that represents continuous glucose readings taken over a time t, lower glucose target indicator 312 and an upper glucose target indicator 314. In certain embodiments, the graph 305 may also include event data icons 318 that represent various events of the user during the time period the graph represents. Examples of such events include, but are not limited to, discrete blood glucose measurements, insulin dosing, meal times, and exercise periods.

Information mode home screen 390 may also be configured to display glucose information 322 and trend information icon 324 as described above with reference to FIG. 3A. Additionally, information mode home screen 390 may include a third panel 370 configured to display system information icons such as a wireless connection icon 330, an audio/vibratory settings icon 332, a calibration status icon 334, and battery icon 336 as well as a time indicator 340, a date indicator (not shown) and a plurality of softkey labels 342 and 344 as were described above with reference to FIG. 3A.

Figure 4A:
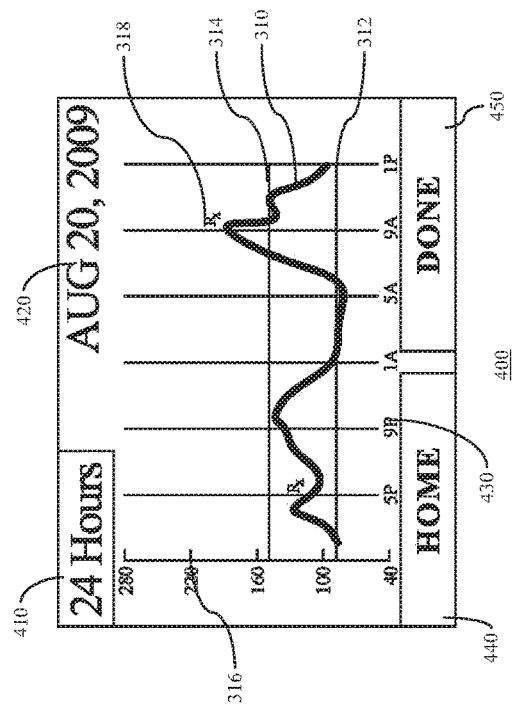

FIG. 4A illustrates a display screen showing a timeline graph 400 according to embodiments of the present disclosure. The display screen showing the timeline graph 400 may be output on the display when an input button 220 (FIG. 2A) is actuated that corresponds to a "Graph" softkey label such as, for example, softkey label 342 (FIG. 3A).

In certain embodiments, the timeline graph 400 includes similar display features as those described above with reference to FIG. 3A. For example, timeline graph 400 includes a graph line 310 that represents continuous glucose readings. User-selectable lower glucose target indicator 312 and upper glucose target indicator 314 may also be displayed on the timeline graph 400. In certain embodiments, the timeline graph 400 is configured to display a range of numbers corresponding to glucose level, such as from 40 mg/dL to 280 mg/dL on the y-axis with tick marks 316 at various points within the range, such as at 40 mg/dL, 100 mg/dL, 160 mg/dL, 220 mg/dL, and 280 mg/dL. Although specific tick mark values are mentioned, it is contemplated additional tick mark values may be used. For example, if a user uses a zoom-in feature, the tick marks may have different values (e.g., 60 mg/dL, 70 mg/dL, 80 mg/dL, 90 mg/dL, and 100 mg/dL) corresponding to how close the user zoomed-in on the timeline graph 400. In certain embodiments, if glucose values fall below a lower threshold, such as 40 mg/dL or climb above an upper threshold, such as 280 mg/dL, the timeline graph 400 displays those values at 40 mg/dL or 280 mg/dL respectively. The timeline graph 400 may also be configured to display a range of numbers on the y-axis in various units of measure, such as a range from 2 mMol/L to 16 mMol/L with tick marks at 2 mMol/L, 6 mMol/L, 8 mMol/L, 12 mMol/L, and 16 mMol/L respectively.

As described above, in certain embodiments, graph line 310, lower glucose target indicator 312 and upper glucose target indicator 314 may be output in various colors so a user may more readily identify points of interest on the timeline graph 400. Additionally, values corresponding to each of the lower glucose target indicator 312 and the upper glucose target indicator 314 may be changed by a user or changed by a healthcare professional.

In certain embodiments, timeline graph 400 may also include event data icons 318. The event data icons 318 are placed at locations on the graph according to the time at which the event took place and/or in conjunction with the monitored glucose level depicted by the graph line 310. Such events may include alarms or alerts, discrete blood glucose measurements, insulin dosing, exercise periods, meal times, state of health, and the like. In certain embodiments, particular event data icons, such as blood glucose reading icons, and custom event icons, may be placed on the graph according to continuous glucose monitoring levels and/or times in which the events took place without simultaneously showing a graph line, such as shown in FIG. 4E. Still referring to FIG. 4E, a user may select an earlier date represented by the graph or later date represented by the graph by actuating input buttons 220 having corresponding softkey labels 440 and 450.

Referring back to FIG. 4A, as shown, each event may have a corresponding icon to enable a user to more readily identify what activities took place at certain times and which activities, if any, may have caused an increase or decrease in glucose levels. In certain embodiments, the user may select an event depicted by the event data icon 318 and view details on that particular event. The selection may be made by highlighting the particular event using a jog wheel 230 (FIG. 2C) or input button 220 (FIG. 2A) and then selecting the highlighted event icon. If a touch sensitive display is used, a user may touch the icon on the display to view the details of the selected event.

In certain embodiments, timeline graph 400 also displays a time period setting 410 and a date 420 that the timeline graph 400 represents. For example and as shown in FIG. 4A, the time period selected is 24 hours and the date is Aug. 20, 2009. Thus, the timeline graph 400 shows continuous glucose readings for a complete 24 hour period as indicated by the time periods 430. If the jog wheel 230 (FIG. 2C) is actuated, a user may chronologically view previous or subsequent 24 hour time periods of the timeline graph 400. In certain embodiments, the time period setting 410 may be adjusted by a user and may include various time periods, such as, for example, 2 hour time periods, 4 hour time periods, 6 hour time periods, 12 hour time periods or 24 hour time periods, or others. In certain embodiments, regardless of which time period setting is used, the timeline graph 400 is output showing only the selected time period (e.g. 2 hours).

In certain embodiments, softkey button labels 440 and 450 are also included on the timeline graph 400 display screen. In certain embodiments, when a corresponding input button 220 is actuated, the user is returned to a home screen, such as, for example, information mode home screen 300 (FIG. 3A). In another embodiment, the user may be returned to a menu or submenu that enabled the user to navigate to the timeline graph 400 screen. In certain embodiments, if the user navigates away from the timeline graph 400 screen and later wants to return to the timeline graph 400 screen, a remember function may be utilized which returns the user to the specific time period represented by the timeline graph 400 that the user was viewing before exiting the timeline graph 400 display screen. In certain embodiments, the remember function may be used for each display screen of the user interface of the analyte monitoring device 200.

Figure 4B:
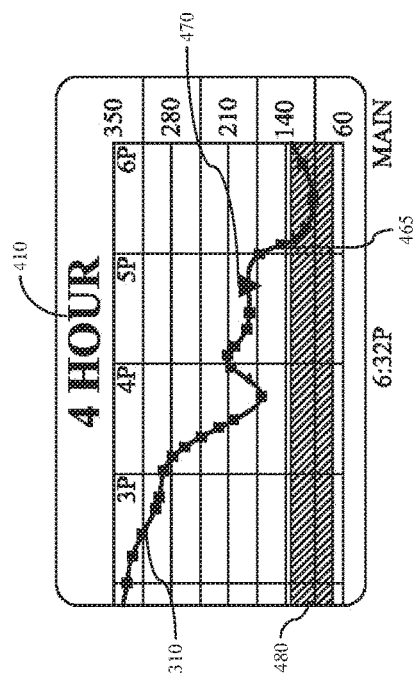

FIG. 4B illustrates a display screen showing a timeline graph 460 according to certain embodiments of the present disclosure. As with timeline graph 400, timeline graph 460 includes a graph line 310 that represents continuous glucose readings received over a user selectable period of time 410. The graph line 310 may also include a plurality of analyte data icons 465 to indicate the actual analyte level data values measured by sensor 101 and transmitted to analyte monitoring device 200 (FIG. 2A) over the displayed period of time. In addition to analyte data icons 465, one or more alarm notification icons 470 and/or event notification icons 318 (FIG. 4A) may also be displayed on or near the graph line 310 to indicate that an alarm notification was issued over the measured period of time or that the user participated in a particular event. In certain embodiments, the user may acquire additional information regarding the alarm or event such as analyte levels, insulin bolus administered, meal intake details and activities and the like by selecting one of the notification icons 470. In this manner, a user can obtain current, retrospective, and/or historic statistical information surrounding each notification icon 470 displayed on the timeline graph 460.

In certain embodiments, a softkey button or touch enabled area on the display enables the user to access the additional information by highlighting or otherwise actuating the notification icon 470. When actuated, the user is able to access detailed information about the particular notification, such as measured glucose level, rate of change, historic data, trend information or activity information. The informational screen may also include summary information for a number of similar types of events such as hyperglycemic events, hypoglycemic events, rapidly rising glucose events or rapidly falling glucose events. This information may also include frequency of occurrence relative to specific periods of time or relative to other behavior or treatments.

In certain embodiments, timeline graph 460 may also include one or more shaded portions 480 to indicate low and/or high glucose threshold levels. The shaded portions 480 may be color coded as selected by a user to give the user clear indication of when the monitored glucose levels of the user were above or below predetermined threshold levels.

FIGS. 4C-4D illustrate exemplary graphs 490 and 495 that show blood glucose levels versus time for two simulated sets of data. Simulated data such as shown in FIGS. 4C-4D may be used in a training mode such as will be described in more detail below. Referring to FIG. 4C, a first set of data points 492 output on the graph 490 show simulated data for a user that applied a late meal bolus (e.g., the user did not apply the bolus until after the meal had started). As indicated on the graph 490, the late meal bolus caused the user's blood glucose value to rapidly rise and then level off at a high amount after the late meal bolus had been applied.

The second set of data points 494 shows simulated data for a user that applied an on-time bolus that was under-dosed (e.g., the user applied the bolus before the meal began but did not apply the right amount). As a result of the on-time bolus, the user's blood glucose value did not spike when the user applied the late meal bolus as shown by the data points 492. However, as shown by the data points 494, the user's blood glucose value continued to rise consistently because the bolus was under-dosed or the timing was mismatched with the meal absorption.

FIG. 4D illustrates the same data from FIG. 4C, however, FIG. 4D illustrates blood glucose values in the y-axis versus the current trend or rate of change of the blood glucose values in the x-axis. As shown by the data points 497 (corresponding to data points 492), when a late meal bolus is applied, both the blood glucose value and the rate of change rapidly escalated. Similarly, as shown by data points 499 (corresponding to data points 494) the user's blood glucose value did not ascend as high when an under-dosed bolus was applied on time. However, because the bolus was under-dosed or otherwise mismatched to the meal, the rate of change of the blood glucose was positive and the user's blood glucose level continued to rise.

Figure 4F:
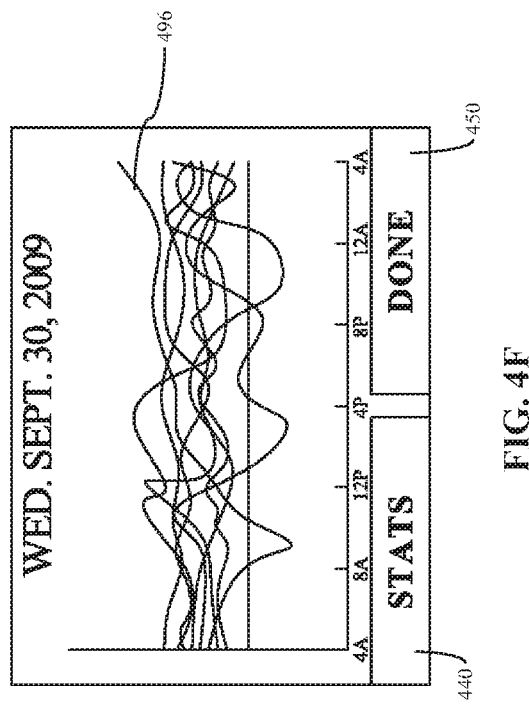
Figure 4E:
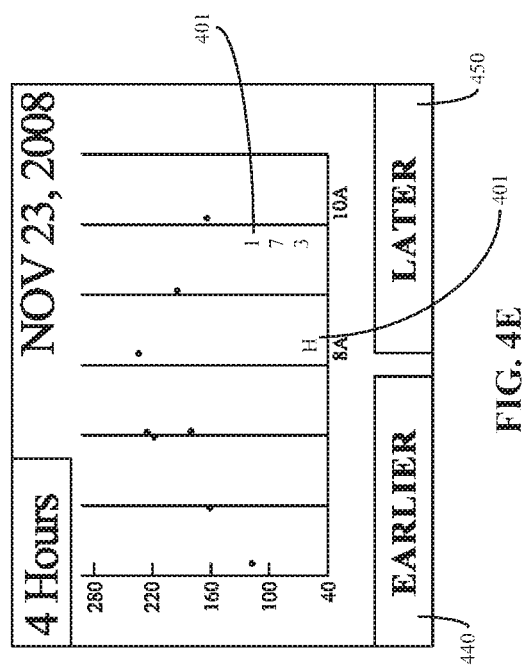

FIG. 4F illustrates another exemplary timeline graph according to embodiments of the present disclosure. As shown, the graph depicted in FIG. 4F includes multiple graph lines 496 with each graph line 496 representing analyte levels for a respective day of the week. In certain embodiments, each graph line 496 may be color coded based on a day of the week. In another embodiment, each graph line 496 may be color coded based on a severity of glucose level fluctuations. In certain embodiments, a user may highlight each of the graph lines 496 using a jog wheel, touching a portion of the touch sensitive display of actuating a softkey button having a corresponding softkey label 440 or 450. When the graph line is highlighted, statistics about the selected graph line 496 or event data, such as blood glucose tests, may be displayed on the highlighted graph line. If a user does not want to view each graph line for each day of the week, the user may select to view particular days, such as weekend or weekdays. The user may then scroll between a graph having five graph lines 496 representing the weekdays and a second graph having two graph lines 496 representing weekend days. Referring still to FIG. 4A-4F, in certain embodiments, alarm or alert notifications may be triggered by more situations where sensor data exceed thresholds 312 and 314.

Figure 5A:
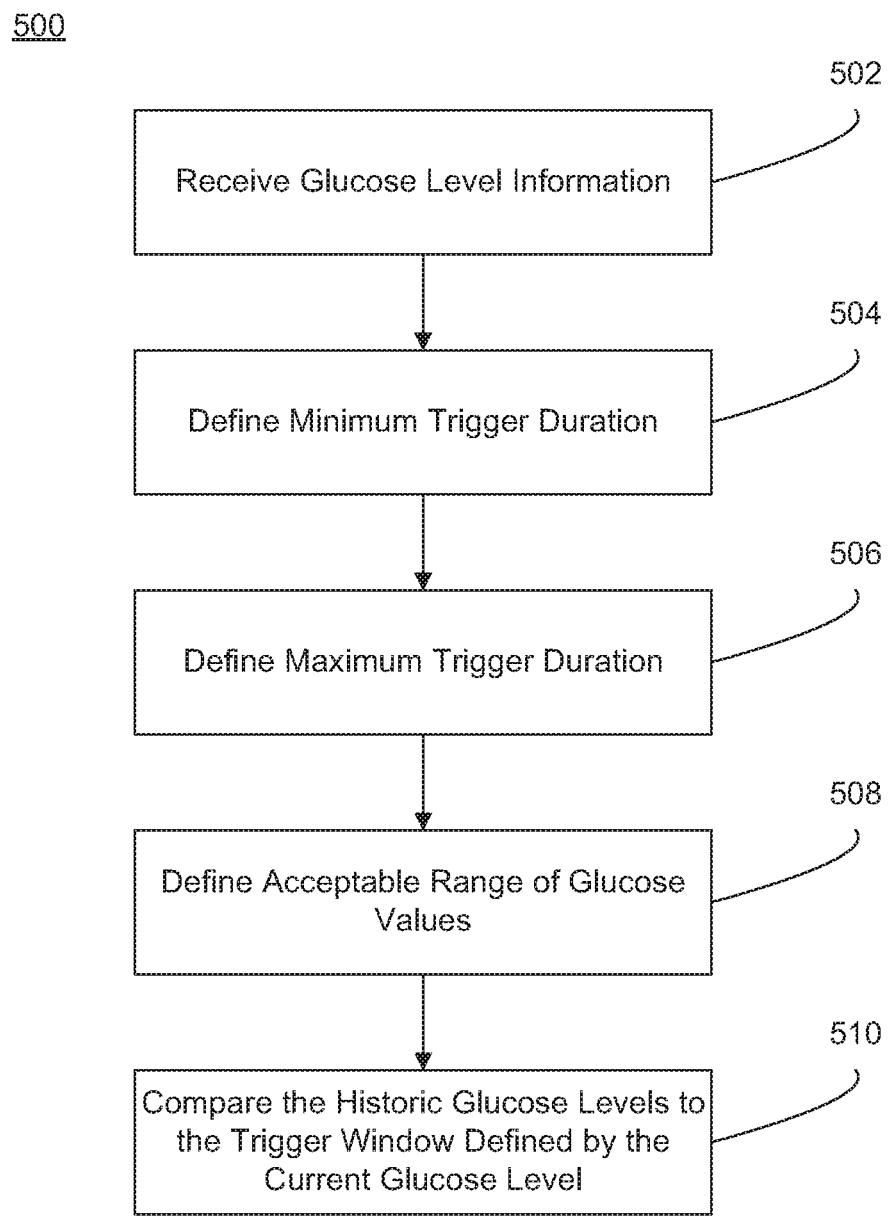
FIG. 5A illustrates a method for retrospectively evaluating a series of received glucose values to detect an alert condition by comparing the received glucose values to a trigger window according to embodiments of the present disclosure.

FIG. 5A illustrates a method 500 for retrospectively evaluating a series of received glucose data values to detect an alert condition by comparing the received glucose data values to a trigger window in embodiments of the present disclosure. In certain embodiments, when a received analyte level exceeds a threshold level set by the user or healthcare professional, an alarm may be output indicating that the user's analyte level has exceeded the threshold level. However, because only the most recently received glucose level is compared against the threshold value, the user may experience undesirable glucose fluctuations without being notified of the fluctuations. For example, a user's glucose level may be increasing or decreasing rapidly but still be within a predetermined threshold range. Because the glucose level is still within the predetermined threshold range, an alert condition may not be triggered and the user is not notified of the situation. Additionally, a user may not be notified of undesirable glucose fluctuations because an analyte monitoring device was not activated to receive (e.g. on-demand) analyte levels during the fluctuations or episodes of interest. As a result of not being notified, the user may have lost the opportunity to attempt to correct or stabilize glucose levels, such as, for example, by administering a bolus amount of insulin. Further, the user may have lost the opportunity to make a note of various conditions or events (e.g. diet, exercise, state of health, medications) that may have contributed to the rapid increase or decrease in glucose levels.

Referring to FIG. 5A, the routine for retrospectively evaluating a series of received glucose data values begins when glucose level information is received by a receiver unit (502) such as, for example, receiver unit 104 (FIG. 1). In certain embodiments, the glucose level information is a blood glucose value that is received from a user initiating a blood glucose test. In another embodiment, the glucose level information includes a current glucose data value that was received by the receiver unit 104 from a sensor 101 (FIG. 1) via a transmitter unit 102 (FIG. 1) at predetermined time periods. In yet another embodiment, the glucose level information may be received by the receiver unit 104 on-demand and a series of glucose data level readings are received simultaneously.

When the glucose level information has been received, a trigger window having a minimum trigger duration (504) and a maximum trigger duration (506) is defined. In certain embodiments, a trigger window is a window of time in which available historical glucose data values received during the window of time are retrospectively evaluated to determine which, if any, of the historical glucose data values fall outside an acceptable range defined by the trigger window with respect to a current glucose data value (e.g. which historical glucose data values have a rate of change that when compared with the current glucose data value cause the historical glucose data value to fall outside an acceptable rate of change). If the historical glucose data values fall outside the acceptable range defined by the trigger window, an alert notification is output, such as an alert screen or audible alarm, to alert the user of a possible ongoing rapid increase or decrease in glucose levels.

In certain embodiments, the minimum trigger duration defines a most recent point in time in the past (e.g. 15 minutes before the current glucose data value is received) in which available historical glucose data values will be compared to the threshold values of the trigger window. The maximum trigger duration defines a most distant point in time in the past (e.g. two hours before the current glucose level is received) that historical glucose data levels will be compared to the threshold values of the trigger window. In certain embodiments, the minimum trigger duration and the maximum trigger duration are set by a user or a healthcare provider using, for example, a display screen and timeframe selection items such as described herein. For example, a user or healthcare provider may navigate to a minimum trigger duration and maximum trigger duration display screen and have the option to select a time period (e.g. 15 minutes, 2 hours etc.) of the minimum trigger duration and the maximum trigger duration.

When the minimum trigger duration and the maximum trigger duration have been defined, an acceptable range of glucose values is defined (508) by the user or healthcare provider. In certain embodiments, the acceptable range of glucose values between the minimum trigger duration and the maximum trigger duration are scaled such that all acceptable glucose data values in the trigger window fall within a particular mg/dL per unit of time when compared to the current glucose data value level. For example, once the user has set the minimum trigger duration and the maximum trigger duration, the user may also select an acceptable range of the trigger window represented as mg/dL per unit of time, such as, for example, 100 mg/dL per hour. In certain embodiments, both the numerical value of the mg/dL (e.g. 100) as well as the unit of time (e.g. one hour) may be selected by the user or healthcare provider.

Once the trigger window and the acceptable range have been established, available historical glucose data values are compared to the threshold values shown by the trigger window to determine which, if any, of the historical glucose data values fall outside the established acceptable range (510). As will be explained in greater detail below, the trigger window is created with respect to the most current glucose data value. Thus, as retrospective comparisons are made between the current glucose data value and the available historical glucose data values and the trigger window, current rapid rises or decreases in glucose levels may be more readily detected.

Figure 5B:
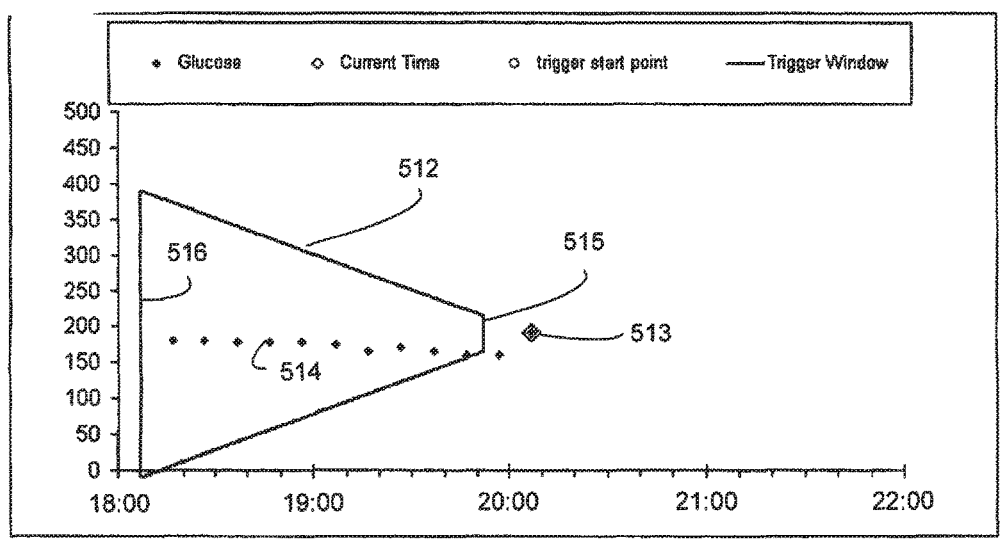
FIG. 5B illustrates a graph in which a trigger window is defined with respect to a current glucose data value according to embodiments of the present disclosure.

FIG. 5B illustrates a graph 511 in which a trigger window 512 is defined with respect to a current glucose data value 513 in embodiments of the present disclosure. As discussed above, the bounds of the trigger window 512 are defined by the minimum trigger duration 515 and the maximum trigger duration 516. As shown in FIG. 5B, the minimum trigger duration 515 is set approximately fifteen minutes prior to when the most current glucose data value 513 is received. The maximum trigger duration 516 is set approximately two hours prior to when the most current glucose data value 513 is received. Thus, when determining which of the historical glucose levels 514 fall outside of the threshold values established by the trigger window 512, comparisons will not be made for historical glucose data values that are received after the maximum trigger duration 516 and before the minimum trigger duration 515. For example, if a historical glucose data value was received two hours and five minutes prior to the current glucose data value 513, that particular historical glucose data value will not be compared against the threshold values established by the trigger window 512 because that particular historical data value does not fall within the defined trigger window 512 timeframe.

The trigger window 512 also shows an acceptable range or rate of change of glucose values as the trigger window progresses from the minimum trigger duration 515 to the maximum trigger duration 516. The acceptable range of glucose values between the minimum trigger duration 515 and the maximum trigger duration 516 is scaled such that all acceptable glucose values in the trigger window fall within a particular mg/dL per unit of time when compared to the current glucose level 513.

For example, and as shown in FIG. 5B, the acceptable rate of change defined by the threshold values of the trigger window 512 is a rate of change that is within 100 mg/dL per hour from the current glucose value 513. Thus, for a historical glucose data value to fall within the acceptable range defined by the trigger window 512, the rate of change from the historical glucose data value to the current glucose value must be less than 100 mg/dL per hour. Continuing with the example, as shown in the graph 511, the current glucose data value that was received at 8:10 PM is approximately 200 mg/dL. Thus, a historical glucose data value that was received at 7:10 PM and compared against the trigger window must be no lower than 100 mg/dL and no higher than 300 mg/dL. Because the historical glucose data value received at 7:10 PM falls within the range defined by the trigger window, a processor of the analyte monitoring device 200 determines that no significant rate of change has occurred between that particular historical glucose data value and the current glucose data value 513. As shown in the graph 511, none of the historical glucose data values fall outside the trigger window 512. Thus, it can be determined by the processor that the user is not experiencing or has not experienced an episode of rapidly increasing or decreasing glucose levels. Although a rate of change of 100 mg/dL per hour was specifically mentioned, it is contemplated that various rates of change per unit of time may be used, such as, for example, 5 mg/dL per 15 minutes, 10 mg/dL per 20 minutes etc.

Figure 5C:
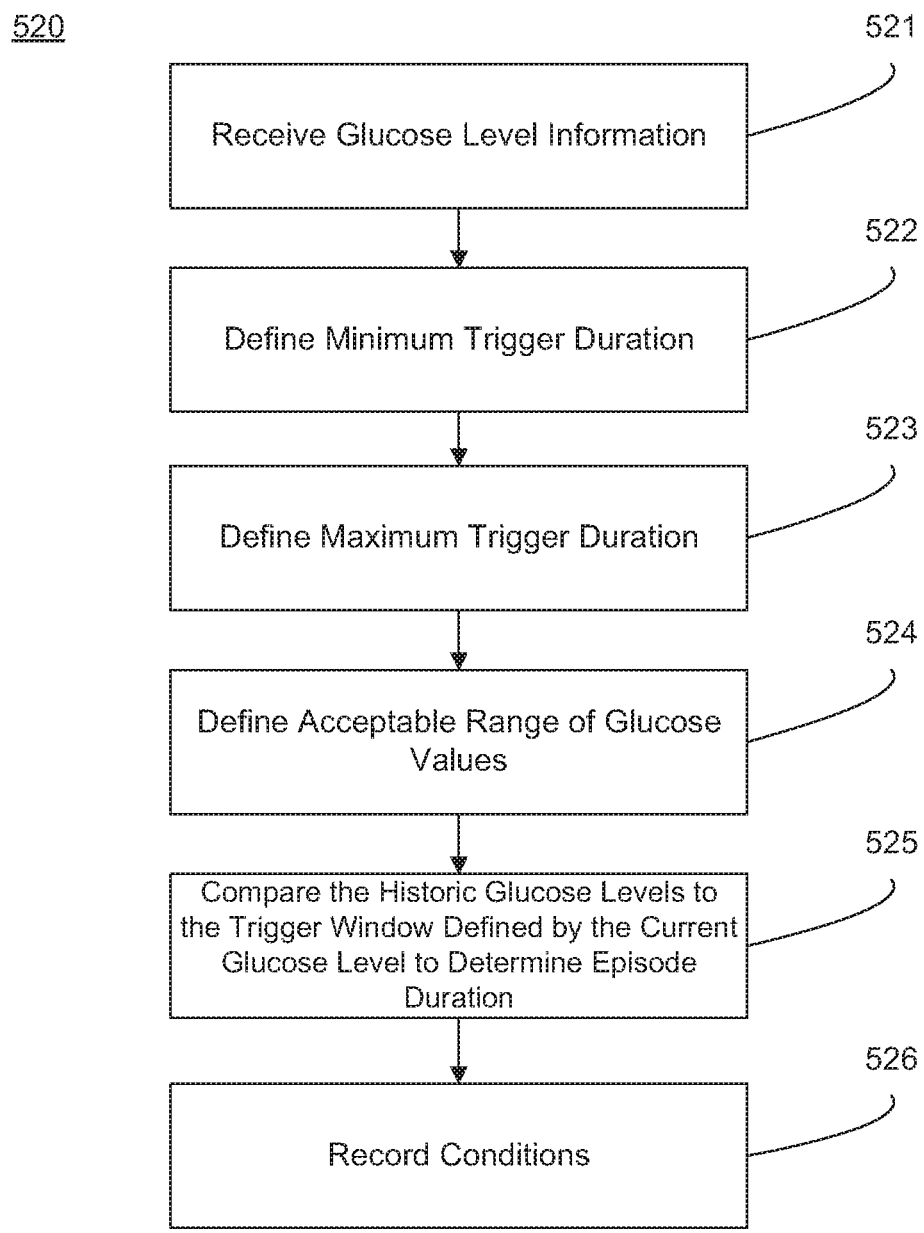
FIG. 5C illustrates a method for retrospectively evaluating a series of received glucose data values to detect an alert condition by comparing the received glucose data values to a trigger window according to embodiments of the present disclosure.

FIG. 5C illustrates a method 520 for retrospectively evaluating a series of received glucose data values to detect an alert condition by comparing the received glucose data values to a trigger window according to embodiments of the present disclosure. The routine for retrospectively evaluating a series of received glucose data values to detect an alert condition begins when glucose level information is received by a receiver (521) such as, for example, receiver unit 104 (FIG. 1). In certain embodiments, the glucose level information may be obtained by a sensor such as sensor 101 (FIG. 1) and stored in the transmitter unit 102 (FIG. 1) until the transmitter unit 102 receives a request from the receiver unit 104 to transmit the glucose level information to the receiver unit 104. In such embodiments, the glucose level information may contain at least a current glucose data value and at least one historical glucose data value. In another embodiment, the transmitter unit 102 may be configured to transmit the glucose level information to the receiver 104 at predetermined time intervals. In such embodiments, the most recently received glucose data value is designated as the current glucose data value.

When the glucose level information has been received, a trigger window is defined having a minimum trigger duration (522) and a maximum trigger duration (523). Once the minimum trigger duration and the maximum trigger duration have been defined, an acceptable range of glucose values is defined (524) with respect to the most recent or current glucose data value. As discussed above, each of the minimum trigger duration, the maximum trigger duration and the acceptable range may be defined or selected by a user or healthcare provider. The historic glucose data values are then compared by a processor to the threshold values established by the trigger window to determine which, if any, of the historic glucose data values fall outside the established acceptable range (525). If it is determined that one or more historical glucose data values fall outside the established range defined by the trigger window, this could indicate that an unacceptable glucose fluctuation is in progress.

If it is determined by the processor that one or more historic glucose data values fall outside the established acceptable range, the processor of the receiver unit 104 records the occurrence of the condition (526). In certain embodiments, recording the occurrence of the condition includes placing an icon on a graph, such as a timeline graph 400 (FIG. 4A). In other embodiments, the receiver unit 104 may be configured to generate a graph similar to the graph 531 of FIG. 5D and the graph is output on a display screen of the receiver unit 104. In certain embodiments, when a condition is detected, an alarm and/or an alert screen is output on the receiver unit 104 to notify the user of the detected condition. Additionally, when the user is notified of the condition, the user may be prompted by the alert screen to record details of events (e.g., diet, activity, medication etc.) that may have caused the fluctuation to occur.

In certain embodiments, a processor the receiver unit 104 is configured to automatically associate event information entered by a user (e.g. exercise periods, meals etc.) or other automatically detected events (e.g., hypoglycemia, hyperglycemia, rapid glucose increases, rapid glucose decreases, glucose threshold alarms, impending glucose threshold alarms) to the detected episode if the event falls within a matching window relative to the episode. For example, if it is determined, based on a historical glucose data value falling outside the acceptable range, that an episode of increased blood glucose levels is occurring, an event history log created by the user may be evaluated to determine if a particular event occurred within a predetermined time range prior to the start of the episode that may have caused the current increase in glucose values. In certain embodiments, the matching window may be any timeframe selected by a user or healthcare provider.

Figure 5D:
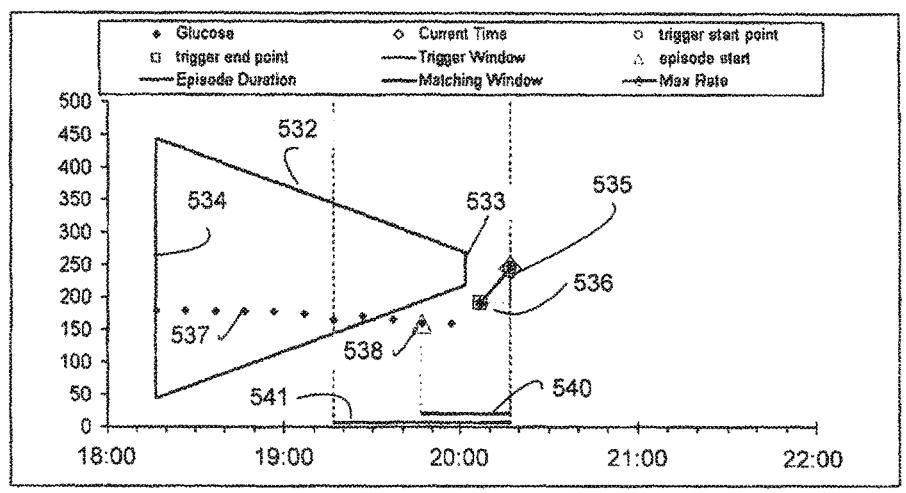
FIG. 5D is a graph illustrating a detected rise in glucose levels that is currently occurring according to embodiments of the present disclosure.

FIG. 5D is a graph 531 illustrating a detected rise in glucose levels that is currently occurring according to embodiments of the present disclosure. The graph 531 includes a trigger window 532 defined by a minimum trigger duration 533 and a maximum trigger duration 534. As discussed above, the trigger window 532 shows the acceptable range of glucose values between the minimum trigger duration 533 and the maximum trigger duration 534. Graph 531 also shows a plurality of glucose data values including a current glucose data value 535, a second most recently received glucose data value 536, and a plurality of other historical glucose data values 537.

Unlike the graph 511 of FIG. 5B, some of the historical glucose data values 537 fall outside of the trigger window 532. When at least one of the historical glucose data values fall outside the threshold set by the trigger window 532, an episode of increased or decreased glucose levels is likely ongoing or has occurred in the past. If an ongoing episode is detected, a processor of the receiver unit 104 is configured to determine the start of the episode. To determine a start of an episode, the historical glucose data values 537 are evaluated retrospectively starting from the second most recently received glucose data value 536 and moving back in time. Each historical glucose data value 537 is evaluated in turn to determine which historical glucose data value 537 is closest to the threshold level defined by the trigger window 532 in terms of time but farthest away from the threshold level defined by the trigger window 532 in terms of a glucose level relative to historical glucose data values immediately before and/or after the historical glucose data value currently being evaluated.

For example, as shown on the graph 531, the historical glucose data value 538 is indicated as the start of the episode because the historical glucose data value 538 is closest to the threshold level defined by the trigger window 532 in terms of time but has a lower glucose value than the previously received historical glucose data value. Once the start of the episode is identified, it can be determined how long the current episode has been ongoing. In the graph 531, the episode was determined to start when the historical glucose data value 538 was received at 7:50 PM. Because the current glucose data value was received at approximately 8:20 PM, the episode duration, indicated by line 540, has been occurring for 30 minutes.

In certain embodiments, when the episode duration has been determined, a local minimum rate of change and a local maximum rate of change for the episode duration may be determined by comparing each of the historical data values with each of the other historical data values to determine the smallest rate of change between the two values. Such information may be useful to determine which events or activities by the user, if any, had the least amount of significance to the occurrence of the episode. For example, if the user ate a meal twenty minutes prior to the occurrence of the smallest rate of change between two of the values, it can be determined that the meal did not affect the user's glucose level in that particular episode.

The local maximum rate of change is the largest rate of change between any two values during the occurrence of the episode. As shown in the graph 531, the local maximum rate of change in the episode 540 occurred between the current glucose data value 535 and the second most recently received glucose data value 536. Because the local maximum rate of change is recorded, a user may use this information to determine which events, if any, may or may not have contributed to jump in glucose values between these two readings.

Also shown on graph 531 is a matching window line 541 that represents a matching window time period. In certain embodiments, the matching window time period is a time period that starts at a predetermined amount of time prior to the detected start of the episode and ends when the episode ends. For example, as depicted in FIG. 5D, the matching window time period starts approximately 30 minutes prior to the start of the detected episode and ends at the same time as the episode. Although a 30 minute time period is specifically shown, it is contemplated that various other time periods may be selected by a user or healthcare provider.

As discussed above, the matching window may be used to automatically associate events, that occurred during the matching window time period, to the episode to enable a user or healthcare provider to ascertain which events may have caused, or were at least related to, the rapid increase or decrease in glucose levels. Such examples include other significant increases or decreases in glucose, episodes of high or low glucose, glucose alarm events, meal times, exercise periods, and the like. For example, if a user recorded an event, such as, for example, a meal at approximately 7:30 PM and the episode started at 7:50 PM, it may be determined by the user or healthcare provider that the particular meal eaten by the user was at least a factor in the episode starting. Thus, the user may take steps to prevent future episodes from occurring by avoiding similar foods.

Figure 5E:
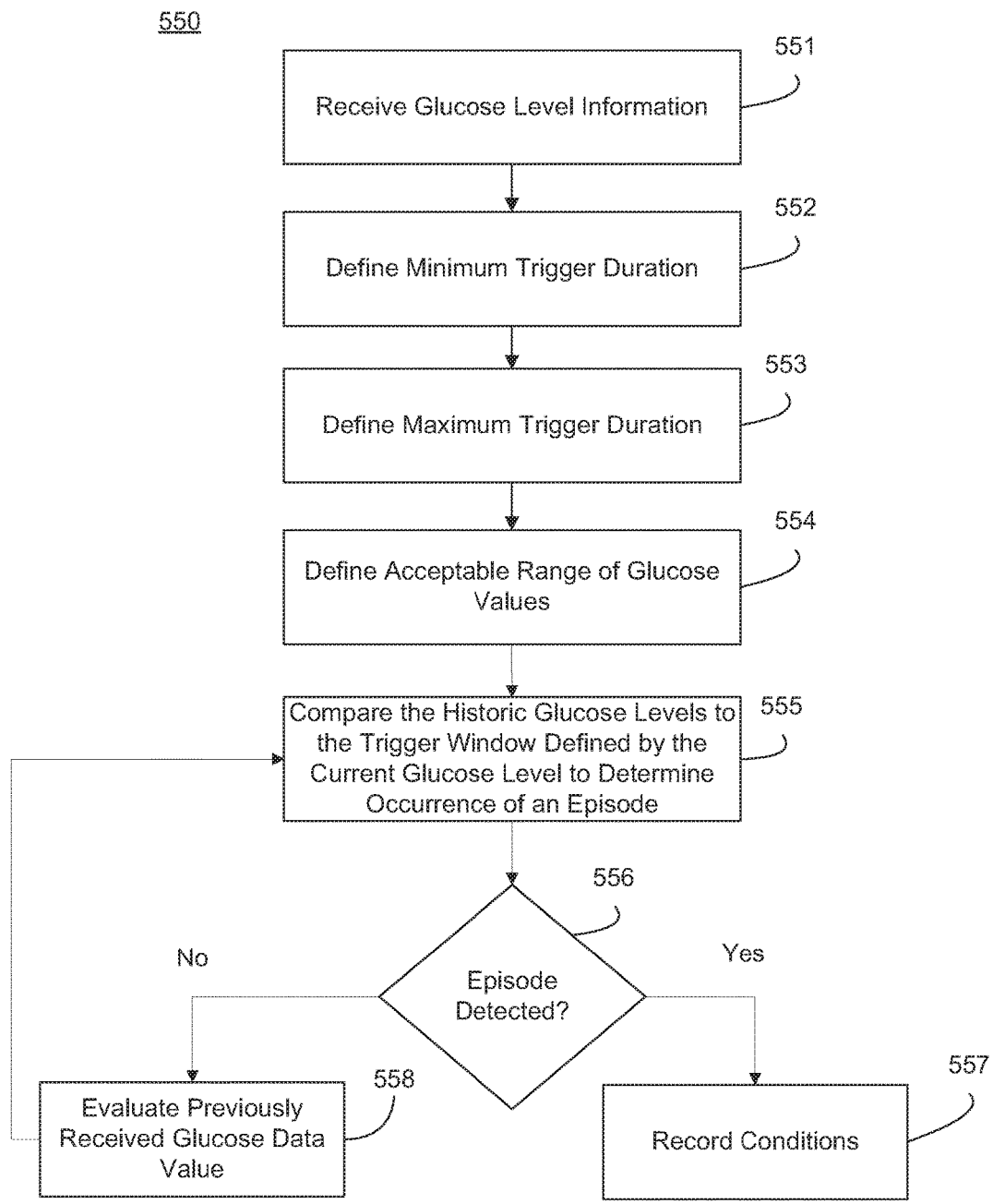
FIG. 5E illustrates a method for detecting an alert condition in a glucose monitoring system by retrospectively comparing historical glucose data values to each of the other historical data values with respect to a trigger window according to embodiments of the present disclosure.

FIG. 5E illustrates a method 550 for detecting an alert condition in a glucose monitoring system by retrospectively comparing historical glucose data values to each of the other historical data values with respect to a trigger window according to embodiments of the present disclosure. The routine for detecting an alert condition in a glucose monitoring system begins when glucose level information is received by a receiver (551) such as, for example, receiver unit 104 (FIG. 1). In certain embodiments, the glucose level information may be obtained by a sensor such as sensor 101 (FIG. 1) and stored in the transmitter unit 102 (FIG. 1) until the transmitter unit 102 receives a request from the receiver unit 104 to transmit the glucose level information to the receiver unit 104. When the glucose level information is transmitted in this manner, an entire series of glucose data values may be transmitted by the transmitter unit 102 and received by the receiver unit 104. The series of glucose data values includes at least a current or most recent glucose data value and at least one historical glucose data value. In another embodiment, the transmitter unit 102 is configured to transmit the glucose level information to the receiver 104 at predetermined time intervals and the most recently received glucose data value is set as the current glucose data value.

When the glucose level information has been received, a trigger window is defined having a minimum trigger duration (552) and a maximum trigger duration (553) such as described above. When the minimum trigger duration and the maximum trigger duration have been defined, an acceptable range of glucose values is also defined (554) with respect to the most recent or current glucose data value. As discussed above, each of the minimum trigger duration, the maximum trigger duration and the acceptable range may be defined or selected by a user or healthcare provider. A processor of the receiver unit 104 compares the historic glucose data values to the trigger window to determine which, if any, of the historic glucose data values fall outside the established acceptable range (555).

If it is determined that one or more historic glucose data values fall outside of the established acceptable range (556), the receiver unit 104 records the occurrence of the condition (557). In certain embodiments, recording the occurrence of the condition includes placing an icon on a graph, such as a timeline graph 400 (FIG. 4A). In other embodiments, the processor of the receiver unit 104 may be configured to generate a graph similar to the graph 531 of FIG. 5D and the graph is output on a display of the receiver unit 104. In certain embodiments, when a condition is detected, the receiver unit 104 may be configured to output an alarm or alert notification screen to notify the user of the detected condition. Additionally, when the user is notified of the condition, the user may be prompted to enter events (e.g., diet, activity, medication etc.) that may have caused the fluctuation to occur.

However, if it is determined that an episode is not currently ongoing (556), a second most recently received glucose data value is selected (558) and each of the historical data values are evaluated against the trigger window with respect to the second most recently received glucose data value (555). If it is determined that one or more historic glucose data values fall outside the established acceptable range (556) with respect to the second most recently received glucose data value, a processor of the receiver unit 104 records the occurrence of the condition (557) such as was described above. It should be noted, that if the second most recently received glucose data value is used to evaluate the rest of the historical glucose data values, the trigger window that was established based on the current glucose data value is used in the evaluation relative to the second most recently received glucose data value. Thus, the minimum trigger duration, the maximum trigger duration and the acceptable range of glucose values of the trigger window remain unchanged.

Figure 5F:
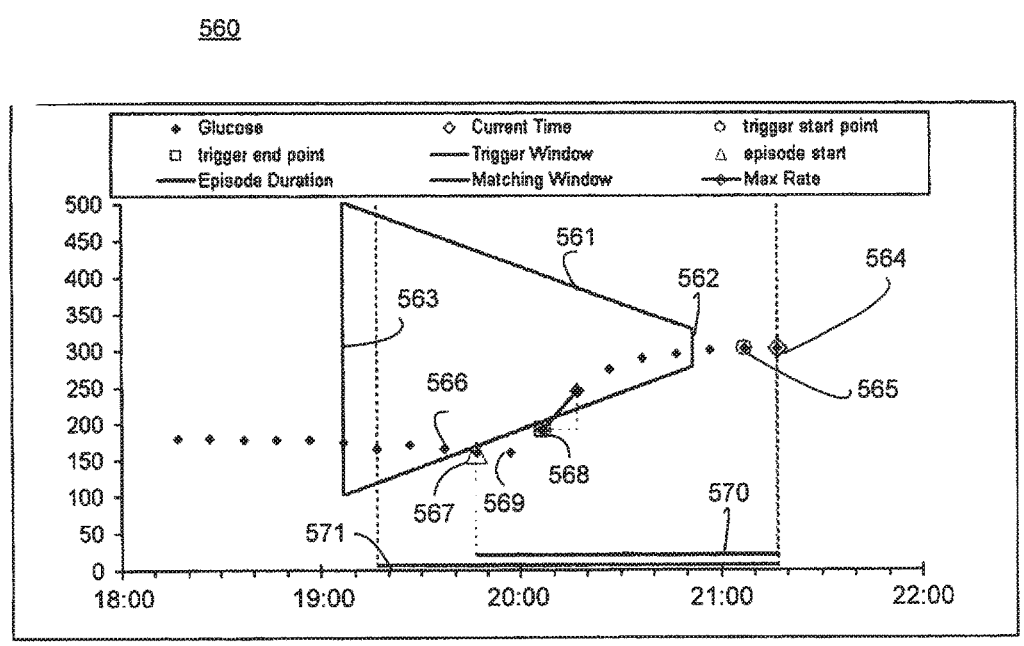
FIG. 5F illustrates a graph for retrospectively comparing a second most recently received glucose data value to historical glucose data values with respect to a trigger window according to embodiments of the present disclosure.

FIG. 5F illustrates a graph 560 for retrospectively comparing a second most recently received glucose data value to historical glucose data values with respect to a trigger window in embodiments of the present disclosure. As with the other graphs described above, graph 560 includes a trigger window 561 defined by a minimum trigger duration 562 and a maximum trigger duration 563. The trigger window 561 shows the acceptable range of glucose values between the minimum trigger duration 562 and the maximum trigger duration 563. Graph 560 also shows a plurality of glucose data values including a current glucose data value 564, a second most recently received glucose data value 565, and a plurality of other historical glucose data values 566. As discussed above, a processor of the receiver unit 104 compares the historical glucose data values 566 against threshold values defined by the trigger window 561 to determine if any of the historical glucose data values fall outside the threshold values defined by the trigger window 561 with respect to the second most recently received glucose data value 565.

Although not shown on the graph 560, when each of the historical glucose data values 566 were compared to the threshold values defined by the trigger window 561 with respect to the current glucose data value 564, none of the historical glucose data values fell outside the threshold. As a result, the second most recently received glucose data value 565 is selected as a new current glucose data value and the trigger window is effectively "moved back" to the location shown on the graph 560. Although the trigger window has been effectively "moved back", the parameters of the minimum trigger duration 562, the maximum trigger duration 563 and the acceptable range of glucose values remain constant. Thus the same parameters that were used to evaluate the historical glucose data values with respect to the current glucose data value 564 are used to evaluate the historical glucose data values with respect to the second most recently received glucose data value 565.

For example, if the minimum trigger duration 562 was set as 15 minutes prior to the current glucose data value 564 being received and the maximum trigger duration 563 was set as 2 hours prior to the current glucose data value being received, these same values are used when the second most recently received glucose data value 565 is analyzed in place of the current glucose data value 564. Thus, the minimum trigger duration 562 is set 15 minutes prior to when the second most recently received glucose data value 565 was received and the maximum trigger duration 563 is set as 2 hours prior to when the second most recently received glucose data value 565 was received.

As shown in the graph 560, once the trigger window 561 has been moved back, some of the historical glucose data values 566 now fall outside the threshold range defined by the trigger window 561. As a result, it may be determined that an episode, such as rapidly increasing glucose levels, occurred in the past and is either still occurring or is no longer occurring. Regardless of whether the episode is still occurring, a processor of the receiver unit 104 is configured to determine the start of the episode. When determining a start of an episode, the historical glucose data values 566 are evaluated retrospectively starting from the third most current glucose data value and moving back in time. Each historical glucose data value 566 is evaluated in turn to determine which historical glucose data value 566 is closest to the threshold defined by the trigger window 561 in terms of time but farthest away from the threshold defined by the trigger window 561 in terms of a glucose level relative to historical glucose data values immediately before and/or after the historical glucose data value currently being evaluated.

As shown in FIG. 5F, historical glucose data value 568 is the first historical glucose data value to fall outside of the threshold defined by the trigger window 561. However, before start of the episode is set at this particular point, the previously received historical glucose data value indicated by 569 is evaluated with respect to the historical glucose data value 568 to determine which historical glucose data value has a lower (or higher in cases of decreasing glucose levels) glucose level. If a previous historical glucose data value has a glucose level that is equal to or lower than the historical glucose data value that is currently being evaluated, additional subsequent historical glucose data values are evaluated. For example and as shown in the graph 560, because the historical glucose data value 569 has a lower glucose level than the historical glucose data value 568, additional previously received historical glucose data values will be evaluated to determine the start of the episode. However, if a previously received historical glucose data value has a glucose level that is higher than the historical glucose data value currently being evaluated, it is determined that the episode started with the historical glucose data value that is currently being evaluated.

As discussed above, because the historical glucose data value 569 has a lower glucose level than the historical glucose data value 568, additional previously received historical glucose data values will be evaluated to determine the start of the episode. As shown on the graph 560, as additional previously received glucose data values are evaluated, it is determined that the historical glucose data value 567 is where the episode began. In certain embodiments, this determination is made because the historical glucose data value 567 is closest to the trigger window 561 in terms of time and has an equal or substantially equal glucose value than the subsequent historical glucose data value 569. Further, the historical glucose data value that was received previous to the historical glucose data value 567 is within the trigger window 561 and therefore is not a part of the current episode.

Once the start of the episode is identified, it can be determined how long the current episode has been ongoing. In the example shown in FIG. 5F, the episode was determined to start when the historical glucose data value 567 was received at 7:50 PM. To determine the end of the episode, the second most recently received glucose data value 565 is compared against the current glucose data value 564 to determine if the current episode is ongoing. Because the subsequently received glucose data value (e.g., the current glucose data value 564) is equal to or greater than (or equal to or lower than in cases of decreasing blood glucose levels) the previously received glucose data value (e.g., the second most recently received glucose data value 565) it is determined that the episode is ongoing as shown by episode duration line 570. Thus the episode started at 7:50 PM and is ongoing through at least 9:20 PM. However, if the subsequently received glucose data value (e.g., the current glucose data value 564) is less than (or greater than in cases of decreasing blood glucose levels) the previously received glucose data value (e.g., the second most recently received glucose data value 565) the episode ended when the previously received glucose data value was received.

When the episode duration has been determined, a local minimum rate of change and a local maximum rate of change for the episode duration may be determined by comparing each of the historical data values with each of the other historical data values. As shown in the graph 560, the maximum rate of change in the episode occurred between the historic glucose data value 568 and the subsequently received historic glucose data value. Because the local maximum rate of change is recorded, a user may use this information to determine which events, if any, may or may not have contributed to jump in glucose values between these two readings as well as the severity of each rise.

Also shown on graph 560 is a matching window line 571 that represents a matching window time period. In certain embodiments, the matching window time period is a time period that starts at a predetermined amount of time prior to the start of the episode and ends when the episode ends. The matching window may be used to automatically associate events, that occurred during the matching window time period, to the episode to enable a user or healthcare provider to ascertain which events may have caused, or were at least related to, the rapid increase or decrease in glucose levels.

Figure 5G:
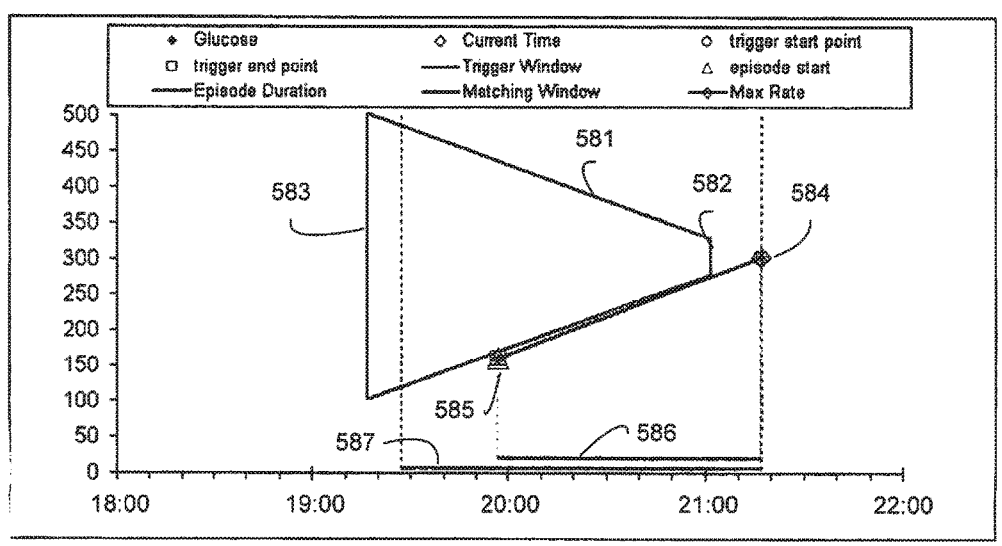
FIG. 5G illustrates a graph in which a trigger window is defined with respect to a current glucose data value and a previously received glucose data value according to embodiments of the present disclosure.

FIG. 5G illustrates a graph 580 in which a trigger window is defined with respect to a current blood glucose data value in embodiments of the present disclosure. In certain embodiments, graph 580 may be used in a test strip monitoring device to compare a newly acquired blood glucose reading to a previously received blood glucose reading. Although blood glucose readings are used instead of continuous glucose readings, the methodology is similar to the methodologies described above. As shown in FIG. 5G, graph 580 includes a trigger window 581 defined by a minimum trigger duration 582 and a maximum trigger duration 583. The trigger window 581 shows the acceptable range of glucose values between the minimum trigger duration 582 and the maximum trigger duration 583. Graph 580 also shows a plurality of blood glucose data values including a current blood glucose data value 584 and a previously received blood glucose data value 585. Although only two values are shown, it is contemplated that additional blood glucose values may be received and plotted on the graph. As with the historical glucose data values discussed above, the previously received blood glucose data value 585 is compared against threshold levels defined by the trigger window 581 to determine if the previously received blood glucose data value falls outside the threshold range defined by the trigger window 581 with respect to the current blood glucose data value 584.

In certain embodiments, a graph, such as for example graph 460 (FIG. 4B) may be output on the display 210 (FIG. 2A) of the analyte monitoring device 200 showing the detected rises and falls and highs and lows of received blood glucose data values based on a set of detection parameters. In certain embodiments, the set of detection parameters used for the graph may be similar to the parameters used to define a trigger window and/or an outer limit range associated with the trigger window. In certain embodiments an indicator, such as, for example, a triangle or rectangle, may be displayed on the graph that links or surrounds the blood glucose data values of a particular episode that was detected based on the detection parameters. In an embodiment, the indicators are color coded based on severity of the episode, duration of the episode, extreme high values of glucose data values in the episode, and/or extreme low values of glucose data values in the episode.

Referring back to FIG. 5G, because the previously received blood glucose data value 585 falls outside of the threshold level defined by the trigger window 581, a processor of the receiver unit 104 (FIG. 1) can determine that a rapid increase or decrease in blood glucose levels is ongoing. As a result, the processor of the receiver unit 104 may record the occurrence of the condition such as described above with respect to FIG. 5C.

In certain embodiments, if an ongoing episode is detected, the processor of the receiver unit 104 is configured to determine the start of the episode. Although there are only two blood glucose levels shown on the graph 580, the start of the episode is determined in the same manner as was described above with respect to FIG. 5D. As shown, the previously received blood glucose data value 585 is determined to be the blood glucose value at which the current episode started. Once the start of the episode is identified, it can be determined how long the current episode has been ongoing. As shown in FIG. 5G, the episode was determined to start when the first blood glucose data value 585 was received at approximately 8:00 PM and is continually ongoing up until at least approximately 9:20 PM when the current blood glucose value is received. Thus, the episode duration, indicated by line 586, has been occurring for 1 hour and 20 minutes.

In certain embodiments, when the episode duration has been determined, a local minimum rate of change and a local maximum rate of change for the episode duration may be determined such as was described above. Such information may be useful to determine which events or activities initiated by the user, if any, had the least amount of significance or greatest amount of significance to the occurrence of the episode.

Also shown on graph 580 is a matching window line 587 that represents a matching window time period. In certain embodiments, the matching window time period is a time period that starts at a predetermined amount of time prior to the episode starting and ends when the episode ends. For example, as depicted in FIG. 5G, the matching window time period starts approximately 30 minutes prior to the start of the detected episode and ends at the same time as the episode. Although a 30 minute time period is specifically shown, it is contemplated that various other time periods may be selected and used. As discussed above, the matching window may be used to automatically associate events, that occurred during the matching window time period, to the episode to enable a user or healthcare provider to ascertain which events may have caused, or were at least related to, the rapid increase or decrease in blood glucose levels.

Figure 5H:
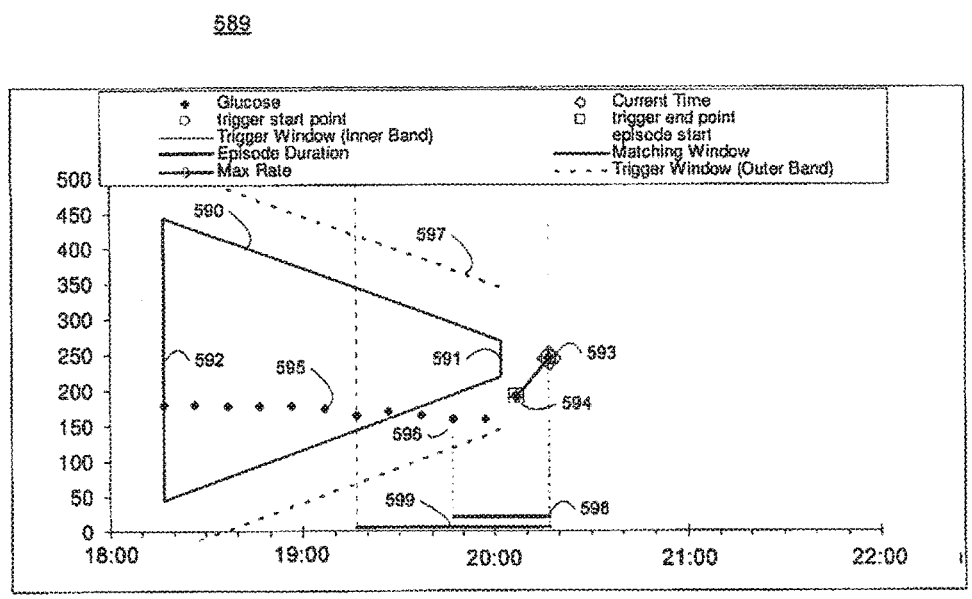
FIG. 5H is a graph illustrating episode detection in which all glucose data values associated with the episode fall within an outer limit range according to embodiments of the present disclosure.

FIG. 5H is a graph 589 illustrating episode detection in which all glucose data values associated with the episode fall within an outer limit range according to embodiments of the present disclosure. The graph 589 includes a trigger window 590 defined by a minimum trigger duration 591 and a maximum trigger duration 592. As discussed above, the trigger window 590 shows the acceptable range of glucose values between the minimum trigger duration 591 and the maximum trigger duration 592. Also shown on graph 589 is an outer limit 597 range. As will be described in greater detail below, when an outer limit range is used, only rise and fall episodes whose extreme glucose data values are contained entirely within the outer limit range 597 are detected. Any glucose data values of an episode that fall outside of the outer limit range 597 are ignored. In such instances, an episode associated with the extreme glucose data value is also ignored. Graph 589 also shows a plurality of glucose data values including a current glucose data value 593, a second most recently received glucose data value 594, and a plurality of additional historical glucose data values 595.

As shown in the graph 589, some of the historical glucose data values 595 fall outside of the trigger window 590 but within the outer limit range 597. As described above with respect to FIG. 5D, when at least one of the historical glucose data values fall outside the threshold set by the trigger window 590, an episode of increased or decreased glucose levels is likely ongoing or has occurred in the past. If an ongoing episode is detected, a processor of the receiver unit 104 is configured to determine the start of the episode. To determine a start of an episode, the historical glucose data values 595 are evaluated retrospectively starting from the second most recently received glucose data value 594 and moving back in time. Each historical glucose data value 595 is evaluated in turn to determine which historical glucose data value 595 is closest to the threshold level defined by the trigger window 590 in terms of time but farthest away from the threshold level defined by the trigger window 590 in terms of a glucose level relative to historical glucose data values 595 immediately before and/or after the historical glucose data value currently being evaluated.

For example, as shown on the graph 589, the historical glucose data value 596 is indicated as the start of the episode because the historical glucose data value 596 is closest to the threshold level defined by the trigger window 590 in terms of time but has a lower glucose value than the previously received historical glucose data value. However, should any historical glucose data values 595 fall outside of the outer limit range 597, the entire episode is ignored.

Although some historical glucose data values associated with an episode may fall outside of the outer limit range 597 and therefore the episode is not detected, in certain embodiments, a user or health care provider may adjust the trigger window parameters and/or the parameters associated with the outer limit range 597 so that in subsequent episode detections, the historical glucose data values that previously fell outside of the outer limit range 597, as well as the episode associated with historical glucose data value, is detected and may be evaluated and/or displayed. Such embodiments enable a user or health care provider to closely examine a number of episodes having varying degrees of severity.

In certain embodiments the parameters associated with the trigger window and the outer limit range 597 may be a set of predefined parameters and episode detection is applied for each predefined sets. For example, if ten sets of predefined parameters (e.g., minimum trigger duration, maximum trigger duration, acceptable glucose range etc.) are defined, episodes detection is performed on each set of parameters. In this way a spectrum of episodes are found and may be evaluated by a user or health care provider. Using sets of parameters such as described above enable identification of episodes having varying intensities and times. For example, long, slow episodes could be found with one set of parameters, while another set of parameters would detect short, fast episodes. As described above, the acceptable glucose range might be a band of values that fall within the outer limit range (e.g., the glucose data values that increased between 100 and 120 mg/dL per hour). Additionally, a single set of parameters may be further analyzed to determine the frequency at which episodes corresponding to the selected parameters occur. For example, short, fast episodes may be found to be occurring every day at a given time. Once the frequency of the episode is identified, a user or health care provider may take steps to identify what activities may be contributing to the frequency of the episode.

Once the episode has been detected and the start of the episode is identified (e.g., all of the historical glucose data values associated with the episode fall within the outer limit range 597), a time period of the episode can be determined. In the graph 589, the episode is determined to have started when the historical glucose data value 596 was received at 7:50 PM. Because the current glucose data value was received at approximately 8:20 PM, the episode duration, indicated by line 598, has been occurring for 30 minutes.

In certain embodiments, when an episode duration has been determined, a local minimum rate of change and a local maximum rate of change for the episode duration may be determined by comparing each of the historical data values with each of the other historical data values to determine the smallest rate of change between the two values. Such information may be useful to determine which events or activities by the user, if any, had the least amount of significance to the occurrence of the episode. For example, if the user ate a meal twenty minutes prior to the occurrence of the smallest rate of change between two of the values, it can be determined that the meal did not affect the user's glucose level in that particular episode.

The local maximum rate of change is the largest rate of change between any two values that fall within the outer limit range 597 during the occurrence of the episode. As shown in the graph 589, the local maximum rate of change in the episode 598 occurred between the current glucose data value 593 and the second most recently received glucose data value 594. Because the local maximum rate of change is recorded, a user may use this information to determine which events, if any, may or may not have contributed to jump in glucose values between these two readings.

Also shown on graph 589 is a matching window line 599 that represents a matching window time period. In certain embodiments, the matching window time period is a time period that starts at a predetermined amount of time prior to the detected start of the episode and ends when the episode ends. For example, as depicted in FIG. 5H, the matching window time period starts approximately 30 minutes prior to the start of the detected episode and ends at the same time as the episode. Although a 30 minute time period is specifically shown, it is contemplated that various other time periods may be selected by a user or healthcare provider.

As discussed above, the matching window may be used to automatically associate events, that occurred during the matching window time period, to the episode to enable a user or healthcare provider to ascertain which events may have caused, or were at least related to, the rapid increase or decrease in glucose levels. Such examples include other significant increases or decreases in glucose, episodes of high or low glucose, glucose alarm events, meal times, exercise periods, and the like. For example, if a user recorded an event, such as, for example, a meal at approximately 7:30 PM and the episode started at 7:50 PM, it may be determined by the user or healthcare provider that the particular meal eaten by the user was at least a factor in the episode starting. Thus, the user may take steps to prevent future episodes from occurring by avoiding similar foods.

FIG. 6 illustrates an exemplary menu screen 600 screen type according to embodiments of the present disclosure. Although the menu screen 600 shown in FIG. 6 is specific to a main menu, the user interface includes a number of menus and submenus corresponding to various functionalities and display screens. As such, it will be understood that all of the menus, functions, and display screens may be navigated in a way similar to the way described with reference to FIG. 6.

In certain embodiments, menu screen 600 may include a plurality of menu items. Specific examples include an alarm settings menu item, a reports menu item, an add events menu item, a status menu item and a settings menu item to name just a few. Although specific menu items in particular orders are shown and discussed, it is contemplated that a user may select various menu items and select the order of the menu items displayed in the menu screen 600. As stated above, each menu item may have corresponding submenus, display screens or functions that enable a user to customize the analyte monitoring device 200 for personal use. The menu screen may also contain menu items for clearing user settings and erasing user history. When implemented, the menu items for clearing user settings and erasing user histories may be password protected to prevent a user from unintentionally deleting the data on the analyte monitoring device 200.

In certain embodiments, the menu screen 600 is rendered on the display 210 in response to a user actuating an input button 220 (FIG. 2A). Referring to FIG. 3A above, to display the menu screen, the softkey button actuated is the input button 220 that corresponds to softkey button label 344 labeled "Menu." Although a specific softkey label 344 and corresponding input button 220 are mentioned, it is contemplated that the menu screen 600 may be accessed by actuating a pre-programmed button or a touch sensitive portion of the display 210 (FIG. 2A).

In certain embodiments, menu screen 600 includes a title portion 610 indicating the name of the current menu or submenu the user has navigated to as well as a list of menu items 640 available for the particular menu. For example, the list of menu items 640 shown in FIG. 6 includes a "Connect to Sensor" menu item, an "Alarms" menu item, a "Reports" menu item, and an "Add Event" menu item. A scroll indicator 620 is shown to indicate additional menu items are on the list but are not currently visible on the display 210. Such examples include a "Status" menu item, a "Settings" menu item and a "Manual Calibration" menu item. The scroll indicator 620 may also have a position indicator 625 to indicate a position on the menu. For example, as shown in FIG. 6, the position indicator 625 is located at the top of the scroll indicator 620. This shows that a selection indicator 630 is at the first menu item of the menu screen 600. As the selection indicator moves to various items in the list, the position indicator 625 moves along the scroll indicator 620 to indicate how far down the list of menu items the user has navigated. In one aspect, a processor of the analyte monitoring device 200 causes each of the menu items to change from a first color to a second color when the menu item is selected. For example, a first menu item that is selected may be a first color, while the remaining menu items are displayed in a second color.

In certain embodiments, the menu screen 600 is navigable using a scrolling device, such as jog wheel 230 (FIG. 2C), or by actuating an input button 220. In certain embodiments, wrap navigation may be used in which the user may scroll from the first item in the list directly to the last item in the list and vice versa. As the jog wheel 230 is actuated, the selection indicator 630 moves from one menu item to a next, or subsequent, menu item. For example, if the "Sensor" menu item is currently selected by the selection indicator 630, as the jog wheel 230 is actuated in a downward motion, the selection indicator 630 moves to the "Alarms" menu item.

When the selection indicator 630 highlights a desired menu item, a user actuates a softkey button having a corresponding softkey label such as, for example, right softkey label 650 or left softkey label 660. Continuing with the example, the right softkey label 650 may be labeled "Select" for selection of the currently highlighted menu item and the left softkey label 660 may be labeled "Home" which returns a user to the home screen, such as, for example, home screen 300. Other softkey labels may be used based on the various menu states of the menu. Such examples include softkey labels for "Next", "Done", "Accept", and "Cancel" to name a few. In certain embodiments, when a particular menu item is highlighted, selection of the menu item may be made by inwardly depressing the jog wheel 230. In yet other embodiments, the selection of the highlighted menu item may be made using a touch sensitive portion of the display 210.

When a selection of the menu item is made, a unique display screen is output on the display 210. In certain embodiments, the display screen is specific to each of the menu items 640. In certain embodiments, some menus have multiple status screens that are linearly arranged. Thus, data and status information may be viewed simply by actuating the jog wheel 230 or a softkey button having a corresponding softkey label (e.g., "Next") used for advancing through the various status screens of the menu. In certain embodiments, the system "remembers" the order in which the display screens were output on the display 210. Thus, a user may return to a previously viewed display screen by actuating a softkey button that functions as a "back" button. As such, previously viewed display screens may be output on the display 210 in reverse order.

In certain embodiments, each of the menu screens contains a number of menu items. Each menu item may have submenus having submenu items that correspond to various display screens of the analyte monitoring device 200. Although the menu items 640 in the menu screen 600 may be arranged in default settings, it is contemplated that a user may manually select various menu items 640 and display screens that are output on the main menu screen 600. As particular menus are accessed and as functions corresponding to the menus are utilized, the position of the corresponding menu items 640 in the menu screen 600 may move up or down the menu screen 600 based on frequency of use. For example, if the "Alarms" menu item 640 is selected more frequently than the "Connect to Sensor" menu item 640, the "Alarms" menu item 640 would be the first menu item 640 in the menu screen 600.

In certain embodiments, the menu screen 600 contains at least seven various submenus and/or display screens with each submenu and display screen having specific features or functionalities. It will be understood that navigation and selection of items on the various submenus and display screens described below may be accomplished in a similar manner as described above with respect to FIG. 6.

Connect to Sensor

The "Connect to Sensor" menu item enables a user to wirelessly connect to a sensor, such as sensor 101 (FIG. 1) described above and/or allows the user to ascertain whether the analyte monitoring device 200 (FIG. 2A) is connected to the correct transmitter and/or sensor (e.g., the transmitter and/or sensor of the user of the analyte monitoring device 200) before initiating transmitter communication and reception of analyte readings from the sensor. In certain embodiments, when the "Connect to Sensor" menu item is selected on the menu screen 600, the menu screen 600 linearly progresses to a sensor submenu 700 as shown in FIG. 7. The sensor submenu 700 includes a title portion 710 indicating the name of the submenu (e.g., Sensor Menu) as well as a list of menu items 740 available in the Sensor Menu. For example, the Sensor Menu includes a "Connect to Sensor" menu item and a "Calibration BG" menu item. In certain embodiments, the sensor submenu 700 also includes a scroll indicator 720 having a position indicator 725 that indicates a position of a selection indicator 730. In certain embodiments, the scroll indicator 720 and position indicator 725 are output on the display 210 only when the number of menu items displayed on the menu exceeds a predetermined number (e.g., 4). For example, if the menu screen has three menu items, the scroll and position indicators are not output on the menu screen. If the menu screen has five menu items, the scroll indicator and position indicator are output on the menu screen. Although the above example is given with respect to FIG. 7, it is contemplated that the scroll and position indicators for each of the various menu screens discussed herein may be displayed based on the number of menu items in the menu screen.

Referring back to FIG. 7, when the "Calibration BG" menu item is selected (e.g., by actuating a softkey button corresponding to the "Select" softkey label 750 when the "Calibration BG" menu item is highlighted by the selection indicator 730), a message screen is output on the display 210 (FIG. 2A) asking a user if calibration of the sensor is desired. If the user selects the option to proceed with the calibration, further instructions are output on the display 210. In certain embodiments, the message screen may also provide a time period in which the next calibration is needed and a grace period for calibration. Thus, if the user does not want to proceed immediately with the calibration, the user is put on notice of when the next calibration should occur.

When the "Connect to Sensor" menu item is selected (e.g., by actuating a softkey button corresponding to the "Select" softkey label 750 when the "Connect to Sensor" menu item 740 is highlighted by the selection indicator 730), an instruction screen is output on the display instructing a user told to hold the analyte monitoring device 200 next to the sensor. If a sensor is detected within range of the analyte monitoring device 200, a progress alarm is output by the analyte monitoring device 200 to indicate that a connection between the sensor and the analyte monitoring device 200 was made. When the connection between the analyte monitoring device 200 and the sensor is established, a message screen is output on the display 210 that prompts a user to enter in a sensor code that corresponds to a code of the actual sensor the user is using. As with other alarms or auditory notifications described herein, the tone or sound of the progress alarm may be selected by a user. It is also contemplated that additional sounds or tones, such as music, recorded speech, and the like, may be downloaded, stored on the analyte monitoring device 200 and used as alarms.

In certain embodiments, if a connection with the sensor is not established within a predetermined amount of time, a second instruction screen is output on the display 210 indicating that a connection between the sensor and the analyte monitoring device 200 was not established. An audible alarm and/or vibration may also be output to indicate that a sensor was not found by the analyte monitoring device 200. A user may navigate away from the second instruction screen using the softkey buttons such as input buttons 220 having corresponding softkey labels or by using secondary button 240 to return to a previous menu or display screen. If a connection is not established between the sensor and the analyte monitoring device 200, a second alarm and corresponding alert screen may be output by the analyte monitoring device 200 indicating that continuous glucose data from the sensor is not available. If the continuous glucose data is unavailable for a predetermined amount of time (e.g. 1 hour) additional alarms and display screens may be output on the display 210 to put the user on notice that data is not currently being received by the analyte monitoring device 200. To return to menu screen 600, a user may actuate a softkey button corresponding to the "Home" softkey label 760. Further details regarding connection to a sensor and corresponding alert screens are illustrated in FIG. 26 described below.

Alarm Settings

An "Alarm Settings" submenu 800 is shown in FIG. 8 according to embodiments of the present disclosure. The "Alarm Settings" submenu 800 is provided to a user when the "Alarm Settings" menu item is selected from the menu screen 600. In certain embodiments, the "Alarm Settings" submenu 800 includes a title portion 810 indicating the name of the submenu as well as a list of menu items 840 available in the submenu. In certain embodiments, the "Alarm Settings" submenu 800 also includes a scroll indicator 820 and a position indicator 825 that indicates a position of a selection indicator 830. The "Alarm Settings" submenu enables a user to select alarm tones, alarm volumes, frequency of alarms as well as vibration settings for the analyte monitoring device 200. The "Alarm Settings" menu screen 800 may include menu items 840 with each menu item having its own functionality or display screen. For example, the additional alarm settings menu items may include an "Audio/Vibrate" item, a "Mute Alarms" menu item, a "Glucose Alarms" menu item, a "Tones" menu item, a "Snooze Setup" menu item and a "Charging Setup" menu item. Although specific titles have been used, other titles may be used to indicate similar or additional functionality with respect to alarms. In certain embodiments, selection of a menu item 840 is made by actuating a softkey button corresponding to the "Select" softkey label 850. In certain embodiments, a user may return to the menu screen 600 or to home screen 300 (FIG. 3A) by actuating a softkey button corresponding to the "Home" softkey label 860.

The "Audio/Vibrate" menu item enables a user to select various alarm settings. These settings may include the type of alarm, for example, audio only, vibration only, or audio and vibration. In certain embodiments, the user may also select an option in which a vibratory or tactile alert trumps an audible setting for individual alarms. The "Alarm Settings" menu item may also include an option to adjust overall volume level of the alarms of the analyte monitoring device 200. The overall volume level may be user selectable with options for high, medium and low.

Additionally, the "Alarm Settings" may also include volume settings for progress tones. In certain embodiments, progress tones are sounds output from the analyte monitoring device 200 to notify a user about the progress and status of specific steps, such as, for example connecting to a sensor. The volume setting may include high, medium, low, and off.

When volume and/or vibration setting selections are made, (e.g., audio and vibration selected as the type of alarm), a sample alarm and/or vibration is output from the analyte monitoring device 200 to the user. Once selected, the user may confirm the selection by actuating a softkey button or by touching an area on the touch sensitive display. In certain embodiments, the user may choose a different sound and/or vibration for each alarm. As discussed above, this setting may be depicted on a home screen by an icon, such as audio/vibratory settings icon 332 (FIG. 3A).

FIG. 9 shows an exemplary "Mute Alarms" display screen 900 that is output on the display 210 (FIG. 2A) when the "Mute Alarms" menu item is selected from the "Alarm Settings" menu screen 800 (FIG. 8). The "Mute Alarms" display screen 900 includes a title portion 910 as well as an "Accept" softkey label 920. The "Mute Alarms" display screen 900 presents a user with different muting options to mute alarms that are associated with various alert conditions. For example, one alarm may correspond to a low battery alert condition and another alarm may correspond to an impending hypoglycemia condition. To mute alarms, the user may be presented with a screen having a selectable mute duration from 1 hour up to 12 hours in one hour increments. If a user mutes any of the alarms for more than 12 hours, the user may be required to turn off each alarm one at a time. In certain embodiments, once the selected mute time has elapsed, the alarms return to the original settings (e.g. a 1 hour setting). In certain embodiments, although some alarms are muted, such as, for example, alarms corresponding to medium urgency alerts described below, vibratory and onscreen text notifications may still be output on the display 210 although the audible notification will be muted. In yet other embodiments, some alerts or alarms may not be muted, such as, for example, high urgency alerts such low glucose alarms. In certain embodiments, some alarms may be muted for predetermined periods of time regardless of user input. When an alarm is muted, the user is presented with an option to accept (e.g., by actuation of a softkey button corresponding to the "Accept" softkey label 920) the mute setting and subsequently confirm the mute setting. If the user wishes to unmute the alarms, the user is presented with an unmute option and then may be prompted, via a display screen, to confirm the unmute action.

The "Glucose Alarms" menu setting enables a user to specify when various alarms of the analyte monitoring device 200 (FIG. 2A) are active. The options presented to a user may specify the time of day that day alarms begin (e.g., 8:00 AM) and a time of day that the night alarms begin (e.g., 9:00 PM). In certain embodiments, the day alarm and the night alarm cannot overlap. Additionally, the day and night alarms may have different settings corresponding to how often the alarms are output and/or under what conditions the alarms are output (e.g. low and high glucose thresholds). For example, the alarms setting may specify that alarms are output during the day more frequently than alarms that are output at night. In certain embodiments, the time of the day alarm and the time of the night alarm may be user adjustable and selectable. In one aspect, day alarms may be active while night alarms are inactive.

Figure 10:
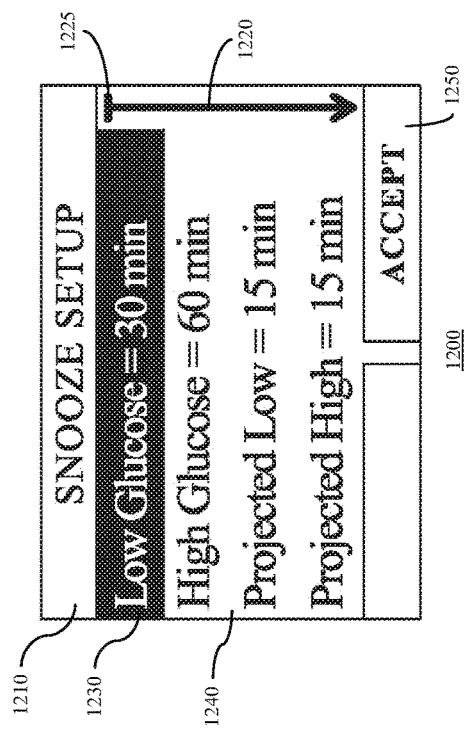
FIG. 10 illustrates an exemplary glucose alarm threshold display screen according to embodiments of the present disclosure.

In certain embodiments, when the day alarm time has been set, the menu linearly progresses to a "Glucose Alarm" threshold screen in which a user may select varying glucose threshold levels at which various alarms will sound for low glucose levels, high glucose levels, projected low glucose levels and projected high glucose levels. An exemplary "Glucose Alarm" threshold display screen 1000 is shown in FIG. 10. In certain embodiments, the "Glucose Alarm" display screen 1000 includes a title 1010 and a selection indicator 1020. The "Glucose Alarm" display screen 1000 also includes a "Low Glucose" threshold level menu item 1030, a "High Glucose" threshold level menu item 1040, a "Projected Low" menu item 1050, and a "Projected High" menu item 1060. Each menu item above may be selected using a jog wheel 230 (FIG. 2C) or other selection mechanism. As shown in FIG. 10, a low glucose threshold level 1030 may have a preset low threshold (e.g., 80 mg/dL) and the high glucose threshold level 1040 may have a preset high threshold (e.g., 250 mg/dL). In certain embodiments, the low glucose threshold level may be selected by a user or healthcare provider from a predetermined range (e.g., 60-119 mg/dL) and the high glucose threshold level may be selected by a user or healthcare provider from a second predetermined range (e.g., 120-300 mg/dL). Each of the high and low threshold levels may be changed by the user or healthcare provider by highlighting the menu item using the selection indicator 1020 and inwardly pressing the jog wheel 230. The user may then scroll through the desired threshold level for the selected menu item.

In certain embodiments, a value for the "Projected Low" item 1050 and value for the "Projected High" item 1060 may be set in terms of time t for each of the day alarms and the night alarms. The projected low value and the projected high value represent how much notice a user wants before an alert screen or alarm is output to notify a user of projected glucose values that will exceed high or low glucose threshold limits. The time values may be set by selecting the particular menu item and actuating the jog wheel 230 as described above. In certain embodiments, the time values t may be in 10 minute increments ranging from 10 minutes up to 30 minutes. In other embodiments, varying time increments may be used. When desired settings are complete, the user may actuate a softkey button corresponding to the "Accept" softkey label 1070 and be returned to a previous menu or to a home screen, such as, for example, home screen 300 (FIG. 3A).

Figure 11:
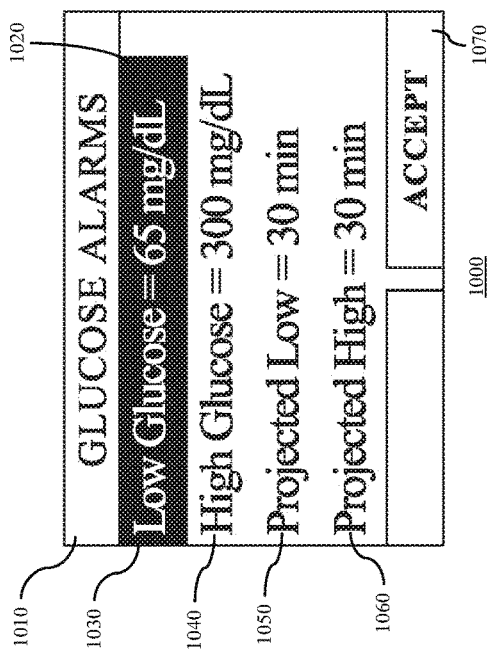
FIG. 11 illustrates an exemplary alarm tones display screen according to embodiments of the present disclosure.

FIG. 11 illustrates an exemplary "Tones" menu display screen 1100 that enables a user to select various tones for each of the low glucose threshold level, the high glucose threshold level, the project low and the project high settings. When the user has selected desired tones for each of the low glucose threshold level, the high glucose threshold level, the project low and the project high settings, the user may accept the settings by actuating a softkey button corresponding to the softkey label "Accept" 1160 or may navigate to a second "Tones" display screen by actuating a softkey button corresponding to the softkey label "Next" 1150.

In certain embodiments, the "Tones" menu display screen 1100 includes a title portion 1110 indicating the name of the submenu as well as a list of available menu items 1140. In certain embodiments, the "Tones" display screen 1100 also includes a scroll indicator 1120 and a position indicator 1125 that indicates a position of a selection indicator 1130. The "Tones" display screen 1100 displays different tones that may be used for each alarm of the analyte monitoring device 200 (FIG. 2*a*). In certain embodiments, additional tones or sounds may be downloaded from the internet and stored on the analyte monitoring device 200. The "Tones" menu display screen 1100 also gives users the option to turn each alarm on or off depending on the preference of the user, such as shown in FIG. 11 (e.g., the "Projected High" alarm is off).

In certain embodiments, data loss alarm tones and system alarm tones may also be selected by a user in the "Tones" menu display screen 1100. The data loss and system alarm tones may be controlled, muted and turned on or off much like the other tones described above. The data loss alarm indicates that glucose data is no longer available (e.g., the glucose data has been deleted from the memory of the analyte monitoring device 200) or glucose data has not been received from the sensor 101 for a predetermined amount of time (e.g., 10 minutes). In certain embodiments, if data loss continues for the predetermined amount of time, additional tones may be output and/or display screens displayed that indicate the data loss condition. In certain embodiments, data loss alarms must be activated when glucose alarms are set. Thus, if a user sets an alarm tone for glucose levels exceeding a predetermined threshold, the user must also select/activate an alarm tone for data loss. Regarding system alarms, system alarms are output to notify a user of system events such as a low battery or an upcoming need for calibration. As with data loss alarms, if a system alarm goes unheeded for a predetermined amount of time, additional tones and display screens may be presented to the user to further notify the user of the condition of the various components of the system.

Figure 12A:
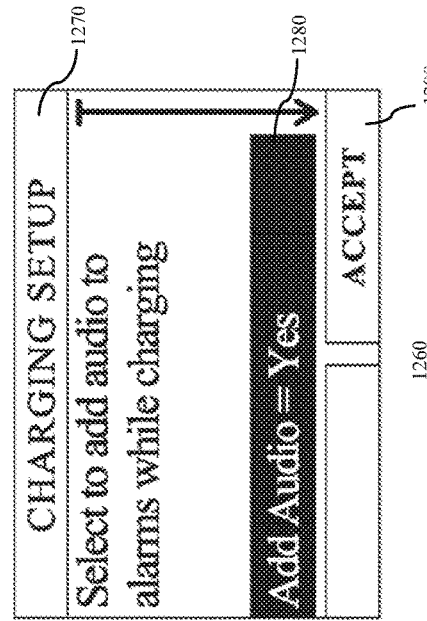
FIG. 12A illustrates an exemplary snooze setup display screen according to embodiments of the present disclosure.

FIG. 12A shows a "Snooze Setup" display screen 1200 according to embodiments of the present disclosure. In certain embodiments, the "Snooze Setup" display screen 1200 includes a title portion 1210 indicating the name of the display screen as well as a list of available menu items 1240. In certain embodiments, the "Snooze Setup" display screen 1200 also includes a scroll indicator 1220 and a position indicator 1225 that indicates a position of a selection indicator 1230. The "Snooze Setup" display screen 1200 enables a user to select different snooze settings for the alarms of each of the low glucose threshold level, the high glucose threshold level as well as projected high and low glucose levels as described above. When the settings of the user are selected, a user may actuate a softkey button corresponding to the "Accept" softkey label 1250 to accept the snooze settings.

In certain embodiments, the snooze settings are in the range of 15 minutes to 60 minutes in 5 minute increments for a low glucose threshold level and the snooze settings for high glucose threshold level are between 15 minutes to 240 minutes in 5 minute increments. In certain embodiments, if an alarm is repeatedly "snoozed", the command to snooze the alarm is disregarded by the processor of the analyte monitoring device 200 and the alarm is continually outputted to notify the user of the condition or impending condition. In another embodiment, a notification (e.g., icon, message, etc.) of the alarm is output on the display 210 as the home screen the next time the user interface of the analyte monitoring device 200 is activated.

Figure 12B:
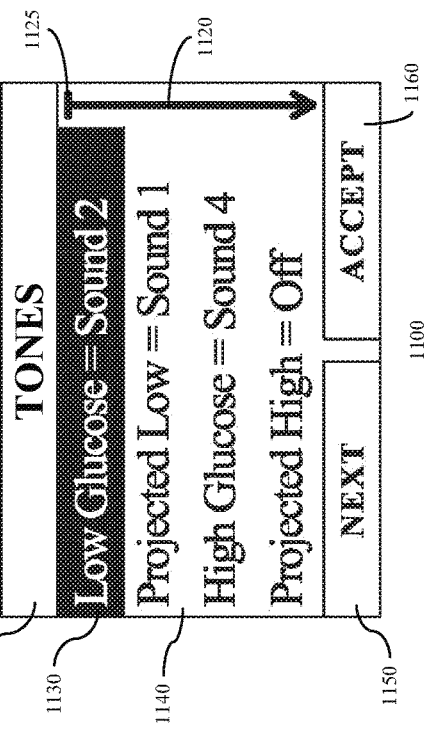
FIG. 12B illustrates an exemplary charging setup display screen according to embodiments of the present disclosure.

FIG. 12B is an exemplary "Charging Setup" display screen 1260 according to embodiments of the present disclosure. In certain embodiments, the "Charging Setup" display screen 1260 includes a title portion 1270 indicating the name of the display screen as well as a selection indicator 1280 that enables a user to select whether audio alarms are activated when the analyte monitoring device 200 is charging. In certain embodiments, a user may select "no" if the user wants to disable audio alarms while the analyte monitoring device 200 is charging. In certain other embodiments, if the alarm settings of the analyte monitoring device 200 are set to vibration only or mute as described above with respect to FIG. 8, selecting "yes" in the "Charging Setup" display screen 1260 causes the audio of the alarms to be output only when the analyte monitoring device 200 is charging. When the analyte monitoring device 200 has been charged and is unplugged from an external power supply, the audio for the alarms is disabled. Once the user has made the charging setup selection, a user may actuate a softkey button corresponding to the "Accept" softkey label 1290 to accept the charging setup setting.

Figure 13:
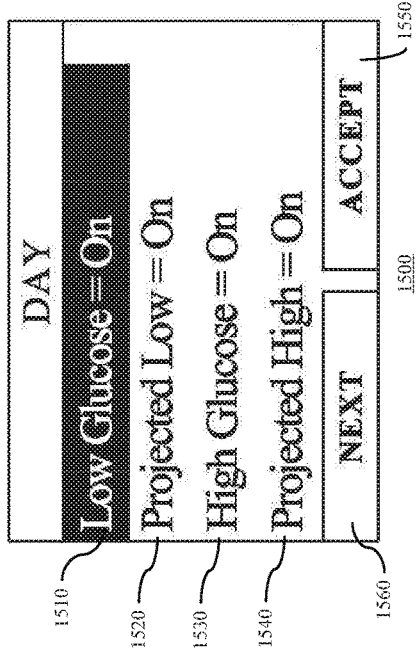
FIGS. 13-16 illustrate a set of exemplary set alarm profile display screens according to embodiments of the present disclosure.

FIG. 13 is an exemplary "Alarm Profile" display screen 1300 according to embodiments of the present disclosure. As with other display screens described herein, the "Alarm Profile" display screen 1300 includes a title portion 1310 indicating the name of the display screen as well as a list of available menu items 1340. In certain embodiments, the "Alarm Profile" display screen 1300 also includes a scroll indicator 1320 and a position indicator 1325 that indicates a position of a selection indicator 1330. The "Alarm Profile" display screen 1300 enables a user to select (e.g., by actuating a softkey button corresponding to the "Select" softkey label 1350), view and edit (e.g., by actuating a softkey button corresponding to the "View/Edit" softkey label 1360) various alarm profiles that correspond to different activities of the user. For example, a first alarm profile may correspond to exercise activities of the user while a second alarm profile may correspond to eating or sleeping activities of the user.

In certain embodiments, each alarm profile has parameter levels associated therewith, such as, for example, a low glucose level, a projected low glucose level, a high glucose level and a projected high glucose level. The parameter levels for each alarm profile may be viewed and set similar to the glucose alarm threshold screen shown and described with respect to FIG. 10.

Figure 14:
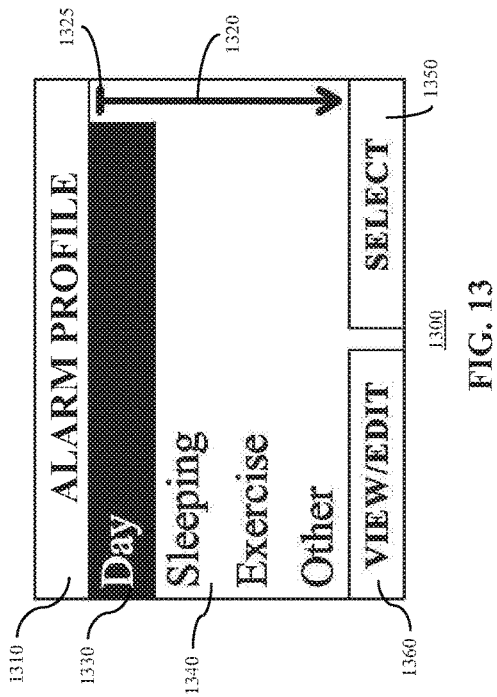

Each profile also has a low glucose parameter 1410, a high glucose parameter 1430, a projected low glucose parameter 1420 and a projected high glucose parameter 1440 such as displayed in the "Day" display screen 1400 in FIG. 14. In certain embodiments, values for each of the low glucose parameter 1410, the high glucose parameter 1430, the projected low glucose parameter 1420 and the projected high glucose parameter 1440 may be adjusted by a user. When the user has selected the desired values for each parameter, the user may accept the changes by actuating a softkey button corresponding to the "Accept" softkey label 1450. Further, the user may navigate to an additional display screen, such as, for example, display screen 1500 (FIG. 15) by actuating a softkey button corresponding to the "Next" softkey label 1460.

Figure 15:
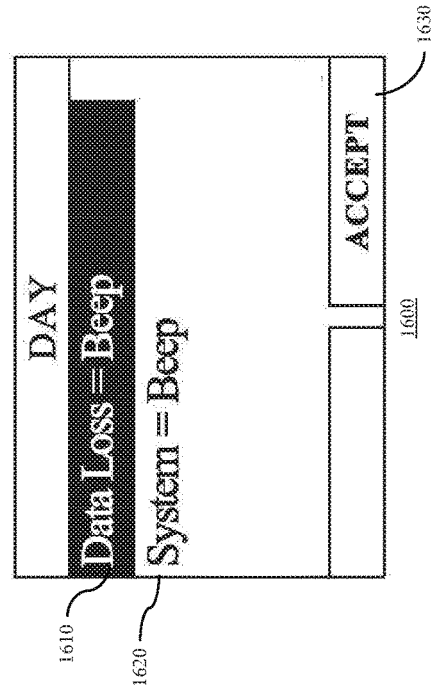
Figure 16:
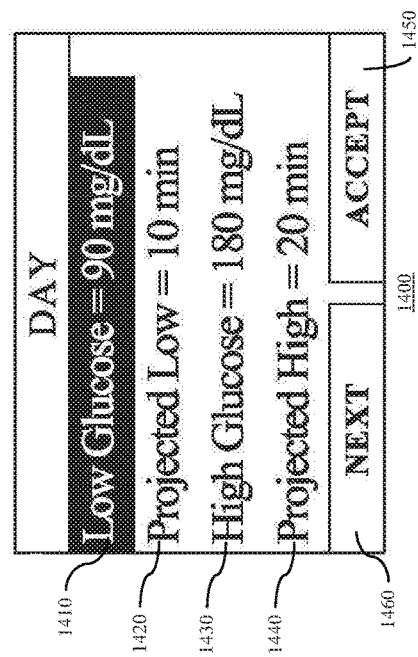

Additionally, each profile also has parameters corresponding to whether alarms for low glucose 1510, high glucose 1530, projected low glucose 1520 and projected high glucose 1540 are turned on or off as shown in display screen 1500 of FIG. 15. When the user has selected the desired values for each of these parameters, the user may accept the changes by actuating a softkey button corresponding to the "Accept" softkey label 1550. Further, the user may navigate to an additional display screen, such as, for example, display screen 1600 (FIG. 16) by actuating a softkey button corresponding to the "Next" softkey label 1560. When creating a profile, a user may also select alarm tones for data loss 1610, in which tones or alarms are output when glucose data is no longer available or has not been received, and/or tones for system notifications 1620, such as low battery events and calibration events, and accept the settings by actuating a softkey button corresponding to the "Accept" softkey label 1630 such as shown on display screen 1600 of FIG. 16.

Each profile may also include specific alarm presentation characteristics such as alarm tone and/or volume setting. For example, if the user selects a "sleeping" profile, the parameters of the alert may include a loud hypoglycemia alarm and a very high hyperglycemia threshold. If the user selects an eating profile, the parameters of the alert may only include a high hyperglycemia threshold. The user may customize the setting of each profile or create a new profile to define a commonly used set of alarm parameters. Thus, the user does not need to change each alarm setting based on various activities. In certain embodiments, a processor of the analyte monitoring device 200 may track an active profile state which contains modifications to a defined profile that are made on the fly by the user and implement those changes to similarly defined profiles.

Reports

When the "Reports" menu item is selected from the menu screen 600 (FIG. 6) a "Reports" submenu is displayed according to embodiments. The "Reports" submenu enables a user to view glucose history by selecting a "Glucose History" submenu item, event history by selecting an "Event History" submenu item, a timeline graph by selecting a "Timeline Graph" submenu item, continuous glucose monitoring statistics by selecting a "CGM Statistics" submenu item, and blood glucose statistics by selecting a "BG Statistics" submenu item.

In certain embodiments, selection of "Glucose History" submenu item enables a user to view past and continuous glucose information in various time periods. These time periods may include 10 minute time periods, 60 minute time periods, or 120 minute time periods. When a particular time period for the glucose history is selected (e.g., a 60 minute time period), a user may view continuous glucose monitoring history for specific days in the time increment specified.

The "Glucose History" submenu also enables a user to view the blood glucose history of the user. The blood glucose history display screen outputs the time and date of each blood glucose reading as well as indicating, via text, colors, icons, or combinations thereof, as to whether the reading was high or low. A jog wheel, such as, for example, jog wheel 230 (FIG. 2C) allows a user to chronologically advance to newer or older records in the user's history.

In certain embodiments, the "Glucose History" submenu also includes a "Glucose Alarms" display screen which allows a user to view recent alarms, including the type of alarm, that have been output based on glucose levels exceeding predetermined threshold levels such as described above. Such alarm types may include alarms for low glucose levels, alarms for high glucose levels as well as alarms for projected high and low glucose levels. The jog wheel 230 may also be used to chronologically display various records stored in a memory of the analyte monitoring device 200.

The "Event History" submenu item enables a user to review, enter, and/or edit various events the user has participated in during a specified time period. Such events include: 1) the administration of insulin as well as the type (e.g., short-acting, rapid-acting, long-acting, pre-mix intermediate, etc.) and amount of insulin injected (e.g., 0.00-99.50 U); 2) food eaten, including the meal and the total number of carbohydrates (e.g., 0-350 g); 3) exercise, including the type of exercise (e.g., aerobics, walking, jogging, running, swimming, biking, weights, other, etc.), the duration (e.g., 1-12 hours) and the intensity of the exercise (e.g., high, medium, low, none); 4) a state of health including editable fields describing the state of health (e.g., normal, cold, sore throat, infection, tired stress, fever, flu, allergy period, dizzy, feel low, feel high etc.); and 5) a custom field in which a user may view customized events that affected or may have affected glucose levels.

In certain embodiments, when the "Timeline Graph" submenu item is selected by a user, a display screen, similar to the timeline graph 400 of FIG. 4A, is output on the display

210 (FIG. 2A). The timeline graph displays glucose value data points versus a time of day for various periods of time. The timeline graph may also be configured to display glucose values that fall within a user selectable target range. For example, a user may choose to have the timeline graph display only glucose values that fall within a range of 100 mg/dL-160 mg/dL within a given period of time. Although a specific range has been discussed, it is contemplated that any range of values may be selected and displayed. As stated above with reference to FIG. 4A, the periods of time may be user selectable to show a greater or fewer amounts of time. The jog wheel 230 may be used to chronologically navigate to earlier periods of time or later periods of time represented on the timeline graph.

Figure 17A:
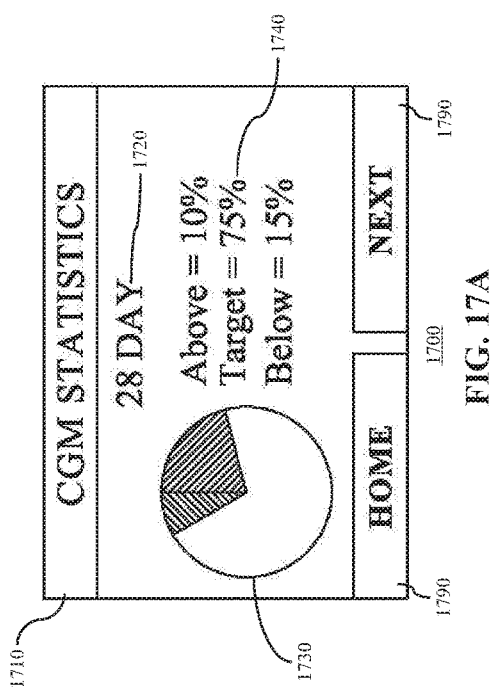
FIGS. 17A-17C illustrate exemplary Continuous Glucose Monitoring (CGM) statistic display screens according to embodiments of the present disclosure.
Figure 17B:
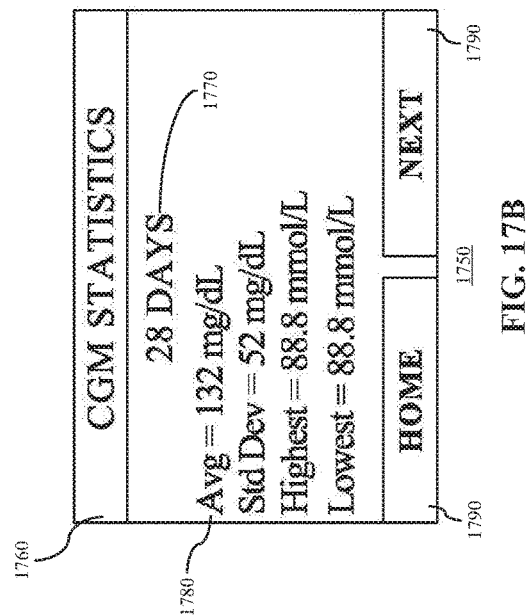

FIGS. 17A and 17B illustrate exemplary "CGM Statistics" (continuous glucose monitoring) display screens 1700 and 1750 according to embodiments. In general, each of the "CGM Statistics" display screens 1700 and 1750 allow a user to view information about continuous glucose readings received from a sensor, such as, for example sensor 101 (FIG. 1). In certain embodiments, the "CGM Statistics" display screens 1700 and 1750 also include a plurality of softkey labels 1790 (labeled "Home" and "Next") to assist a user in navigating through various screens and submenus.

In certain embodiments, "CGM Statistics" display screen 1700 includes a title portion 1710 to indicate the type of data the user is currently viewing. A user selectable time period display 1720 is also output on the display screen 1700 to indicate the time period of the displayed statistics. In certain embodiments, the time period is adjustable by selecting the time period display 1720 and actuating the jog wheel 230 (FIG. 2C). CGM statistics may be viewed for 1, 3, 7, 14, 21, or 28 day periods.

In certain embodiments, "CGM Statistics" display screen 1700 also includes a pie chart 1730 and a corresponding key 1740. The information displayed on the pie chart 1730 and corresponding key 1740 includes a percentage of time the user's glucose level was above a target threshold amount, a percentage of time the user's glucose level was within the target threshold amount, and a percentage of time the user's glucose level was below the target threshold amount. Although a pie chart is specifically mentioned and shown, it is contemplated that other charts and graphs, such as bar graphs may be used to display similar data. Additionally, the pie chart 1730 and the corresponding key 1740 may be color coded to enable a user to easily identify which percentages correspond to which glucose levels. For example, a first line of text of the key 1740 and/or a first portion of a pie chart 1730 may be displayed in green to indicate the user was within the target range for 75% of the time, a second line of text of the key 1740 and/or a second portion of a pie chart 1730 may be displayed in yellow to indicate the user was below the target range for 15% of the time, and a third line of text of the key 1740 and/or a third portion of the pie chart 1730 may be displayed in purple to indicate the user was above the target range 10% of the time for a given time period.

FIG. 17B shows an additional "CGM Statistics" display screen 1750 according to embodiments of the present disclosure. "CGM Statistics" display screen 1750 includes a title 1760 to indicate to a user the type of data displayed. A user selectable time period display 1770 is also displayed indicating the time period of the displayed statistics. In certain embodiments, the time period is adjustable by selecting the time period display 1770 and actuating the jog wheel 230 (FIG. 2C). CGM statistics may be viewed for 1, 3, 7, 14, 21, or 28 day periods. "CGM Statistics" display screen 1750 also displays a list of statistics 1780 such as an average continuous glucose level for the selected time period, the standard deviation for the selected time period, a highest continuous glucose level for the selected time period, and a lowest continuous glucose level for the selected time period. In certain embodiments, additional statistics for the selected time period may be displayed, such as, for example, a low/day, high/day, projected low/day and projected high/day.

Figure 17C:
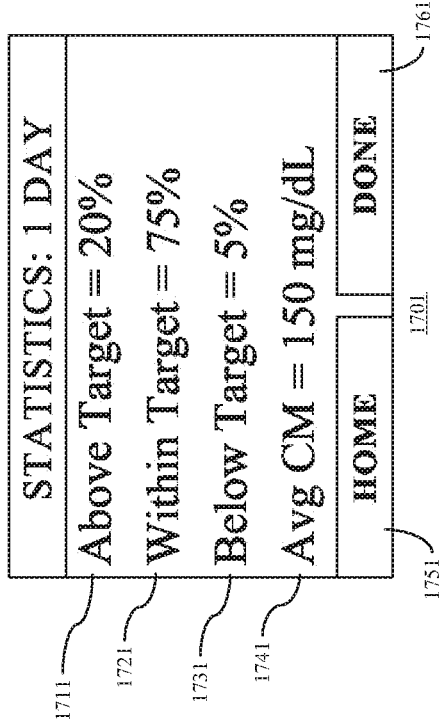

Another embodiment of a "CGM Statistics" display screen 1701 is shown in FIG. 17C in which a user may scroll through statistical information about continuous glucose readings such as, for example, percentage of time above a target threshold 1711, percentage of time within the target threshold 1721, a percentage of time below the target threshold 1731, and an average glucose value 1741 to name a few. When a user has finished viewing the "CGM Statistics" display screen 1701, the user may return to a home screen, such as, for example information mode home screen 300 (FIG. 3A) by actuating a softkey button corresponding to the "Home" softkey label 1751 or may return to a previously viewed display screen by actuating a softkey button corresponding to the "Done" softkey label 1761.

In certain embodiments, a "BG Statistics" display screen enables a user to scroll through historical information corresponding to blood glucose readings. Such information may be output on the display 210 (FIG. 2A) as a pie chart, text, graphic or combination thereof in a similar fashion to the "CGM Statistics" display screen shown in FIG. 17A and described above. In certain embodiments, the information displayed on the "BG Statistics" display screen indicates a number of days or the number of times the user's blood glucose levels were above a target threshold amount, within the target threshold amount, and below the target threshold amount.

In certain embodiments, other statistics may be available on the "BG Statistics" display screen such as, for example, an average blood glucose level, the standard deviation, a highest blood glucose level, and a lowest blood glucose level. These statistics may be displayed in a similar fashion to the "CGM Statistics" display screen shown in FIG. 17B and described above. This "BG Statistics" display screen may also display the total number of blood glucose readings in a given time period, an average of the number of blood glucose readings per day in the given time period, as well as above/day statistics and below/day statistics. Each of the above mentioned statistics may be viewed for various time periods. For example, the given time periods may be selected from 1, 3, 7, 14, 21, or 28 day periods.

Add Event

When the "Add Event" menu item is selected, a submenu is output on the display 210 that enables a user to enter in various events the user has participated in during specific time periods. Such events include: 1) the administration of insulin as well as the type (e.g., short-acting, rapid-acting, long-acting, pre-mix intermediate, etc.) and amount of insulin injected (e.g., 0.00-99.50 U); 2) food eaten, including the meal and the total number of carbohydrates (e.g., 0-350 g); 3) exercise, including the type of exercise (e.g., aerobics, walking, jogging, running, swimming, biking, weights, other, etc.), the duration (e.g., 1-12 hours) and the intensity of the exercise (e.g., high, medium, low, none); 4) a state of health including editable fields describing the state of health (e.g., normal, cold, sore throat, infection, tired stress, fever, flu, allergy period, dizzy, feel low, feel high etc.); and 5) a custom field in which a user may view customized events that affected or may have affected glucose levels. Once an event has been entered, an event icon may be displayed at a point on the timeline graph 400 (FIG. 4A) at the current continuous monitored glucose level corresponding to the current time of the analyte monitoring device 200. In one aspect, if the user failed record an event at the time it took place, the user may be able to manually select a time period in which the event took place and it is recorded on a graph at the time period selected by the user.

Status

Figure 18:
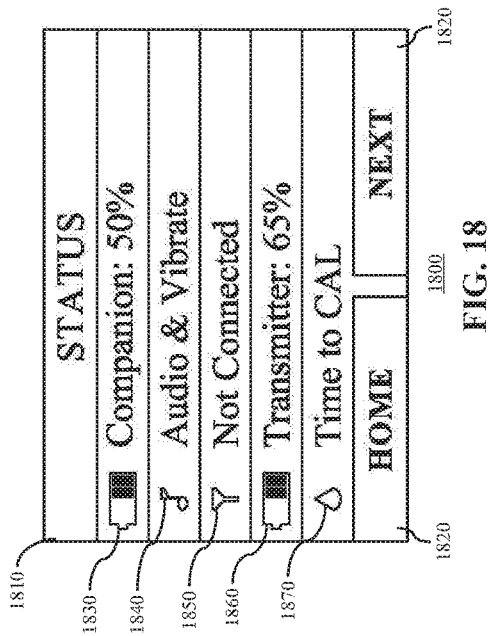
FIG. 18 illustrates an exemplary status display screen according to embodiments of the present disclosure.

FIG. 18 illustrates an exemplary "Status" display screen 1800 according to embodiments of the present disclosure. The "Status" display screen 1800 includes iconic representations of the status of various components of the analyte monitoring device 200. As with other display and menu screens, "Status" display screen 1800 includes a title portion 1810 and a plurality of softkey labels 1820 (labeled "Home" and "Next") to assist a user in navigating to and from the "Status" display screen 1800. Although two softkey labels 1820 are shown, it is contemplated that any number of softkey labels may be displayed on the "Status" display screen 1800.

In certain embodiments, the "Status" display screen 1800 includes various icons and corresponding text about the status of various components of the analyte monitoring device 200 (FIG. 2A) and/or the analyte monitoring system 100 (FIG. 1). The icons and corresponding text may include a battery power icon 1830 that shows available battery power in the analyte monitoring device 200, audio and vibrating settings icon 1840, a wireless connection status icon 1850 that indicates the connection status between the analyte monitoring device 200 and the transmitter, such as, for example transmitter unit 102 (FIG. 1), a transmitter battery charge icon 1860 that indicates the battery power remaining in the transmitter and a calibration status icon 1870. Each icon may have corresponding text to indicate what the icon represents.

The "Status" display screen 1800 may also include additional display screens that display the status of the various components of the analyte monitoring system 100 and/or the analyte monitoring device 200. For example, the user may be provided sensor information, such as, the date and time of the next calibration. This display screen may also indicate a calibration grace period available to the user. The user may also be notified of the life remaining on the current sensor as well as the date and time the current sensor is set to expire. Although this information is provided in the status screen, it is contemplated that this information may be presented on a home screen, such as information mode home screen 300 (FIG. 3A).

The "Status" display screen 1800 may also display the amount of time that has elapsed since the analyte monitoring device 200 received updated data from the sensor. Additionally, the "Status" display screen 1800 may display information regarding the status of the sensor. Examples include, a last reset, sensor errors, calibration failed indicator and the reasons for each (e.g., temperature too high, temperature too low etc.). In certain embodiments, the serial number and type of the transmitter may be displayed on the "Status" display screen 1800 as well as a serial number and software versions of the analyte monitoring device 200. The serial number of the analyte monitoring device 200 and/or the transmitter may be displayed using numbers, letters, symbols, or a combination thereof.

Settings

The "Settings" menu type may include various display screens to assist a user in changing various settings of the analyte monitoring device 200. Examples include a "Time and Date" display screen, a "Display" settings display screen, a "Glucose Targets" display screen, a "Self Test" display screen and a "Training" display screen. The "Time and Date" display screen enables a user to adjust the time and date displayed on the user interface. The "Display" settings display screen provides a user with a number of different options including a language setting, a timeout setting and a decimal format setting. The language setting enables a user to select at least 11 different languages (e.g., English, Spanish, German, Dutch, Portuguese etc.) of the text displayed on the display 210 the analyte monitoring device 200. The timeout setting enables a user to select a period of inactivity, from 15 seconds to 120 seconds, until the display 210 shuts off and/or the analyte monitoring device 200 enters a sleep mode. Upon exiting the sleep mode, such as, for example, by a user actuating a softkey button or touching a touch sensitive display, a home screen is output on the display 210 of the analyte monitoring device 200. In one aspect, when exiting the sleep mode, the display screen that was output on the display 210 prior to entering the sleep mode may be output on the display 210. In certain embodiments, the decimal setting enables a user to select a decimal format of either X.X or X,X.

The "Glucose Target" display screen enables a user to adjust the upper and lower target glucose amounts displayed on graphs such as, for example lower glucose target indicator 312 (FIG. 3A) and an upper glucose target indicator 314 (FIG. 3A), and are used to calculate a user's statistics reports. In certain embodiments, the "Glucose Target" display screen may be locked or password protected to prevent unauthorized or unintentional alteration of the glucose target range.

In certain embodiments, a "Self Test" display screen enables a user to select and run a self test mode in which the analyte monitoring device 200 automatically self tests whether various components of the analyte monitoring device 200 are working properly. Such components include the display, the speaker, the memory, the vibratory indicator, and the strip port light. After each successive test, the results may be audibly and/or visually output to a user. Although specific self tests have been mentioned, it is contemplated that additional self tests related to other components of the analyte monitoring device 200 may be performed.

In certain embodiments, the "Settings" menu type may also include a "Training" display screen in which a user may select to enter a training mode. The training mode is provided to assist a user in becoming familiar with the analyte monitoring device 200 and the various alert screens or display screens that may be output on the display 210 analyte monitoring device 200. As such, preloaded data may be used to trigger alarms and/or populate graphs thus giving a user firsthand experience in how the analyte monitoring device 200 operates and what conditions trigger the various alarms and alerts. Additionally, battery life of the analyte monitoring device 200 may be extended for a predetermined amount of time as some capabilities (e.g., wireless capabilities) and/or components of the analyte monitoring device 200 may be deactivated during training mode.

In certain embodiments, access to the training mode may be protected by a password to prevent unauthorized or unintentional access by a user. In another embodiment, the training mode may be freely accessed by the user but various features and options of the training mode, such as masking and unmasking data, may be password protected. During training mode a user may have an option in which the display 210 of the analyte monitoring device 200 will not time out for a user selectable period of time. In training mode a user may also erase glucose related data and reset user settings or user logs of the analyte monitoring device 200.

In training mode, a user may be able to select various training options. For example, a first option may correspond to setting event data icons on a graph such as event data icons 318 (FIG. 3C). The training mode may contain a simulation of various glucose levels and how each activity may affect subsequent glucose readings and data display. A second type of training mode may correspond to setting up various profiles based on user activities such as described above. Regardless of which training mode is selected, when the training is complete, the user may erase all training data from the analyte monitoring device 200.

In certain embodiments, training mode may also randomly select alarms and/or display screens from a set of predetermined alarms and display screens that a user is most likely to encounter when using the analyte monitoring device 200, such as, for example a low glucose alarm display screen. When the low glucose alarm display screen is output on the display 210, a message screen may be output on the display 210 instructing the user on how to proceed to deactivate the alarm and how to enter event history on a graph if desired.

In another embodiment, the training mode may receive real time data from a transmitter and perform functions as if in "normal" mode. At various points in the training mode, various display screens may be output on the display 210 instructing a user on what functions or display screens may be helpful to the user based on the data received. For example, if a glucose data value is received that is above or below a target threshold, the user may be prompted, via a display screen, to navigate to an alarms screen or a glucose level threshold display screen. The display screen may also contain written text or visual indicators instructing the user how to navigate to the suggested display screen.

When in training mode, a user may also choose to mask and/or unmask data corresponding to continuous glucose readings and blood glucose readings. In certain embodiments, when data from either continuous glucose readings or blood glucose readings is masked, corresponding alarms for each of the readings are deactivated. In certain other embodiments, when data is masked, certain menu items and/or display screens associated with the masked data may be deactivated.

Manual Calibration

In certain embodiments, the menu screen 600 (FIG. 6) may also include a "Manual Calibration" menu item in which a user is prompted, via a display screen, to determine if they want to manually calibrate the sensor of the analyte monitoring system 100 (FIG. 1). If a user wishes to proceed with the manual calibration of the sensor, instructions are output on the display 210 of the analyte monitoring device 200 as described above.

Figure 19:
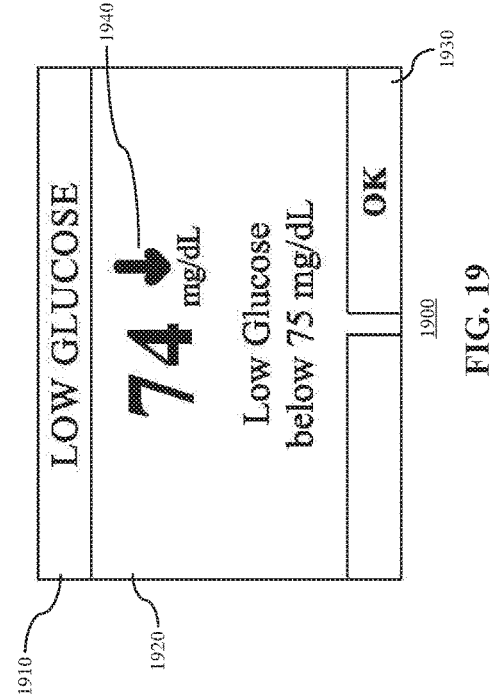
FIGS. 19-21 illustrate exemplary alert screens according to embodiments of the present disclosure.

FIG. 19 illustrates an exemplary alert screen 1900 according to embodiments of the present disclosure. As shown in FIG. 19, an alert screen 1900 may be output on the entire surface area of the display 210 (FIG. 2A) of the analyte monitoring device 200. In certain embodiments, the alert screen 1900 includes a title portion 1910 that indicates that nature of the alert (e.g., "Low Glucose"). In one aspect, the alert screen 1900 may be displayed in one or more panels of a home screen, such as, for example, panel 303 of information mode home screen 300 (FIG. 3A). If a first alert condition is detected and a second alert condition is detected prior to the first alert condition being resolved, a higher priority alert may be displayed in place of the lower priority alert. In certain embodiments, both alerts may be displayed in two separate panels of the home screen. For example, the first alert may be displayed in the first panel 303 of the information mode home screen 300, while the second alert is simultaneously displayed in the second panel 320 of the information mode home screen 300.

Figure 21:
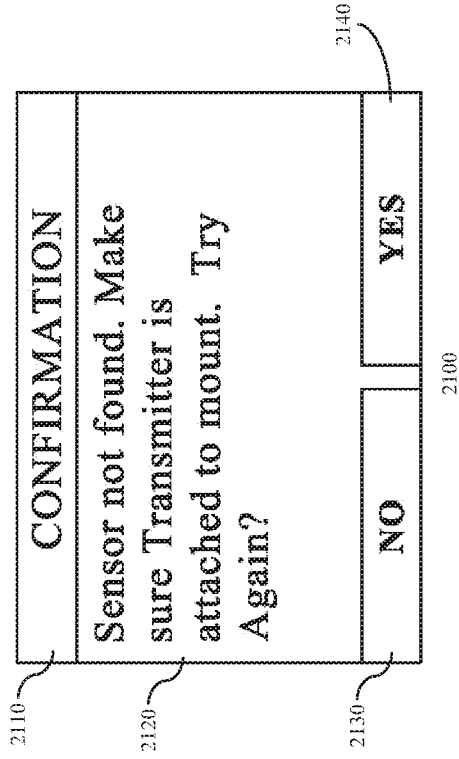
Figure 20:
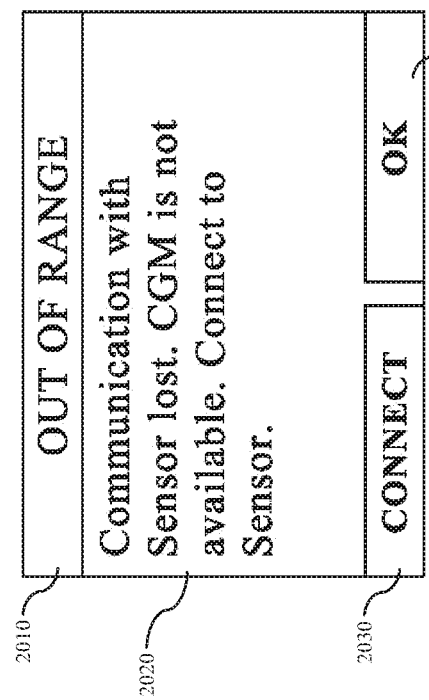

The alert screen 1900 also includes information 1920 regarding the condition that triggered the alert. For example, and as shown in FIG. 19, the displayed information 1920 indicates that the user currently has a glucose level of 74 mg/dL which is below a predetermined threshold level of 75 mg/dL. Also shown is a softkey button corresponding to the "OK" softkey label 1930. Further, the alert screen 1900 shows that the user's glucose level is rapidly decreasing as indicated by the downward arrow 1940. Additional exemplary alert screens are shown in FIGS. 20 and 21.

In certain embodiments, actuation of the secondary button 240 (FIG. 2C) or another softkey button such as, for example, input button 220, when an alert screen is displayed, causes the display 210 to output a display screen that corresponds to the detected alert condition. For example, if the alert condition corresponds to a glucose level that is below a predetermined threshold, actuation of the secondary button 240, or another softkey button, may cause the display 210 to output a graph, such as for example, graph 400 (FIG. 4A), that shows glucose data and corresponding events (e.g., exercise, meals, bolus doses etc.) that may have contributed to the alert condition. Additionally, actuation of the secondary button 240 or other softkey button when an alert screen is displayed may cause the display 210 to output an alarm setting display screen in which the user may select to silence or mute the alarm associated with the alert condition for a predetermined period of time. In certain embodiments, the display screen that is output upon actuation of the secondary button 240 when an alert screen is displayed may vary based on the type of the alert detected. For example, if the alert screen corresponds to a low urgency alert, actuation of the secondary button 240 causes a first display screen to be output on the display 210. Further, if the alert screen corresponds to high urgency alert, actuation of the secondary button 240 causes a second display screen to be output on the display 210.

Although specific alert screens are specifically described above, it is contemplated that various other alerts may be output on the display 210 of the analyte monitoring device 200. Examples of alert screens that may be output on the display 210, along with the meanings of the alert screens are as follows: "CGM is not available. Check your BG in 3 hours to calibrate."—which may indicate that the sensor signal is settling and glucose results may not be accurate, the system has stopped reporting glucose results and will ask for another calibration in 3 hours, and glucose alarms are not active; "Calibration BG out of range (60-400 mg/dL). Check your BG later to calibrate."—which may indicate that the user's blood glucose results is too low or too high; "Check your BG in 15 minutes to calibrate."—which may indicate that the calibration test was very different from the previous calibration; "Check your BG in 1 hour to calibrate."—which may indicate that calibration failed for one of several possible causes which includes 1) information from the transmitter was incomplete; 2) there was no communication between the transmitter and the analyte monitoring device; 3) the sensor may not be working properly; and 4) the user's glucose levels have been changing rapidly; "Receiver temperature out of range. Check your BG in 1 hour to calibrate."—indicating calibration failed because the analyte monitoring device was too warm or too cold; "CGM is not available. Check your BG to calibrate."—indicating that the calibration has expired and glucose alarms are not active; "Check your BG to confirm your last calibration."—indicating the sensor signal may still be settling and the system requires another calibration to confirm the sensor signal; "Charge receiver soon."—indicating that there is less than 25% of charge remaining; "Charge receiver immediately."—indicating that less than 15% of charge is remaining; "Receiver will lose all power soon. Charge Receiver immediately."—indicating that no charge is remaining and the analyte monitoring device could shut down at any time; "Receiver temperature is low. Warm up Receiver to maintain power."—indicating the analyte monitoring device temperature is too cold; "CGM not available. Connect to Sensor."—indicating that the analyte monitoring device has not been receiving signals sent by the transmitter, and the analyte monitoring device is either too far from the transmitter or there are materials or signals causing interference and glucose alarms are not active; "Transmitter Battery is low. Replace the Transmitter with the next Sensor."—indicating the transmitter battery has less than 10% charge; "Need to replace Transmitter in 2 months. Contact customer service."—indicating the transmitter battery has less than 20% charge; "CGM is not available. Ensure the Sensor is firmly attached."—indicating that there is an unstable sensor signal, glucose cannot be calculated, and glucose alarms are inactive; "CGM not available. Replace the Sensor to continue CGM."—indicating that glucose has not been calculated for the past 60 minutes and glucose alarms are not active; "CGM is not available. Sensor life is complete. Replace the Sensor to continue CGM."—indicating that alarms are not operating because the 5-day life of the sensor has ended and glucose alarms are not active; "Did you Remove the Sensor? Select 'Yes' to end CGM."—indicating that the system has detected that the sensor was just removed or that the sensor may be pulling out of the user's skin; "Sensor life nearly complete. Replace the Sensor by (date and time)"—indicating that the sensor will reach the end of its life within 2 hours; "The skin near the sensor is too [cold/warm] for calibration. [Warm up/Cool down] your skin."—indicating that the user's skin temperature may be out of range for calibration; "CGM is not available. The skin temperature near the Sensor is too cold or warm; "Correct to continue CGM."—indicating the skin is too cold or too warm to display continuous glucose readings and that glucose alarms are not active; "Check your BG to Calibrate."—indicating a blood glucose reading is needed for calibration in which case the analyte monitoring device prompts the user to perform this test approximately 1, 2, 10, 24 and 72 hours after a new sensor is inserted; and "Transmitter has detached from Sensor. CGM is not available. Replace the Sensor to continue CGM."—indicating the transmitter is not firmly attached to the sensor and glucose alarms are not active.

In certain embodiments, additional error screens showing "BG check not available", "Er 1", "Er 2", "Er 3", and "Er 4" may be output on the display 210 when a user is checking blood glucose levels. Such error screens may indicate that the analyte monitoring device 200 is charging while a user is trying to perform a blood glucose test, the blood sample on the test strip is too small, the blood glucose of the sampled blood is very low (e.g., less than 20 mg/dL) or very high (greater than 500 mg/dL), there is a problem with the test strip or analyte monitoring device 200, control solution labeled HIGH is applied when the temperature is too cold, or the blood glucose procedure was not performed correctly, such as, for example, putting blood on the test strip before inserting the test strip into the test port.

Although specific alert screens have been described above, it is contemplated that additional alert screens may be output on the display 210, with each of the alert screens falling into various classifications. These alerts include low urgency alerts, intermediate urgency alerts, medium urgency alerts, and high urgency alerts. Each classification of alert may have varying tones, alarms, display colors and alert display screens associated therewith. For example, low urgency alert display screens may be output in a first color, intermediate urgency alert display screens may be output in a second color, medium urgency alerts may be output in a third color and high urgency alerts may be output in a fourth color. Additionally, each of the alerts may include fixed text or context-dependent text. For example, a projected alarm may include the current glucose value and trend, the alarm threshold, or the time horizon of the alarm projection. In one aspect, alert messages may include icons, graphs or other indicators depending on whether the alarm relates to device malfunctions, analyte levels, or the need to calibrate the sensor.

In certain embodiments, a low urgency alert is provided when a condition occurs which is of low priority. Such low urgency alerts may correspond to malfunctions of the analyte monitoring device 200. For example, a low urgency alert may be provided when a history log is corrupted, a loss of settings of the analyte monitoring device 200, a broken strip port light, a broken speaker, a broken vibratory indicator, a need to establish a link, a transmitter battery warning or a cleared history.

In certain embodiments, a low urgency alert is output on the display 210 as a yellow message screen. To bypass the screen, the user may be required to actuate a softkey button corresponding to a softkey label displayed on the message screen. In addition to displaying the message, a low urgency alert tone and/or vibration may be output from the analyte monitoring device 200 depending on selected user settings. Low urgency alerts may be silenced after the low urgency alert is displayed or all low urgency alerts may be muted by a user.

Intermediate urgency alerts are output when a condition occurs that is more important than low urgency alerts. In certain embodiments, intermediate urgency alerts correspond to various calibration conditions such as those described above. For example, intermediate alerts may be output upon occurrence of a request for calibration, a failed calibration because a fingerstick reading is too high, too low or invalid, unsuitable pre-calibration conditions because skin temperature is too high or too low, or a failed calibration because skin temperature is too high or too low. In another embodiment, immediate urgency alerts may notify a user to remove a test strip from a test strip port or to re-sync the transmitter and analyte monitoring device 200.

Intermediate urgency alerts may be output on the display 210 of the analyte monitoring device 200 as a yellow message screen. Each alert may have accompanying alarms and vibration settings, each of which are user selectable. Intermediate urgency alerts may also be output repeatedly for a predetermined amount of time until addressed by the user or until the user puts the alert "on hold." In certain embodiments, an intermediate alert may be put "on hold" or "snoozed" for a predetermined amount of time (e.g., 5 minutes). If the intermediate alert is not addressed after the "on hold" time has elapsed, the alert, including the message screen and/or the tactile/audible alarm, is output a second time. Intermediate alerts may be silenced when the alert message is acknowledged by the user or the condition that triggered the alert ceases to exist. As discussed above, the alarm tones and snooze time of intermediate alerts may be user selectable.

In certain embodiments, a medium urgency alert is provided when a condition occurs that is a higher priority than the intermediate urgency alert. In certain embodiments, a medium urgency alert corresponds to the occurrence of a high glucose condition, a projected high glucose condition or a projected low glucose condition. In a medium urgency alert, an alarm and a yellow alert screen are output on the display 210 on the analyte monitoring device 200. As with other alarms, the alarm tone, duration and volume for the medium urgency alert may be user selectable. Based on a user's settings, the alarm may be output in 6 second increments for one minute until the alert is acknowledged. However, once the user acknowledges the alert, the alert may be put "on hold" or "snoozed" for a user selectable time period (e.g., 5 minutes) by actuating a softkey button on the analyte monitoring device 200.

In certain embodiments, medium urgency alerts may be "acknowledged" and put on hold for various periods or amounts of time based on user selection. An acknowledgement may occur when user actuates a softkey button associated with a particular softkey label on the display 210 of the analyte monitoring device 200. If the user selected "acknowledgement" time period passes and the condition that triggered the medium urgency alert still exists, a high urgency alert, including a high urgency alert display screen and/or audible/tactile notification may be output by the analyte monitoring device 200. Medium urgency alerts are deactivated when the condition that triggered the alert ceases to exist. As with other alerts described above, the alarm tones and snooze feature of the medium urgency alert are customizable by a user.

In certain embodiments, a high urgency alert is provided when low glucose condition are detected, such as, for example, the low glucose condition shown above with respect to FIG. 19. The display screen of a high urgency alert may be output on the display 210 of the analyte monitoring device 200 as a red display screen. If the user interface of the analyte monitoring device 200 is not active (e.g., in a sleep mode), a high urgency alarm is output once every six seconds for a predetermined amount of time. If the user interface of the analyte monitoring device 200 is active, the high urgency alert is output on the display 210. As with other alerts, actuation of a softkey button may put the high urgency alert on hold for a predetermined amount of time. High urgency alerts may be put on hold for user selectable periods of time if the user acknowledges the alert and actuates a softkey button corresponding to an acknowledgement softkey label. If the same high urgency alert condition still exists after the acknowledgement period expires, the high urgency alert is output a second time. In certain embodiments, high urgency alerts are silenced when the condition that triggered the high urgency alert ceases to exist. In one aspect, high urgency alerts are not mutable.

FIG. 20-21 show additional exemplary alert screens according to embodiments of the present disclosure. Referring to FIG. 20, alert screen 2000 includes a title portion 2010 indicating the nature of the alert screen (e.g., sensor out of range) and a message portion 2020 that notifies the user of the cause of the alert. Although text is specifically shown in FIG. 20, it is contemplated that the text may be replaced by an icon, a series of icons, video clip, sound byte etc.

In certain embodiments, when the alert screen 2000 has been output on the display 210 (FIG. 2A) of the analyte monitoring device 200, the user may attempt to connect the analyte monitoring device 200 to a sensor, such as, for example, sensor 101 (FIG. 1) by actuating a softkey button corresponding to the "Connect" softkey label 2030. If the user does not want to attempt to connect the analyte monitoring device 200 to a sensor, the user may acknowledge the alert screen by actuating a softkey button corresponding to the "OK" softkey label 2040. Once the alert screen 2000, has been acknowledged, the user is returned to a home screen, such as, for example, home screen 300 (FIG. 3A).

Referring to FIG. 21, alert screen 2100 includes a title portion 2110 indicating the nature of the alert screen (e.g., confirmation of a user action) and a message portion 2120 that notifies the user of the cause of the alert. Although text is specifically shown in FIG. 21, it is contemplated that the text may be replaced by an icon, a series of icons, video clip, sound byte etc.

In certain embodiments, when the alert screen 2100 has been output on the display 210 (FIG. 2A) of the analyte monitoring device 200, the user may attempt to establish a connection between the analyte monitoring device 200 and a transmitter such as, for example, transmitter unit 102 (FIG. 1). The user may attempt to establish a connection between the analyte monitoring device 200 and the transmitter by actuating a softkey button corresponding to the "Yes" softkey label 2140. If the user does not want to attempt to establish a connection between the analyte monitoring device 200 and the transmitter, the user may acknowledge the alert screen by actuating a softkey button corresponding to the "No" softkey label 2130. Once the alert screen 2100, has been acknowledged, the user is returned to a home screen, such as, for example, home screen 300 (FIG. 3A).

Figure 22:
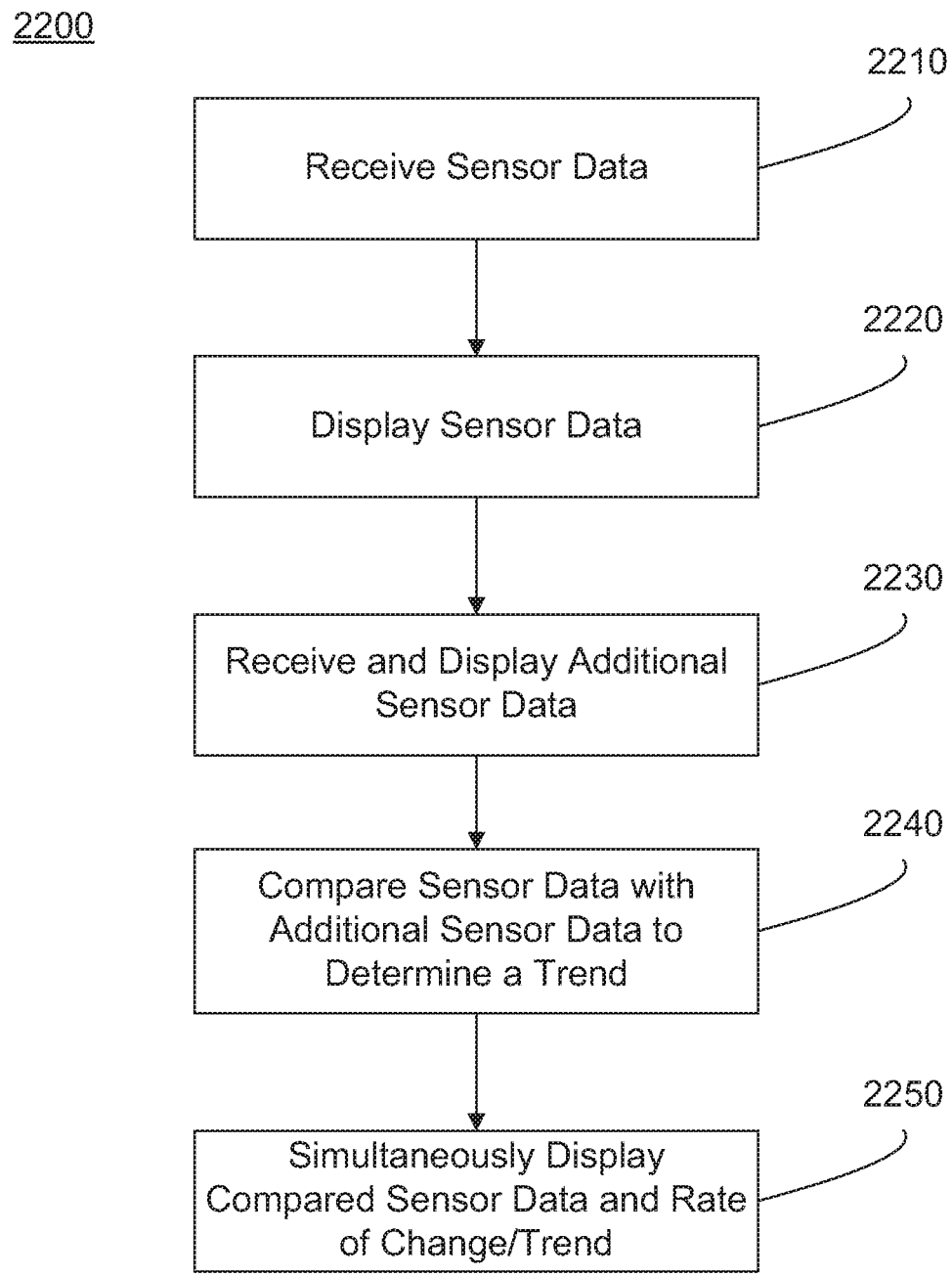
FIG. 22 is a flow chart illustrating a method for displaying sensor data according to embodiments of the present disclosure.

FIG. 22 illustrates a method 2200 for displaying sensor data according to embodiments of the present disclosure. The routine for displaying sensor data begins when sensor data is communicated by a transmitter (2210), such as transmitter unit 102 (FIG. 1), and received by a receiving unit, such as receiving unit 104 (FIG. 1) or analyte monitoring device 200 (FIG. 2A). In certain embodiments, the sensor data corresponds to an analyte level of a user, such as, for example, a current glucose level. In certain embodiments, the data is transmitted and received "on-demand" by placing the analyte monitoring device 200 in close proximity with the transmitter unit 102 and initiating data transfer, either over a wired connection, or wirelessly by various means, including, for example, various RF-carried encodings and protocols and IR links.

When the sensor data is received, a processor of the analyte monitoring device 200 outputs the data on a display screen of the analyte monitoring device 200 (2220). In certain embodiments, the received sensor data may be displayed on an information mode home screen such as described above with reference to FIG. 3A. In such embodiments, the sensor data is plotted as a point on a graph that is output on a first section of the information mode home screen. The received sensor data may also be simultaneously displayed in a second section of the information mode home screen as a numerical value of a current analyte level. In one aspect, the sensor data may be stored in a memory of the transmitter unit 102 or in a memory of the analyte monitoring device 200 after it has been received and not displayed until additional sensor data is received.

As additional sensor data is obtained by the sensor (2230), the additional sensor data may be transmitted by the transmitter unit 102 and received by the analyte monitoring device 200 on-demand or at regular time intervals. When the additional sensor data is received, a processor outputs a numerical representation of the additional sensor data on the display in the second section of the information mode home screen as the current analyte level. Additionally, when the additional sensor data is received, the additional sensor data is plotted on the graph corresponding to an analyte level on a y-axis at a time t on the x-axis that the data was received.

As additional sensor data is received by the analyte monitoring device 200, the processor compares the previously received sensor data to the additional sensor data (2240) to determine a rate of change and the trend data between the two readings. In certain embodiments, this data may be used to calculate and display the rate of change of the analyte levels of the user. Once the rate of change and/or trend data is determined, the rate of change is displayed on the graph portion of the information mode home screen (2250) with the current analyte level and trend information being simultaneously displayed on a second portion of the home screen such as, for example, home screen 300 (FIG. 3A).

Figure 23:
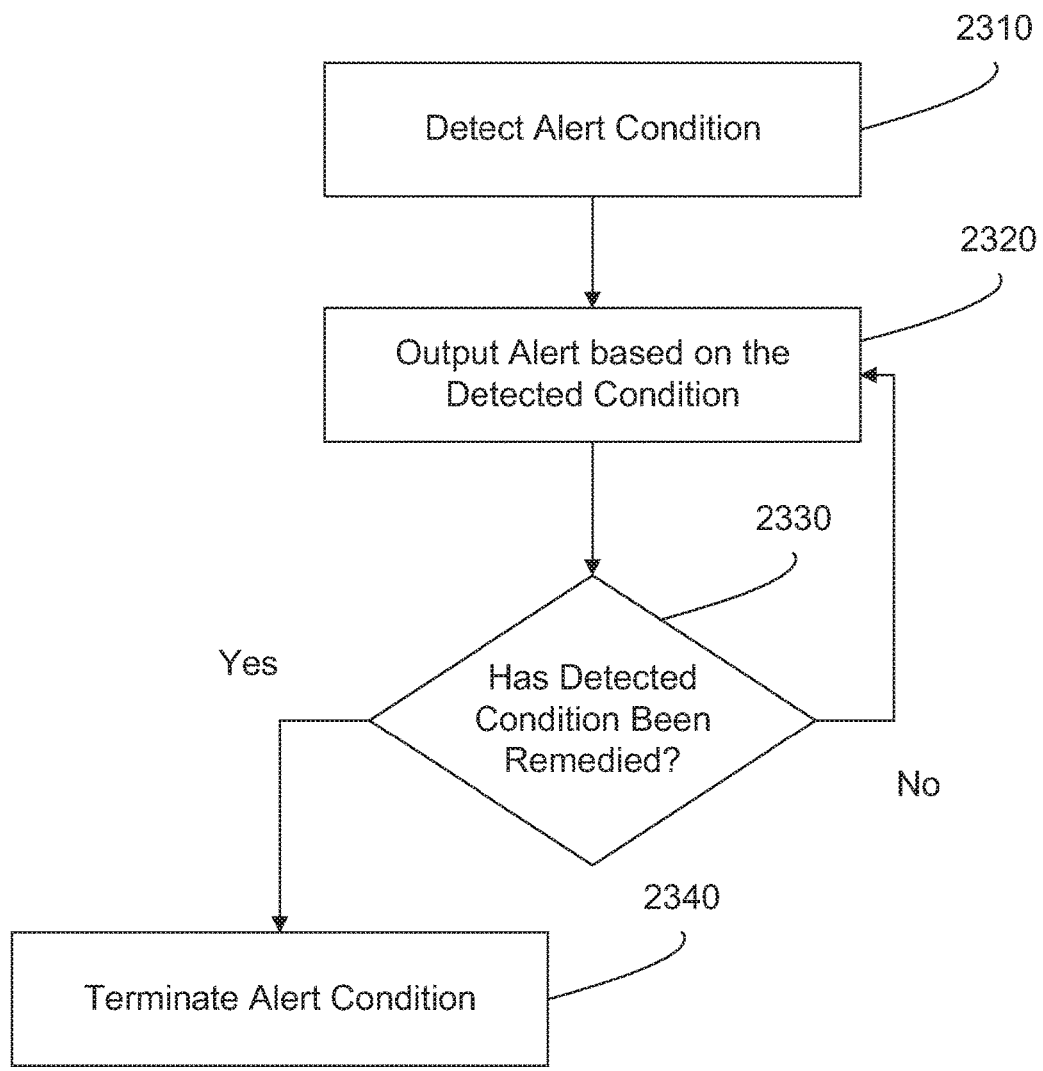
FIG. 23 illustrates a flow chart for outputting an alert based on a detected alert condition according to embodiments of the present disclosure.

FIG. 23 illustrates a method 2300 for outputting an alert based on a detected alert condition according to embodiments of the present disclosure. The routine for outputting an alert based on a detected alert condition begins when an alert condition is detected (2310) by a processor of the analyte monitoring device 200 (FIG. 2). In certain embodiments, the detected alert condition may correspond to low urgency alerts, intermediate urgency alerts, medium urgency alerts, and high urgency alerts as discussed above. In certain embodiments, each of the alert levels may be arranged based on the urgency level and/or priority. Thus, if a low urgency alert is detected simultaneously with or substantially simultaneously with an intermediate urgency alert, the intermediate urgency alert is output by the analyte monitoring device 200.

When an alert condition is detected, an alert screen, corresponding to the detected alert condition, is output on the display of the analyte monitoring device 200 (2320). In certain embodiments, the alert screen may correspond to the alert screen 1900 described above with respect to FIG. 19. Accordingly, each alert screen may be output on the entire surface area of a display 210 of the analyte monitoring device 200. The alert screen may include a title portion that indicates that nature of the alert and also includes information regarding what triggered the alert (e.g. high glucose level, sensor calibration etc.). In addition to displaying alert screens, alarms and/or vibrations may be output to further inform the user of a detected alarm condition.

When an alert condition is detected, a processor of the analyte monitoring device 200 determines whether the detected condition has been remedied (2330). In certain embodiments, the processor of the analyte monitoring device 200 issues a command to determine what triggered the alert condition and, based on received data corresponding to the alert condition, whether the condition is ongoing. For example, if the alert condition corresponds to a low battery alert of a battery of the analyte monitoring device 200, the processor may determine that the condition no longer exists because the analyte monitoring device 200 is being charged. If it is determined that the condition has been remedied, the processor issues a command to terminate the alert (2340).

In certain embodiments, depending on the type of alert, various conditions may need to be met prior to the alert being terminated. For example, if the alert is a high urgency alert, such as a low glucose level, a detected current glucose level may need to be at or above a minimum glucose threshold level for a predetermined amount of time. If, for example, the alert is a medium urgency alert, such as a projected high glucose condition or a projected low glucose condition, the user may need to take actions, such as, for example, administering a bolus insulin dose to change the trend data associated with the alert.

In certain embodiments, if an alert screen has been displayed for a detected alert condition but no action has been taken within a predetermined amount of time (e.g. 1 hour), the processor may issue a command to output subsequent notifications such as a follow-up alarm or vibration. In one aspect, subsequent notifications may be output only for certain types of alert conditions, such as, for example high urgency alerts. In another embodiment, subsequent notifications (e.g., tactile, audible, and/or visual) may be output for all types of alert conditions (e.g., low urgency alerts, medium urgency alerts etc.). As stated above, a user may have an option of muting alarms for some of the different types of alerts described above (e.g., low urgency alert). In cases where the alarm has been muted, but no action has been taken regarding the alert notification for a predetermined period of time, the processor may issue a command to override the mute setting and the alarm and/or alert notification is output.

As discussed above, each of the low urgency alerts, intermediate urgency alerts, medium urgency alerts, and high urgency alerts may allow a user to put the alert on hold for a predetermined amount of time. When the predetermined amount of time expires, the processor issues a command to determine if the detected alert condition still exists. If it is determined that the condition still exists, the above process is repeated until the detected alert condition is remedied.

In cases where the alert is a medium urgency alert, the "on hold" time passes and the condition still exists, the medium urgency alert may be upgraded to a high urgency alert. Thus, the alert notification is output with a corresponding high urgency display screen and alarm tone. Although upgrading a medium urgency alert has been specifically discussed, it is contemplated that various other alert conditions may be upgraded from one level to another, such as, for example, a low urgency alert being upgraded to an intermediate urgency alert.

Figure 24A:
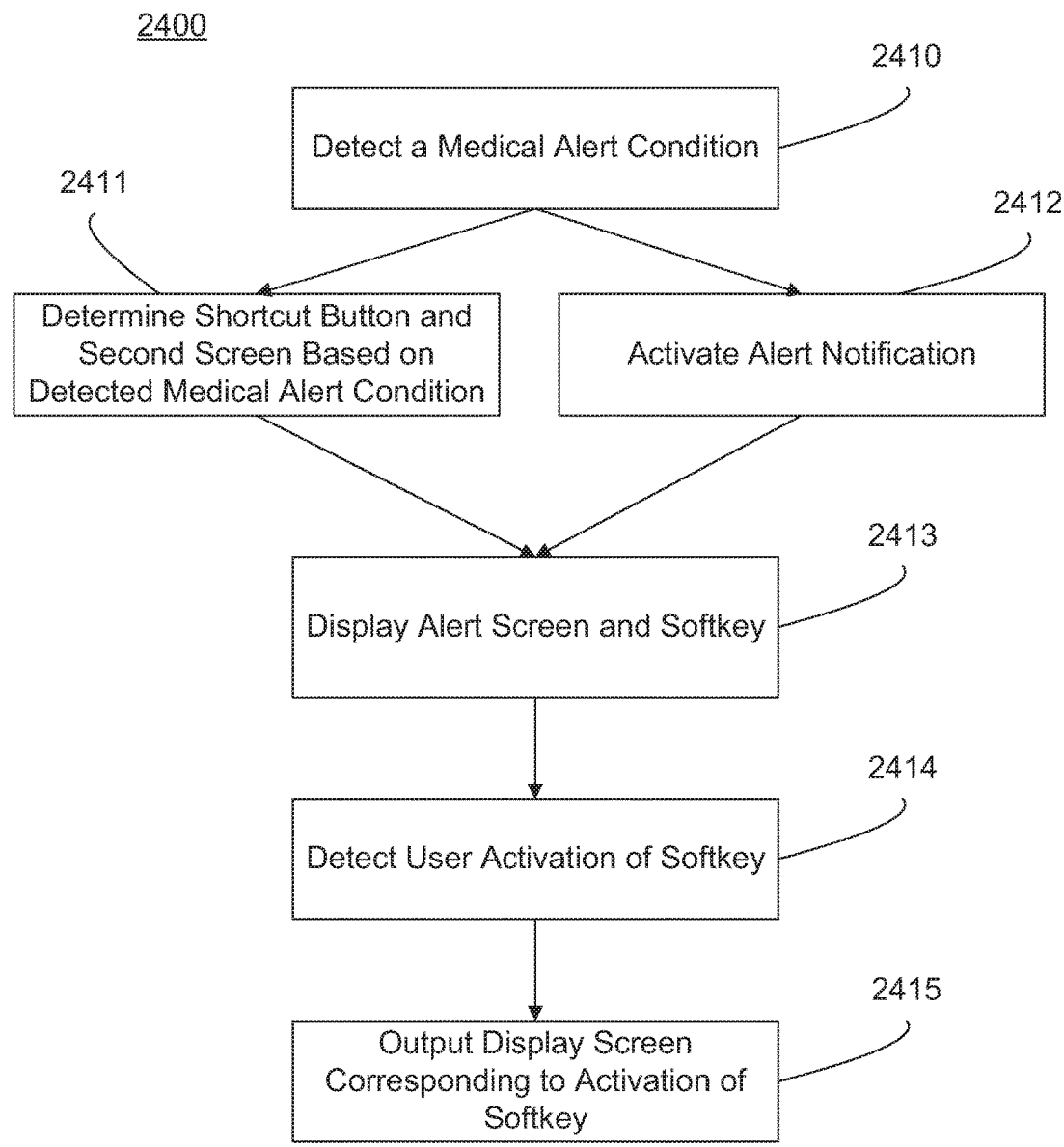
FIG. 24A illustrates a flow chart for outputting display screens based on a detected alert condition according to embodiments of the present disclosure.

FIG. 24A illustrates a flow chart 2400 for outputting display screens based on a detected alert condition according to embodiments of the present disclosure. As shown in FIG. 24A, a processor of an analyte monitoring device, such as analyte monitoring device 200 (FIG. 2A) first detects a medical alert condition (2410). The detected medical alert condition may correspond to a high urgency alert such as described above. The processor of the analyte monitoring device 200 may activate an alert notification, such as, for example, output an alarm tone and an alert display screen, and simultaneously determine a softkey button label for a softkey button that will output a display screen corresponding to alert condition upon user actuation of the softkey button (2411 and 2412). When the user actives the analyte monitoring device 200, the alert screen associated with the alert condition is output on the display 210 of the analyte monitoring device 200 (2413). When the user actuates the softkey button associated with the softkey button label (2414) a second screen is output on the display 210 of the analyte monitoring device 200 (2415). In certain embodiments, the second screen is a home screen such as, for example home screen 300 (FIG. 3). In an embodiment, the second screen corresponds to the detected alert condition. For example, if the detected alert condition is a low battery, actuation of the softkey button with the corresponding softkey button label may take the user directly to a status display screen, such as was described above with reference to FIG. 18.

In other examples, if the analyte monitoring device 200 detects a high glucose level and outputs an alarm, such as, for example, an alarm as shown in shown in FIG. 24B, the message may include a "Bolus" softkey label 2420 and an "Accept" softkey label 2422. If the user selects the a softkey button associated with the "Accept" softkey label 2422, the display 210 of the analyte monitoring device 200 returns to a home screen, such as home screen 300 (FIG. 3A). However, if the user selects a softkey button associated with the "Bolus" softkey label 2420, a bolus calculator screen may be output on the display 210 of the analyte monitoring device 200 (as depicted in FIG. 24C). The bolus calculator screen may display insulin information such as, for example, insulin on board information, the correction bolus that was or is going to be applied by an insulin pump and the total insulin bolus amount. In certain embodiments, the bolus calculator screen may include an entry field to allow a user to manually input bolus amounts. Additionally, the bolus calculator screen may include a softkey label 2424 (labeled as "Next") which directs the user to another display screen comprising additional information corresponding to a bolus calculator. For example, actuation of a softkey button corresponding to the "Next" softkey label 2424 could cause a help display screen corresponding to the bolus calculator to be output on the display 210.

In certain embodiments, the shortcut mechanism can also be used to take the user to a display screen in which the user can modify the settings of the alarm that is being output. For example, when an alarm is output, the user may want to mute further alarms, activate a snooze mode, turn down the volume, or place the analyte monitoring device 200 in vibrate only mode. In certain embodiments, a plurality of shortcut mechanisms may be programmed into the device based on, for example, a length of a button press, a combination of buttons pressed etc.

As described above, some alert conditions are characterized by an analyte level exceeding a threshold. In this manner, the detected alert condition relates to a physiological condition of a user such as hypoglycemia, hyperglycemia, impending hypoglycemia, or impending hyperglycemia. In certain embodiments, outputting an alarm means producing one or more notification signals associated with the alert condition such as a visual message, an auditory message, a vibration, or other sensory-stimulating signals such as heat, cool, electrical shock etc. Notifications such as these can alert or warn a user of the occurrence of a condition that either relates to the health of the user or to the functionality of the analyte monitoring device 200.

As discussed above, an alarm may be output when the signal from the sensor indicates the glucose level has exceeded or is about to exceed a threshold value. Some non-limiting examples of threshold values for blood glucose levels are about 60 mg/dL, 70 mg/dL, or 80 mg/dL for hypoglycemia, about 70 mg/dL, 80 mg/dL or 90 mg/dL for impending hypoglycemia, about 130 mg/dL, 150 mg/dL, 175 mg/dL, 200 mg/dL, 225 mg/dL, 250 mg/dL, or 275 mg/dL for impending hyperglycemia and about 150 mg/dL, 175 mg/dL, 200 mg/dL, 225 mg/dL, 250 mg/dL, 275 mg/dL or 300 mg/dL for hyperglycemia. Further, each of the conditions mentioned above can have different notification signals, such as different audible tones or alarms, different alert screen colors, different screen brightness, different icons and the like. It is also contemplated that an alert condition may be detected if sensor readings indicate a value is beyond a measurement range of the sensor.

In yet another embodiment, an alert condition may be detected when the rate of change or acceleration of the rate of change in an analyte level exceeds a threshold rate of change or acceleration. For example, the analyte monitoring device 200 may be configured to output a dynamic glucose level alarm if the detected rate of change in glucose concentration exceeds a threshold rate of change for a predetermined amount of time (e.g., the rate of change of glucose level detected over a specified period of time was in excess of 3-4 mg/dL/min). A rate of change such as described may indicate that a hyperglycemic or hypoglycemic condition is likely to occur. Although specific rates of change have been mentioned, it is contemplated that the rate of change threshold and the time period associated with the rate of change may be selected and adjusted by the user or a health care provider.

In certain embodiments, the alarm tone for the dynamic glucose level alarm may be a unique alarm such that the user is more readily warned of the possible pending condition. As such, in one embodiment, this particular alarm may be preset and the user may not have the option to select a new alarm tone. In another embodiment, the alarm tone may be user selectable but only from a tone library that is separate and unique and a tone library that may be used by other alarms of the analyte monitoring device 200. Additionally, the display of the analyte monitoring device 200 may display a rate of change arrow that successively flashes on and off to give the user a visual indication that the user's glucose levels have been rising or falling at a rate greater than the threshold rate of change for over the predetermined time period.

The dynamic glucose level alarm is provided to assist a user who may have underestimated the carbohydrates of a meal. Additionally, the dynamic glucose level alarm can also serve as an emergency warning when errors are made in restaurants or in the home and users are mistakenly given high-carbohydrate food or drinks when they were expecting and had prepared for low or zero-carbohydrate food. In circumstances where a user also uses an insulin pump, the dynamic glucose level alarm may also be used to detect pump failure as the dynamic glucose level alarm is based on the actual rate of change of the user's glucose. Thus, the alarm can provide users with an early warning of a potential hyperglycemic state.

In certain embodiments, alert conditions, such as those described above, may be triggered if a predetermined number of data points spanning a predetermined amount of time meet or exceed a threshold value. In another embodiment, an alarm may be output only when the data points spanning a predetermined amount of time have an average value which meets or exceeds the threshold value. Each condition that triggers an alert may have different alert activation criteria. Additionally, the alert activation criteria may change depending on current conditions.

In certain embodiments, an alert condition can relate to the status of one or more hardware components of the analyte monitoring device 200. For example, when a battery of the analyte monitoring device 200 drops below a predetermined threshold voltage level or when a battery is reaching its expected life, an alert condition may be output. Additionally, an alert condition may relate to the status of signal transmission, data processing and other processes of the device. For example, for signal transmission between the transmitter unit 102 (FIG. 1) and the primary receiver unit 104 (FIG. 1), an alert condition may be detected by a processor of the receiver unit 104 if the receiver unit 104 does not receive a predetermined number of data packets in succession or within a predetermined amount of time. In one aspect, the wireless connection icon 330 may show a disconnected status if the receiver unit 104 does not receive a predetermined number of data packets in succession or if packets are not received for a predetermined amount of time (e.g. 2 minutes).

FIGS. 25A-25G describe various embodiments relating to the suppression of alarms based on alert conditions according to embodiments of the present disclosure. As described above, a receiver, such as analyte monitoring device 200 (FIG. 2) is configured to enable a suppression of outputting an additional alarm associated with a detected alert condition for a predetermined period of time after the alarm associated with the alert condition has been output.

Figure 25E:
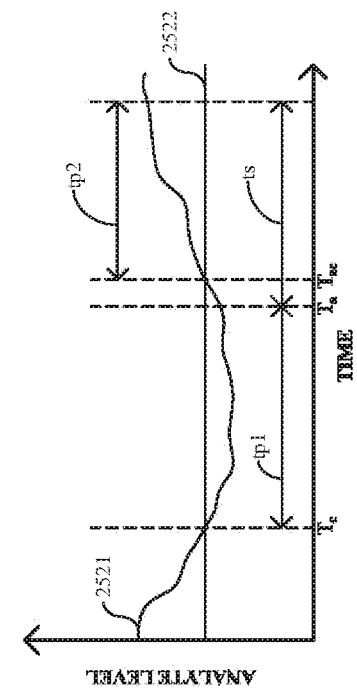
FIGS. 25A-25G describe various embodiments relating to the suppression of alarms based on alert conditions according to embodiments of the present disclosure.
Figure 25A:
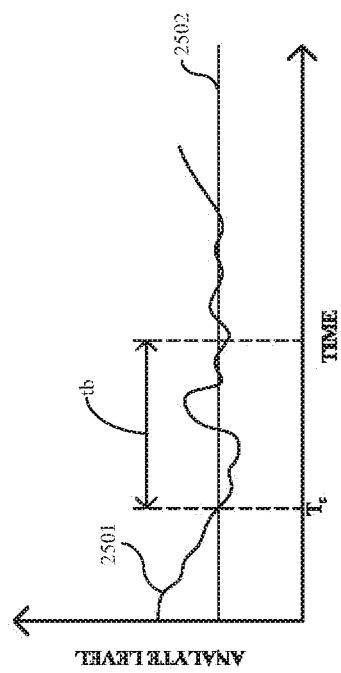

Referring to FIG. 25A, a time dependent curve 2501 represents an analyte level being monitored with a predetermined analyte level threshold for hypoglycemia being represented by the line 2502. When the analyte level curve 2501 moves from above the threshold 2502 to below the threshold (designated by point Tc) an alert condition is detected regarding the event. In certain embodiments, the alert can be terminated within a predetermined amount of time (e.g., 60 seconds) or after the user deactivates the alarm. However, as the curve 2501 fluctuates along the threshold level for an extended period of time due to either noise or true signal variation, the alert condition may be detected multiple times. As a result, an alarm associated with the alert condition may be output multiple times.

To alleviate this problem, outputting of the alarm is suppressed for a predetermined period of time (indicated by line tb). The predetermined period of time starts when the occurrence of the alert condition is first detected (at point Tc). In certain embodiments, the predetermined period of time represented by tb can be selected by a user to be 15 minutes, 30 minutes or some other timeframe. Once the selected block period of time expires, data corresponding to the current analyte level of the user is received and evaluated by a processor of the analyte monitoring device 200 to determine whether a further alarm needs to be output. If it is determined that another alarm needs to be output (e.g. the alert condition still exists), the alarm is output. After the alarm is output, an additional time period can be defined and the process repeats.

Figure 25C:
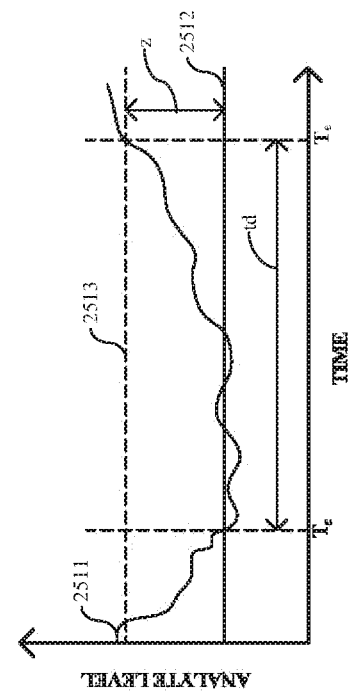
Figure 25B:
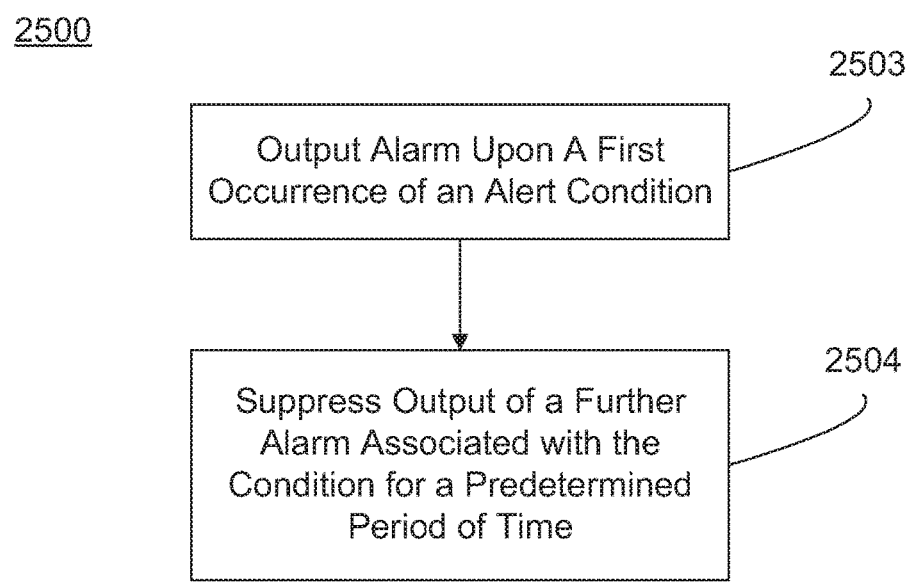

In accordance with this embodiment, a method 2500 for managing an alarm is provided as shown in FIG. 25B in which an alarm is output upon an occurrence of an alert condition (2503). Once the alarm has been output and subsequently silenced by a user (e.g. by the user actuating a softkey button to mute the alarm or enter a snooze mode), outputting additional alarms associated with the condition are suppressed for a predetermined amount of time (2504). As will be appreciated by those of ordinary skill in the art, the predetermined period of time can be similarly applied for alarms associated with other alarm conditions such as, for example, low battery level, data transmission errors and the like.

FIG. 25C illustrates an embodiment in which the analyte monitoring device 200 (FIG. 2A) may be configured to set or obtain a second analyte level threshold within (e.g., above or below) the first threshold by a predetermined value. As shown in FIG. 25C, a time dependent curve 2511 represents the analyte level being monitored with a predetermined analyte level threshold 2512. When the analyte level curve 2511 moves from above the threshold 2512 to below the threshold 2512 at point Tc, the alert condition (e.g., hypoglycemia) is detected. To reduce the frequency at which the alarm is output, another predetermined threshold 2513 can be established within the threshold 2512 by a predetermined quantity represented by z. In certain embodiments, the quantity z can be selected based on the condition being monitored and/or based on user preference. For example, for a hypoglycemia alarm, the quantity z can be selected as 10 mg/dL. Thus, if the hypoglycemia alarm is set at 60 mg/dL, the second threshold level is 70 mg/dL. The analyte monitoring device 200 may be configured to suppress outputting of further alert notifications until the analyte level passes within the second threshold 2513 (as indicated by point Te). In this manner, the time period td during which the alert condition is suppressed depends on the distance z between the two thresholds 2512 and 2513 as well as the progression of the monitored analyte level over the time period.

Figure 25D:
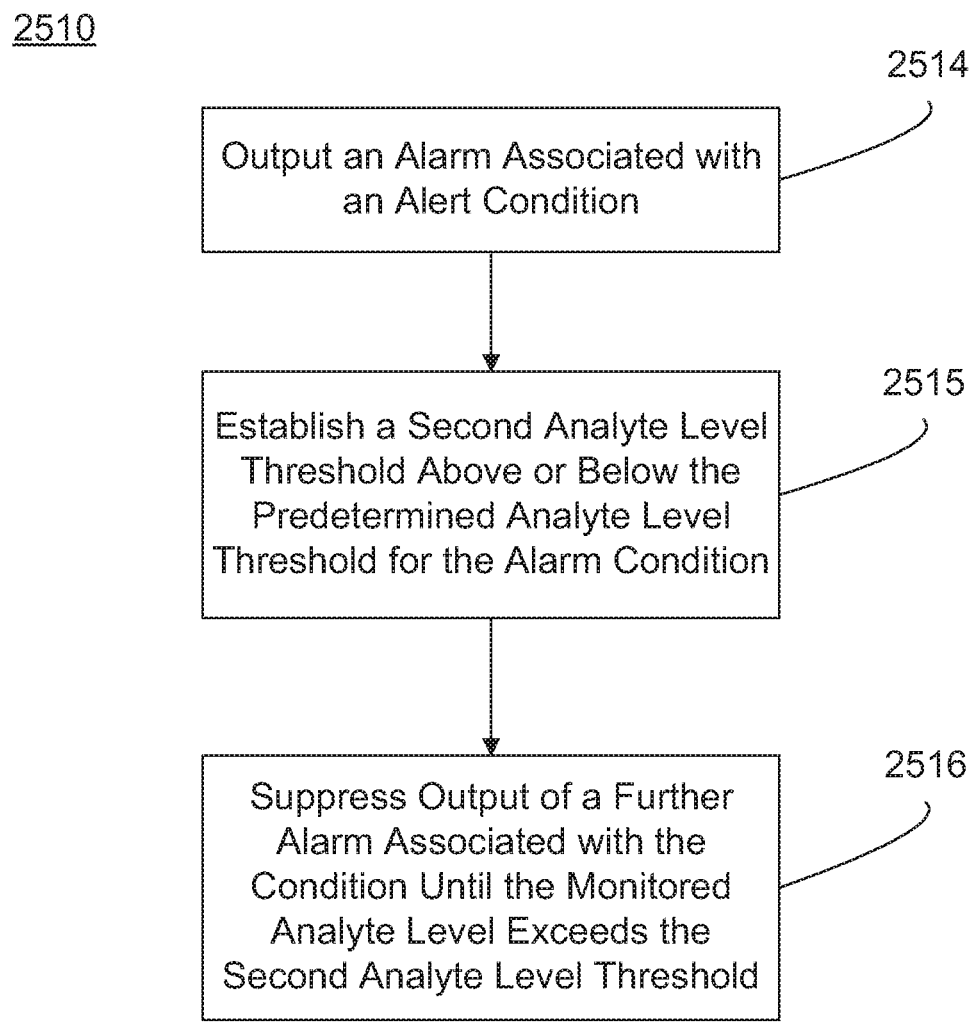

FIG. 25D illustrates a method 2510 for managing an alarm as was described above with respect to FIG. 25C. The method 2510 includes outputting an alert based on an occurrence of an alert condition (2514). After outputting the alert, a second analyte level threshold is established within the predetermined analyte level threshold (2515). Thereafter, alarms associated with the condition are suppressed until the analyte level exceeds the second threshold level (2516). In certain embodiments, the second analyte level threshold can be established before an alert condition is detected. The second analyte level threshold can be established by a user or healthcare professional preprogramming the various threshold levels into the analyte monitoring device 200.

FIG. 25E illustrates suppression of outputting an alarm associated with an alert condition for a predetermined amount of time. As shown in FIG. 25E, time dependent curve 2521 represents an analyte level being monitored with respect to the predetermined analyte level threshold 2522. When the analyte level curve 2521 moves from above the threshold 2522 to below the threshold 2522, the alert condition is detected (represented as point Tc) and an alarm is output. The analyte monitoring device 200 may be configured to suppress outputting the alarm upon the first occurrence of the alert condition and additionally apply a predetermined wait period indicated by the line tp1. A processor of the analyte monitoring device 200 suppresses outputting of the alarm corresponding to the alert condition for the entire block period represented by the line tp1. In certain embodiments, the wait period may be selected by a user or healthcare professional. Upon expiration of the time period, represented by point Ta, the alarm is output if the detected alert condition still exists.

Figure 25F:
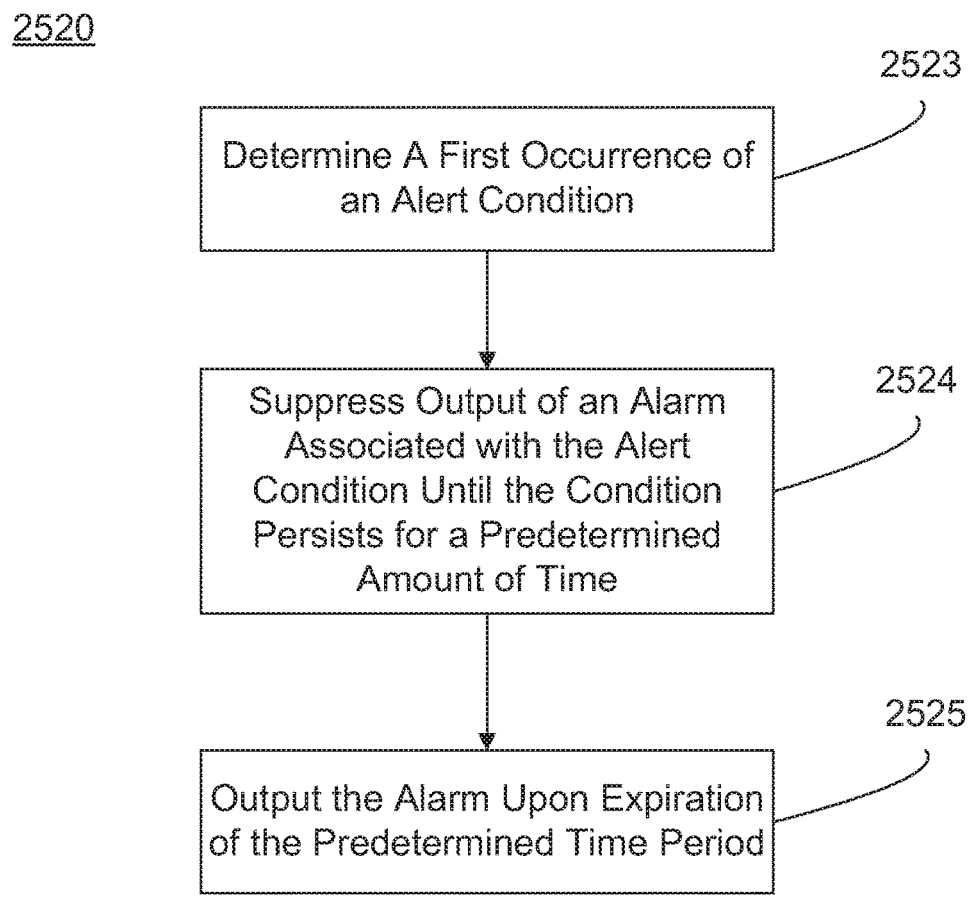

FIG. 25F illustrates a method 2520 for suppressing an alarm associated with an alert condition for a predetermined amount of time according to embodiments of the present disclosure. The method 2520 begins when an alert condition is detected and an associated alarm is output by the analyte monitoring device 200 (2523). Once the alarm has been output by the analyte monitoring device 200, the processor of the analyte monitoring device 200 suppresses further alarms until the alert condition persists for a predetermined amount of time (2524). When the alert condition has persisted for the predetermined amount of time, the processor determines whether the condition still exists. If it is determined that the condition still exits, the alarm is output (2525).

It is also contemplated that the analyte monitoring device 200 may be configured to enable suppression of an alarm associated with the detected alert condition until an absence of the alert condition persists for a predetermined amount of time. Referring back to FIG. 25E and as shown on the graph, after an alert condition is detected and an alarm is output (represented by point Ta), the analyte level moves upward and exceeds the threshold 2522 at point Tac. After exceeding the threshold 2522, the analyte level stays above the threshold 2522 and does not return back below the threshold level. In such cases, the analyte monitoring device 200 may be configured to enable suppression of outputting a further alarm until an absence of the condition (which starts from point Tac) persists for a predetermined period of time (represented by the line tp2). Thus, the alarm will only be suppressed after the condition that initially triggered the alarm has not been detected for the entire predetermined amount of time represented by the line ts. In certain embodiments, the time period represented by the line tp2 can be selected based on user input, such as, for example, 3 minutes, 5 minutes 10 minutes, etc.

Figure 25G:
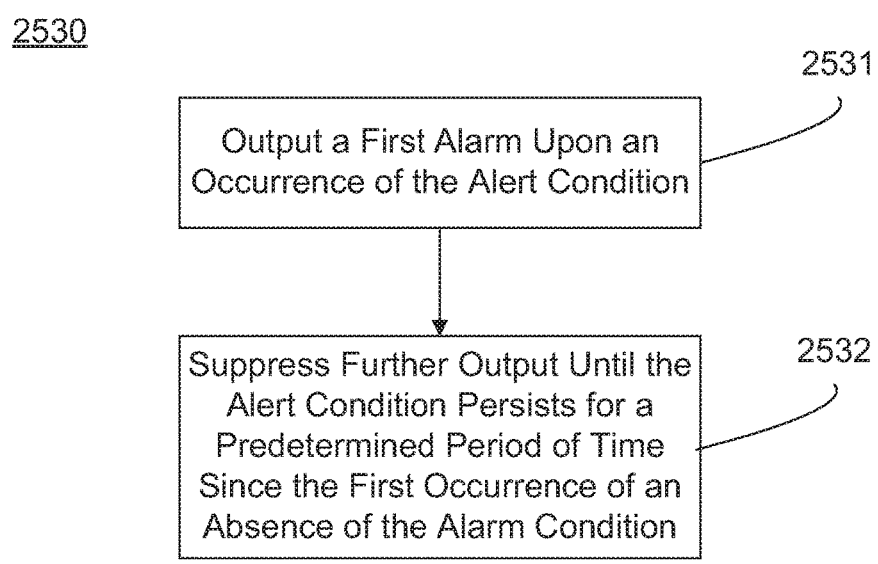

FIG. 25G illustrates a method 2530 for suppressing outputting of an alarm associated with a condition until an absence of the condition persists for a predetermined amount of time according to embodiments of the present disclosure. Method 2530 begins when an alarm is output in response to the detection of an alert condition (2531). In certain embodiments, the processor issues a command to suppress further outputting of an alarm corresponding to the detected alert condition until an absence of the alert condition persists for a predetermined period of time since the first occurrence of an absence of the alert condition (2532). If the alert condition is not detected in that predetermined time period, the alarm will not be output by the analyte monitoring device 200.

Additionally, although specific examples were used above with respect to hypoglycemia, it is contemplated that the alarm suppression techniques may be used with all detected alert conditions, such as, for example, hyperglycemia, impending hypoglycemia and impending hyperglycemia as well as alarms relating to one or more parameters corresponding to the operation of the analyte monitoring device 200.

FIG. 26 illustrates an exemplary flow of a plurality of user interface screens corresponding to establishing a connection between a sensor, such as for example, sensor 101 (FIG. 1) and a receiver unit, such as, for example receiver unit 104 (FIG. 1) according to embodiments of the present disclosure. In certain embodiments, the user may select "Connect to Sensor" from the sensor submenu 700 (FIG. 7), and begin the process of establishing a data link to the sensor and transmitter (5310). The user interface provides a find sensor screen which includes the instructions "Hold Companion Next to Sensor. Looking for sensor . . . ." The receiver then waits for a response packet from the transmitter (5320), such as, for example, transmitter unit 102 (FIG. 1). If a response packet is not received, a "Transmitter Not Found" screen and failure tone (5330) are output from the receiver. In certain embodiments, the "Transmitter Not Found" screen is a yellow message screen that asks the user to make sure the transmitter is attached to a sensor mount, and asks the user if the user wants to try again to locate the transmitter.

If a response packet is received at the receiver, and an unsupported transmitter is detected (5360), an "Unsupported Transmitter" screen is output on the display of the receiver and the receiver outputs a failure tone (5370). If a response packet is received at the receiver and an unknown transmitter is detected (5380) and the sensor life is active (5390), an "Unknown Transmitter" display screen is output on the display of the receiver and the receiver outputs a failure tone (5400). In certain embodiments, the "Unknown Transmitter" display screen is a yellow message screen and notifies the user that the detected transmitter is not the user's transmitter. The user may also be prompted via a display screen as to whether they would like to use the detected sensor and transmitter.

If an unknown transmitter is detected and the sensor life is inactive (5390), a "New Transmitter Found" display screen is output on the display of the receiver and the receiver outputs a success tone (5410). The display screen of the receiver outputs the following statement: "New Transmitter Found: Is this yours?" The display screen also displays a transmitter identification number that may be used to determine whether the identified transmitter matches the identification number of the transmitter the user is actually using. The transmitter identification number may be represented as letters only, numbers only, or alphanumeric text.

If a known transmitter is detected (5380) and a sensor count number has incremented (5420), a "Sensor Code" editable screen is output on the display of the receiver, and a success tone is output (5340). At the "Sensor Code" display screen, the user is prompted to "Enter sensor code to start sensor." An editable field "Sensor Code=" is provided on the display of the receiver to enable the user to enter the sensor code. If the sensor life is inactive (5500), a "Sensor Not Started" screen (5520) is output on the display of the receiver and the user is asked whether the user wishes to try to connect to the sensor again.

If the sensor life is active (5500), a new transmitter was not detected (5510), the sensor counter has incremented, and the user chooses "Cancel" at the "Sensor Code" screen, a "Suggest Replace Sensor Due to Expiration" message is output on the display of the receiver (5470). In certain embodiments, the user interface displays a "Sensor Expired" message because the receiver is uncertain about what sensor life the receiver is tracking. If the sensor life is active (5500) and a new transmitter was detected (5510) but the user chooses to Cancel at the "Sensor Code" screen, the sensor menu is output on the display of the receiver (5300).

If a known transmitter is detected (5380) and the Sensor Count number has not incremented (5420), the "Home" screen is output on the display of the receiver and the receiver outputs a success tone (5350). If a known transmitter is detected (5380), and the sensor life is inactive, and the Sensor Count number has not incremented (5420), a yellow alert screen is output on the display of the receiver with message reading "Suggest Replace Sensor Due to Expiration" and the receiver outputs an intermediate level alert (5470). If a known transmitter is detected (5380) and the RF radio is off (5480), a "Radio Off" display screen is output on the display of the receiver (5490).

In addition to the "Connect to Sensor" menu screen item, the user may select a "Calibration BG", which provides a "Calibration BG" message screen type, The message screen asks the user "Do you want to calibrate?" and offers the user the option to respond. A message screen displaying the time period in which the next calibration is needed along with a grace period may be output on the display of the receiver.

In certain embodiments described herein, an analyte monitoring device includes a user interface with a display and a plurality of actuators. The display is configured to output a plurality of display screens, including a home screen divided into a plurality of simultaneously displayed panels. The plurality of displayed panels may include displays of various indicators including rate of change of analyte levels, current analyte levels, analyte trend indicators, and status information, such as battery life and calibration status. The plurality of actuators, in certain embodiments, may be utilized to adjust and change the various available displays of the analyte monitoring device.

In one aspect, an analyte monitoring device may include a user interface having a display and a plurality of actuators, wherein the display is configured to render a plurality of display screens, including at least a home screen and an alert screen, wherein the home screen is divided into a plurality of simultaneously displayed panels, wherein a first panel of the plurality of panels is configured to display a rate of change of continuously monitored analyte levels in interstitial fluid, wherein a second panel of the plurality of panels is configured to simultaneously display a current analyte level and an analyte trend indicator, and wherein a third panel of the plurality of panels is configured to display status information of a plurality of components of the analyte monitoring device, and when an alarm condition is detected, the display is configured to render the alert screen in place of the home screen, the alert screen having information corresponding to the detected alarm condition, and wherein at least one of the plurality of actuators is configured to affect a further output of the analyte monitoring device corresponding to the detected condition.

In one embodiment, the first panel may include a timeline graph having a plurality of indicators disposed thereon, wherein each of the plurality of indicators represent an event.

In a further embodiment, an event may be selected from a group of events consisting of a discrete blood glucose measurement, an insulin dose, an exercise period, a meal, a state of health, and a custom event.

In another embodiment, information displayed in at least one the plurality of panels may be color coded based on a severity of a condition the information represents.

In one embodiment, at least one of the actuators may be programmable by a user.

In another embodiment, the display may be rendered in an orientation based on a type of alert screen displayed.

In another embodiment, at least one of the plurality of panels may be expandable when at least one of the plurality of actuators is actuated.

Another aspect of the present disclosure may include receiving continuous analyte level information data from a transmitter, the transmitter having a sensor in fluid contact with interstitial fluid, displaying a graphical representation of a rate of change of the continuous analyte level data over a predetermined amount of time in a first panel of a display screen of the display device, simultaneously displaying a numerical representation of a current analyte level and an iconic trend indicator in a second panel of the display screen of the display device, wherein the current analyte level is compared with a plurality of subsequent analyte levels, and wherein the current analyte level and the trend indicator are updated only when a difference between the plurality of subsequent analyte levels and the current analyte level exceeds a predetermined threshold, displaying an alert screen in response to a detected condition, wherein the alert screen is displayed in place of the first panel and the second panel, and controlling further output of the display device based on user actuation of at least one of a plurality of buttons disposed on the display device when the alert screen is displayed.

In one embodiment, the alert screen may be displayed in a third panel, wherein the third panel is displayed simultaneously with the first panel and the second panel.

In another embodiment, the graphical representation may include at least one event icon corresponding to a user event.

In a further embodiment, the user event may correspond to the detected condition.

In one embodiment, the graphical representation may include a first user defined analyte level threshold indicator and a second user defined analyte level threshold indicator, wherein when the current analyte level information passes at least one of the first analyte level threshold indicator or the second analyte level threshold indicator, an analyte level alert is displayed.

A further embodiment may include displaying a plurality of iconic status representations of a plurality of components of the display device, wherein the plurality of iconic status representations are displayed on a third panel of the display screen of the display device, wherein the third panel is simultaneously displayed with the first panel and the second panel.

Another embodiment may include automatically rotating the displayed alert screen into a predetermined orientation based on a type of detected condition.

Yet another embodiment may include displaying a menu screen on a third panel of the display screen of the display device, wherein the third panel is simultaneously displayed with the first panel and the second panel.

Another aspect of the present disclosure may include an analyte monitoring device having a user interface, wherein the user interface may include a display, wherein the display is configured to simultaneously display a plurality of distinct panels, wherein a first panel of the plurality of distinct panels displays historical analyte level information over a predetermined amount of time, and wherein a second panel of the plurality of distinct panels displays real-time analyte level information, and displays an alert screen in response to an alert condition being detected, wherein the alert screen is displayed in place of the plurality of distinct panels when the alert condition is detected, and a plurality of buttons, wherein at least one of the plurality of buttons is configured to interact with at least one of the plurality of panels when the plurality of panels are displayed and wherein at least the one of the plurality of buttons is configured to interact with the alert screen when the alert screen is displayed.

In one embodiment, actuation of the at least one of the plurality of buttons may be configured to affect an output of the analyte monitoring device when the alert screen is displayed.

In another embodiment, the output of the monitoring device may comprise at least one of a display output, an audible output, a vibratory output, and a combination thereof.

In one embodiment, the detected alert condition may correspond to one of a low urgency alert condition, an intermediate urgency alert condition, a medium urgency alert condition, and high urgency alert condition.

In another embodiment, the alert screen may be displayed in a rotated position based on a type of condition the alert screen represents.

In one aspect of the present disclosure a user interface for a personal medical device may include a display configured to display a home screen having a first section configured to display color coded graphical information corresponding to historic analyte levels of a user and a second section configured to simultaneously display color coded textual information corresponding to current analyte levels of the user, and a plurality of alert screens, wherein the plurality of alert screens are hierarchically arranged based on a severity of a condition that each of the plurality of alert screens represent, and a plurality of buttons, wherein the plurality of buttons have a first functionality when the home screen is displayed and wherein the plurality of buttons have a second functionality when each of the plurality of alert screens are displayed.

In one embodiment, a size of the first section of the home page may be adjustable with respect to a size of the second section of the home page.

In another embodiment, a position of the first section of the home page may be adjustable with respect to a position of the second section of the home page.

In another embodiment, one of the plurality of alert screens may be displayed in a third section of the home screen, wherein the third section of the home screen is simultaneously displayed with the first section of the home screen and the second section of the home screen.

In one embodiment, when the third section of the home screen is displayed, a size of the first section of the home screen and a size of the second section of the home screen may be automatically adjusted.

In one embodiment, the display may be a self-orientating display.

In another embodiment, the orientation of the display may be automatically adjusted based on one of the plurality of alert screens displayed.

One embodiment may further include a third section, wherein the third section of the home screen displays a plurality of icons representing respective components of the personal medical device, and wherein the third section is simultaneously displayed with the first section of the home screen and the second section of the home screen.

In one embodiment, when at least one alarm screen is displayed, it may be displayed in at least one of the first section of the home screen, the second section of the home screen or the third section of the home screen.

In one embodiment, a first alert screen having a first hierarchical order may be displayed in one of the first section of the home screen or the second section of the home screen, and wherein a second alert screen having a second hierarchical order is displayed in the other of the first section of the home screen or the second section of the home screen.

Another aspect of the present disclosure may include receiving a plurality of analyte levels including a most recent analyte level and at least one historical analyte level, defining a plurality of threshold values with respect to the most recent analyte level, retrospectively comparing the at least one historical analyte level to at least one of the plurality of threshold values to determine whether the at least one historical analyte level exceeds the at least one of the plurality of threshold values, and outputting an alert notification when the at least one historical analyte level exceeds the at least one of the plurality of threshold values.

A further embodiment may include determining whether the at least one historical analyte level was received within a predetermined window and retrospectively comparing the at least one historical analyte level to the at least one of the plurality of threshold values when it is determined that the at least one historic analyte level was received within the predetermined window.

In one embodiment, the predetermined window may be defined by a minimum time duration with respect to the most recent analyte level and a maximum time duration with respect to the most recent analyte level information.

In another embodiment, the at least one of the plurality of threshold values may correspond to a maximum rate of change of the historical analyte value over a predetermined time period.

In another aspect, an apparatus may include one or more processors, and a memory for storing instructions for access by the one or more processors which when executed, receives a plurality of analyte levels including a most recent analyte level and at least one historical analyte level, defines a plurality of threshold values with respect to the most recent analyte level, retrospectively compares the at least one historical analyte level to at least one of the plurality of threshold values to determine whether the at least one historical analyte level exceeds the at least one of the plurality of threshold values, and outputs an alert notification when the at least one historical analyte level exceeds the at least one of the plurality of threshold values In one embodiment, the memory for storing instructions for access by the one or more processors, which when executed, may determine whether the at least one historical analyte level was received within a predetermined window and retrospectively compares the at least one historical analyte level to the at least one of the plurality of threshold values when it is determined that the at least one historic analyte level was received within the predetermined window.

In one embodiment, the predetermined window may be defined by a minimum time duration with respect to the most recent analyte level and a maximum time duration with respect to the most recent analyte level information.

In another embodiment, the at least one of the plurality of threshold values may correspond to a maximum rate of change of the historical analyte value over a predetermined time period.

In one embodiment, at least one of the actuators may be illuminated by a lighting assembly.

In one embodiment, the lighting assembly may include a light source and a light pipe, wherein the light pipe is configured to direct light from the light source to the at least one of the actuators.

One embodiment may include a test strip port.

In another embodiment, at least a portion of the test strip port may be illuminated by an illumination assembly.

In another embodiment, the illumination assembly may include a light source and light pipe, and wherein at least a portion of the test strip port comprises the light pipe.

In another aspect of the present disclosure, an analyte monitoring device may include a housing, a display disposed in the housing, wherein the display is configured to output a plurality of distinct display areas, wherein at least one of the distinct display areas is configured to output data corresponding measured analyte levels received from a transcutaneously positioned sensor and at least a second one of the distinct display areas is configured to output data corresponding to the analyte monitoring device, a plurality of actuators disposed in the housing wherein at least one of the plurality of actuators is configured to interact with at least one of the distinct display areas, and an illumination assembly disposed in the housing, wherein the illumination assembly is configured to transfer light from a first area of the housing to a second area of the housing.

In one embodiment, the illumination assembly may include at least one light source and at least one light pipe.

Another embodiment may include a test strip port configured to receive a test strip.

In one embodiment, the illumination assembly may be configured to illuminate at least a portion of the test strip port.

In another embodiment, at least a portion of the test strip port may comprise at least a portion of the illumination assembly.

In another embodiment, the illumination assembly may be automatically activated in response to a test strip being inserted into the test strip port.

In one embodiment, the illumination assembly may be configured to simultaneously direct light to the first area of the housing and second area of the housing.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A method for displaying healthcare information to a user using a hand-held computing device, comprising:
    displaying on a touch-sensitive display of a computing device a first window comprising a plurality of charts including at least one glucose trend line and a target range, the target range comprising a lower boundary and an upper boundary, the lower boundary associated with a first glucose concentration value and the upper boundary associated with a second glucose concentration value, wherein the second glucose concentration value is greater than the first glucose concentration value, wherein the at least one glucose trend line and the target range are displayed simultaneously in the first window, wherein the trend line is indicative of a glucose level of a host over a first time period;
    generating a first event indicator on the plurality of charts in response to a first user input, wherein the first event indicator is positioned on the plurality of charts proximate to the at least one glucose trend line of the plurality of charts to indicate when an insulin delivery event occurred in time;
    generating a second event indicator on the plurality of charts in response to a second user input, wherein the second event indicator is positioned on the plurality of charts proximate to the at least one glucose trend line of the plurality of charts to indicate when a meal event occurred in time;
    detecting on the touch-sensitive display a user selection of at least one of the first or second event indicator;
    displaying on the touch-sensitive display information associated with the selected at least one of the first or second event indicator in a second window in response to detecting the user selection of the at least one of the first or second event indicator, wherein the second window is separate from the first window, wherein the second window replaces the first window; and
    changing a time period of the chart from the first time period to a second, different time period in response to a third user input detected by the computing device, wherein changing the time period causes the first and second event indicators to move on the plurality of charts so that the first and second event indicators continue to indicate when the insulin delivery event and the meal event occurred in time.

2. The method of claim 1, further comprising displaying the glucose information in a first display mode on the computing device when the computing device is in a portrait orientation, or in a second display mode on the computing device when the computing device is in a landscape orientation.

3. The method of claim 1, wherein the third user input is indicative of a request to change the time period to one of a plurality of predetermined time periods.

4. The method of claim 1, wherein the first user input and the second user input comprise touching a portion of at least one of the plurality of charts.

5. The method of claim 1, wherein detecting the user selection comprises detecting a user-touch of the at least one of the first or second event indicator on the display.

6. A non-transitory computer-readable storage medium having one or more sequences of instructions stored therein, wherein the one or more sequences of instructions, when executed by a processor, cause the processor to:
    display on a touch-sensitive display of a computing device a first window comprising a plurality of charts including at least one glucose trend line and a target range, the target range comprising a lower boundary and an upper boundary, the lower boundary associated with a first glucose concentration value and the upper boundary associated with a second glucose concentration value, wherein the second glucose concentration value is greater than the first glucose concentration value, wherein the at least one glucose trend line and the target range are displayed simultaneously in the first window, wherein the trend line is indicative of a glucose level of a host over a first time period;
    generate a first event indicator on the plurality of charts in response to a first user input, wherein the first event indicator is positioned on the plurality of charts proximate to the at least one glucose trend line of the plurality of charts to indicate when an insulin delivery event occurred in time;
    generate a second event indicator on the plurality of charts in response to a second user input, wherein the second event indicator is positioned on the plurality of charts proximate to the at least one glucose trend line of the plurality of charts to indicate when a meal event occurred in time;
    detect on the touch-sensitive display a user selection of at least one of the first or second event indicator;
    display on the touch-sensitive display information associated with the selected at least one of the first or second event indicator in a second window in response to detecting the user selection of the at least one of the first or second event indicator, wherein the second window is separate from the first window, wherein the second window replaces the first window; and
    change a time period of the chart from the first time period to a second, different time period in response to a third user input detected by the computing device, wherein changing the time period causes the first and second event indicators to move on the plurality of charts so that the first and second event indicators continue to indicate when the insulin delivery event and the meal event occurred in time.

7. The computer-readable storage medium of claim 6, wherein the one or more sequences of instructions further comprises displaying the glucose information in a first display mode on the computing device when the computing device is in a portrait orientation, or in a second display mode on the computing device when the computing device is in a landscape orientation.

8. The computer-readable storage medium of claim 6, wherein the third user input is indicative of a request to change the time period to one of a plurality of predetermined time periods.

9. The computer-readable storage medium of claim 6, wherein detecting the user selection comprises detecting a user-touch of the at least one of the first or second event indicator on the display.

10. The computer-readable storage medium of claim 6, wherein the computer-readable storage medium and the processor are stored in the computing device, wherein the computing device is a mobile phone.

11. A method for displaying healthcare information to a user using a hand-held computing device, comprising:
  opening an application on the hand-held computing device responsive to the computing device detecting a first user input;
  displaying on a touch-sensitive display of the computing device a first window comprising a plurality of charts including at least one glucose trend line and a target range, the target range comprising a lower boundary and an upper boundary, the lower boundary associated with a first glucose concentration value and the upper boundary associated with a second glucose concentration value, wherein the second glucose concentration value is greater than the first glucose concentration value, wherein the at least one glucose trend line and the target range are displayed simultaneously in the first window, wherein the trend line is indicative of a glucose level of a host over a first time period;
  generating a first event indicator on the plurality of charts in response to a second user input, wherein the first event indicator is positioned on the plurality of charts to indicate when an insulin delivery event occurred in time;
  generating a second event indicator on the plurality of charts in response to a third user input, wherein the second event indicator is positioned on the plurality of charts to indicate when a meal event occurred in time;
  detecting on the touch sensitive display a user selection of at least one of the first or second event indicator;
  displaying on the touch-sensitive display information associated with the selected at least one of the first or second event indicator in a second window in response to detecting the user selection of the at least one of the first or second event indicator, wherein the second window is separate from the first window, wherein the second window replaces the first window;
  prompting an alert after detecting a hypoglycemic or hyperglycemic event; and
  changing a time period of the chart from the first time period to a second, different time period in response to a fourth user input detected by the computing device, wherein changing the time period causes the first and second event indicators to move on the plurality of charts so that the first and second event indicators continue to indicate when the insulin delivery event and the meal event occurred in time.

12. The method of claim 11, further comprising sharing, in response to the computing device detecting a fifth user input, glucose information on the computing device with a second computing device.

13. The method of claim 12, wherein the computing device is a mobile phone, and wherein the second computing device is a mobile phone.

14. The method of claim 11, further comprising displaying the glucose information in a first display mode on the computing device when the computing device is in a portrait orientation, or in a second display mode on the computing device when the computing device is in a landscape orientation, wherein the glucose information is displayed differently in the first display mode than the second display mode.

15. The method of claim 14, wherein the second display mode displays the glucose information as raw data.

16. The method of claim 11, wherein the second user input and the third user input comprise touching a portion of at least one of the plurality of charts, and wherein the fourth user input is indicative of a request to change the time period to one of a plurality of predetermined time periods.

17. The method of claim 11, wherein detecting the user selection comprises detecting a user-touch of the at least one of the first or second event indicator on the display.

18. A non-transitory computer-readable storage medium having one or more sequences of instructions stored therein, wherein the one or more sequences of instructions, when executed by a processor, cause the processor to:
  open an application on a hand-held computing device in response to the computing device detecting a first user input;
  display on a touch-sensitive display of the computing device a first window comprising a plurality of charts including at least one glucose trend line and a target range, the target range comprising a lower boundary and an upper boundary, the lower boundary associated with a first glucose concentration value and the upper boundary associated with a second glucose concentration value, wherein the second glucose concentration value is greater than the first glucose concentration value, wherein the at least one glucose trend line and the target range are displayed simultaneously in the first window, wherein the trend line is indicative of a glucose level of a host over a first time period;
  generate a first event indicator on the plurality of charts in response to a second user input, wherein the first event indicator is positioned on the plurality of charts to indicate when an insulin delivery event occurred in time;
  generate a second event indicator on the plurality of charts in response to a third user input, wherein the second event indicator is positioned on the plurality of charts to indicate when a meal event occurred in time;
  detect on the touch sensitive display a user selection of at least one of the first or second event indicator;
  display on the touch-sensitive display information associated with the selected at least one of the first or second event indicator in a second window in response to detecting the user selection of the at least one of the first or second event indicator, wherein the second window is separate from the first window, wherein the second window replaces the first window;
  prompt an alert after detecting a hypoglycemic or hyperglycemic event; and
  change a time period of the chart from the first time period to a second, different time period in response to a fourth user input detected by the computing device, wherein changing the time period causes the first and second event indicators to move on the plurality of charts so that the first and second event indicators continue to indicate when the insulin delivery event and the meal event occurred in time.

19. The computer-readable storage medium of claim 18, wherein the one or more sequences of instructions further comprises sharing, in response to the computing device detecting a fifth user input, glucose information on the computing device with a second computing device.

20. The computer-readable storage medium of claim 19, wherein the computing device is a mobile phone, and wherein the second computing device is a mobile phone.

21. The computer-readable storage medium of claim 18, wherein the one or more sequences of instructions further comprises displaying the glucose information in a first display mode on the computing device when the computing device is in a portrait orientation, or in a second display mode on the computing device when the computing device is in a landscape orientation.

22. The computer-readable storage medium of claim 21, wherein the second display mode displays the glucose information as raw data.

23. The computer-readable storage medium of claim 18, wherein the second user input and the third user input comprise touching a portion of at least one of the plurality of charts, and wherein the fourth user input is indicative of a request to change the time period to one of a plurality of predetermined time periods.

24. The computer-readable storage medium of claim 18, wherein detecting the user selection comprises detecting a user-touch of the at least one of the first or second event indicator on the display.

25. The computer-readable storage medium of claim 18, wherein the computing device includes the computer-readable storage medium and the processor, and wherein the computing device is a mobile phone.

\* \* \* \* \*